US012806041B2

(12) United States Patent
Goldberg et al.

(10) Patent No.: US 12,806,041 B2
(45) Date of Patent: Nov. 24, 2026

(54) METHODS OF PERSONALIZING DRUG TREATMENT BASED ON REAL-TIME PRESSURE GRADIENT MEASUREMENTS

(71) Applicant: Edwards Lifesciences Corporation, Irvine, CA (US)

(72) Inventors: Eran Goldberg, Nesher (IL); Noam Nir, Pardes-Hanna (IL)

(73) Assignee: Edwards Lifesciences Corporation, Irvine, CA (US)

( * ) Notice: Subject to any disclaimer, the term of this patent is extended or adjusted under 35 U.S.C. 154(b) by 1212 days.

(21) Appl. No.: 17/805,015

(22) Filed: Jun. 1, 2022

(65) Prior Publication Data

US 2022/0287851 A1 Sep. 15, 2022

Related U.S. Application Data

(63) Continuation of application No. PCT/US2020/063020, filed on Dec. 3, 2020.
(Continued)

(51) Int. Cl.
*A61F 2/24* (2006.01)
*A61B 5/00* (2006.01)
(Continued)

(52) U.S. Cl.
CPC ............ *A61F 2/482* (2021.08); *A61B 5/4851* (2013.01); *A61B 5/6862* (2013.01);
(Continued)

(58) Field of Classification Search
CPC .............. A61B 2560/0219; A61B 5/01; A61B 2562/0271; A61B 5/00; A61B 5/0004;
(Continued)

(56) References Cited

U.S. PATENT DOCUMENTS 5,199,428 A 4/1993 Obel et al.
6,309,350 B1 10/2001 Vantassel et al.
(Continued)

FOREIGN PATENT DOCUMENTS

CN 101271029 A 9/2008
CN 105193529 A 12/2015
(Continued)

OTHER PUBLICATIONS

Abraham W.T., et al., "V-LAP Left Atrial Monitoring systEm for Patients with Chronic sysTOlic and Diastolic Congestive Heart FailuRe First-in-Human," Journal of Cardial Failure, Churchill Livingstone, Naperville, IL, US, Aug. 1, 2019, vol. 25, No. 8S, pp. S74-S75 (2 Pages).

(Continued)

*Primary Examiner* — Seema Mathew
(74) *Attorney, Agent, or Firm* — Klarquist Sparkman LLP

(57) ABSTRACT

A valve monitoring assembly, constituted of: a prosthetic valve, constituted of a frame and leaflets positioned at least partially within the frame, that regulate blood flow through the prosthetic valve; and a monitoring apparatus constituted of: at least one sensor associated with the prosthetic valve, wherein the at least one sensor is selected from the group consisting of: flow sensor, pressure sensor, and temperature sensor; a local control circuitry; at least one communication component configured to wirelessly transmit signals; and an energy harvesting power source, configured to be secured to a patient and comprising a self-powered energy harvesting mechanism and an energy storage member, wherein the energy storage member is configured to store energy generated by the self-powered energy harvesting mechanism, and wherein the energy harvesting power source is configured to supply power to the at least one sensor, the local
(Continued)

control circuitry and/or the at least one communication component.

20 Claims, 18 Drawing Sheets

Related U.S. Application Data

(60) Provisional application No. 62/945,022, filed on Dec. 6, 2019.

(51) Int. Cl.

| | |
|---|---|
| ***A61F 2/48*** | (2006.01) |
| ***G16H 40/63*** | (2018.01) |
| ***H02K 7/18*** | (2006.01) |
| ***H02K 11/00*** | (2016.01) |
| ***H02S 10/40*** | (2014.01) |
| ***H02S 40/38*** | (2014.01) |

(52) U.S. Cl.
CPC ........... *A61F 2/2418* (2013.01); *G16H 40/63* (2018.01); *H02K 7/1853* (2013.01); *H02K 11/0094* (2013.01); *H02S 10/40* (2014.12); *H02S 40/38* (2014.12); *A61F 2250/0002* (2013.01)

(58) Field of Classification Search
CPC ..... A61B 5/0031; A61B 5/0205; A61B 5/021; A61B 5/026; A61B 5/029; A61B 5/4851; A61B 5/6802; A61B 5/686; A61B 5/6867; A61B 5/14532; A61B 5/6862; A61B 5/0024; A61B 2560/0209; A61B 5/1122; A61B 5/0002; A61B 5/1114; A61B 2562/0247; A61B 5/0022; A61B 5/076; A61B 5/6869; A61B 5/02055; A61B 2562/08; A61B 5/02014; A61B 5/02108; A61B 5/0028; A61B 5/4866; A61B 5/6885; A61F 2/2418; A61F 2/243; A61F 2/2439; A61F 2/482; A61F 2250/0001; A61F 2250/0002; A61F 2/2409; A61F 2/2472; A61F 2/07; A61F 2/24; A61F 2/82; A61F 2002/4666; A61F 2/488; A61F 2002/4672; A61F 2002/467; A61F 2250/0085; A61F 2/86; A61F 2250/00
See application file for complete search history.

(56) References Cited

U.S. PATENT DOCUMENTS

| | | | | |
|---|---|---|---|---|
| 6,783,499 | B2 | 8/2004 | Schwartz | |
| 7,340,288 | B1 | 3/2008 | Karicherla et al. | |
| 7,389,142 | B2 | 6/2008 | Holmstroem | |
| 7,452,334 | B2 | 11/2008 | Gianchandani et al. | |
| 7,769,420 | B2 * | 8/2010 | Silver | A61B 5/6882 600/300 |
| 8,175,668 | B1 | 5/2012 | Nabutovsky et al. | |
| 8,462,678 | B2 * | 6/2013 | Splinter | A61N 1/37254 370/310 |
| 8,929,982 | B2 | 1/2015 | Holmstrom et al. | |
| 9,999,528 | B2 | 6/2018 | Kim et al. | |
| 10,806,352 | B2 | 10/2020 | Sweeney et al. | |
| 11,039,924 | B2 | 6/2021 | Yaron | |
| 2002/0111666 | A1 * | 8/2002 | Hart | A61F 2/95 623/1.11 |
| 2002/0151816 | A1 * | 10/2002 | Rich | A61B 5/02028 600/547 |
| 2005/0065589 | A1 | 3/2005 | Schneider et al. | |
| 2005/0267478 | A1 | 12/2005 | Corradi et al. | |
| 2006/0020324 | A1 | 1/2006 | Schmid et al. | |
| 2006/0161171 | A1 | 7/2006 | Schwartz | |
| 2006/0200031 | A1 * | 9/2006 | White | A61B 5/0215 600/486 |
| 2007/0021665 | A1 | 1/2007 | Hettrick et al. | |
| 2007/0118039 | A1 * | 5/2007 | Bodecker | A61B 5/02158 128/903 |
| 2007/0129637 | A1 | 6/2007 | Wolinsky et al. | |
| 2007/0244373 | A1 * | 10/2007 | Osypka | A61F 2/86 600/301 |
| 2008/0051863 | A1 | 2/2008 | Schneider et al. | |
| 2008/0082005 | A1 | 4/2008 | Stern et al. | |
| 2008/0146890 | A1 * | 6/2008 | LeBoeuf | A61B 5/0002 600/300 |
| 2009/0024042 | A1 | 1/2009 | Nunez et al. | |
| 2009/0248105 | A1 | 10/2009 | Keilman et al. | |
| 2009/0270742 | A1 * | 10/2009 | Wolinsky | A61B 5/6882 600/486 |
| 2010/0179449 | A1 | 7/2010 | Chow et al. | |
| 2011/0288436 | A1 | 11/2011 | Stone | |
| 2012/0022507 | A1 | 1/2012 | Najafi et al. | |
| 2012/0116489 | A1 | 5/2012 | Khairkhahan et al. | |
| 2012/0239142 | A1 | 9/2012 | Liu et al. | |
| 2012/0259217 | A1 | 10/2012 | Gerrans et al. | |
| 2012/0265296 | A1 | 10/2012 | McNamara et al. | |
| 2012/0291788 | A1 * | 11/2012 | Griswold | A61B 5/0215 128/898 |
| 2013/0046152 | A1 | 2/2013 | Najafi et al. | |
| 2013/0165967 | A1 | 6/2013 | Amin et al. | |
| 2013/0281774 | A1 | 10/2013 | Honaryar et al. | |
| 2013/0317367 | A1 * | 11/2013 | Shuler | A61B 5/416 600/473 |
| 2013/0338763 | A1 | 12/2013 | Rowe et al. | |
| 2014/0107722 | A1 | 4/2014 | Kaiser et al. | |
| 2014/0155768 | A1 | 6/2014 | Orion et al. | |
| 2014/0214149 | A1 | 7/2014 | Kuraguntla et al. | |
| 2015/0025612 | A1 | 1/2015 | Haasl et al. | |
| 2015/0112383 | A1 | 4/2015 | Sherman et al. | |
| 2015/0157268 | A1 | 6/2015 | Winshtein et al. | |
| 2015/0313496 | A1 * | 11/2015 | Connor | A61B 5/02055 600/301 |
| 2015/0351648 | A1 | 12/2015 | Harvey et al. | |
| 2016/0045165 | A1 | 2/2016 | Braido et al. | |
| 2016/0045316 | A1 | 2/2016 | Braido et al. | |
| 2016/0157868 | A1 | 6/2016 | Tillman et al. | |
| 2016/0256141 | A1 | 9/2016 | Mendez et al. | |
| 2016/0338823 | A1 | 11/2016 | Akingba | |
| 2017/0095163 | A1 | 4/2017 | Bitzer et al. | |
| 2017/0319067 | A1 | 11/2017 | Najafi | |
| 2018/0071542 | A1 | 3/2018 | Nyberg et al. | |
| 2018/0098772 | A1 | 4/2018 | Goldshtein et al. | |
| 2018/0140444 | A1 | 5/2018 | Neuss et al. | |
| 2018/0168460 | A1 | 6/2018 | Morris et al. | |
| 2019/0083801 | A1 | 3/2019 | Yang et al. | |
| 2019/0133472 | A1 * | 5/2019 | Kim | G16H 50/30 |
| 2019/0343388 | A1 | 11/2019 | Bahmanyar et al. | |
| 2020/0054867 | A1 | 2/2020 | Schwartz et al. | |
| 2020/0094048 | A1 | 3/2020 | Regnier et al. | |
| 2020/0155014 | A1 | 5/2020 | Arthur et al. | |
| 2020/0196944 | A1 | 6/2020 | Minor et al. | |
| 2020/0289257 | A1 | 9/2020 | Marquez et al. | |
| 2021/0000581 | A9 | 1/2021 | Eigler et al. | |
| 2021/0121130 | A1 | 4/2021 | Nagy et al. | |
| 2021/0177277 | A1 | 6/2021 | Cros et al. | |
| 2021/0282921 | A1 * | 9/2021 | Schwarcz | A61F 2/9517 |
| 2022/0008014 | A1 | 1/2022 | Rowe et al. | |
| 2023/0144909 | A1 * | 5/2023 | Leichner | A61F 2/2418 623/2.18 |
| 2023/0248249 | A1 | 8/2023 | Keidar et al. | |
| 2024/0285404 | A1 * | 8/2024 | Schwarcz | A61F 2/2439 |
| 2026/0013985 | A1 * | 1/2026 | Levi | A61F 2/2418 |

FOREIGN PATENT DOCUMENTS

| | | | | |
|---|---|---|---|---|
| EP | 2338420 | A1 | 6/2011 | |
| WO | WO-2007057739 | A1 | 5/2007 | |
| WO | WO-2007058872 | A2 | 5/2007 | |
| WO | WO-2008034077 | A2 * | 3/2008 | A61B 5/0031 |

(56) References Cited

FOREIGN PATENT DOCUMENTS

| | | | | | |
|---|---|---|---|---|---|
| WO | WO-2009155571 | A1 | * | 12/2009 | ........... A61B 17/221 |
| WO | WO-2012031204 | A2 | | 3/2012 | |
| WO | WO-2012057861 | A1 | * | 5/2012 | ........... A61B 5/6882 |
| WO | WO-2015200707 | A1 | * | 12/2015 | ............. G16B 40/10 |
| WO | WO-2016178171 | A1 | | 11/2016 | |
| WO | WO-2018213320 | A1 | | 11/2018 | |
| WO | WO-2020117887 | A1 | * | 6/2020 | ........... A61F 2/2439 |
| WO | WO-2020123338 | A1 | | 6/2020 | |
| WO | WO-2020163112 | A1 | | 8/2020 | |
| WO | WO-2021015929 | A1 | | 1/2021 | |
| WO | WO-2021050589 | A1 | | 3/2021 | |
| WO | WO-2021113449 | A1 | | 6/2021 | |
| WO | WO-2022046425 | A1 | | 3/2022 | |
| WO | WO-2022046473 | A1 | | 3/2022 | |
| WO | WO-2022051716 | A1 | | 3/2022 | |
| WO | WO-2023177824 | A1 | | 9/2023 | |

OTHER PUBLICATIONS

Chow E.Y., et al., "Toward an Implantable Wireless Cardiac Monitoring Platform Integrated with an FDA-Approved Cardiovascular Stent," Journal of Interventional Cardiology, 2009, vol. 22, No. 5, pp. 479-487, Wiley Periodicals, Inc., Hoboken, New Jersey.

Hur T., et al., "Improving Structural Strength and Stability of Parylene-based Capacitive Micro Pressure Sensor Using Corrugated Sidewall", MEMS 2019, Jan. 2019, pp. 727-730. I XP093213755, Retrieved from the Internet: URL:https://ieeexplore.ieee.org/stampPDF/getPDF.jsp?tp=&arnumber=8870736&ref=aHR0cHM6Ly9zY2hvbGFyLmdvb2dsZSSjb20v figures 1-6.

Kim A., et al., "An Implantable Pressure Sensing System With Electromechanical Interrogation Scheme," IEEE Transactions on Biomedical Engineering, IEEE, USA, Jul. 1, 2014, vol. 61(7), pp. 2209-2217, DOI: 10.1109/TBME.2014.2318023, ISSN 0018-9294, XP011551241, (Jun. 16, 2014).

Neema P.K., et al., "Left Atrial Pressure Waveform: Does It Show Mitral Insufficiency," Journal of Cardiothoracic and Vascular Anesthesia, Diagnostic Dilemmas, Elsevier, Amsterdam, NL, Apr. 2008, vol. 22, No. 2, pp. 318-320, Mar. 28, 2008.

Nitter-Hauge S., et al., "Clinical and Hemodynamic Results After Combined Aortic and Mitral Valve Replacement With the Lillehei-Kaster Pivoting Disc Valve," Experimental and Laboratory Reports, American Heart Journal, May 1, 1979, vol. 97, No. 5, pp. 599-607.

O'Rourke R.A., et al., "Mitral Valve Regurgitation," Current Problems in Cardiology, May 1, 1984, vol. 9, No. 3, pp. 1-52.

Snyder R.W.S., et al., "Predictive Value of Prominent Pulmonary Arterial Wedge V Waves in Assessing the Presence and Severity of Mitral Regurgitation," Valvular Heart Disease, The American Journal of Cardiology, Mar. 15, 1994, vol. 73, No. 8, pp. 568-570.

Tice F.D., et al., "Transesophageal Echocardiographic Assessment of Reversal of Systolic Pulmonary Venous Flow in Mitral Stenosis," The American Journal of Cardiology, Jan. 1, 1995, vol. 75, No. 1, pp. 58-60.

* cited by examiner

METHODS OF PERSONALIZING DRUG TREATMENT BASED ON REAL-TIME PRESSURE GRADIENT MEASUREMENTS

RELATED APPLICATIONS

This application is a continuation of International Patent Application No. PCT/US2020/063020, filed on Dec. 3, 2020, which application claims the benefit of U.S. Provisional Patent Application No. 62/945,022, filed on Dec. 6, 2019, each of these applications being incorporated herein in its entirety by this specific reference.

FIELD OF THE INVENTION

The present invention relates to devices and systems for monitoring of heart valves, such as prosthetic valves, to enable detection of conditions that may be correlated with functioning of the valves, and to methods for providing treatment recommendations based on monitored data associated either with heart valve functioning, or with other conditions that can be treated by drug-therapy protocols.

BACKGROUND OF THE INVENTION

Native heart valves, such as the aortic, pulmonary and mitral valves, function to assure adequate directional flow from, and to, the heart, and between the heart's chambers, to supply blood to the whole cardiovascular system. Various valvular diseases can render the valves ineffective and require replacement with artificial valves. Surgical procedures can be performed to repair or replace a heart valve. Since surgeries are prone to an abundance of clinical complications, alternative less invasive techniques of delivering a prosthetic heart valve over a catheter and implanting it over the native malfunctioning valve have been developed over the years.

Different types of prosthetic heart valves are known to date, including balloon expandable valve, self-expandable valves and mechanically-expandable valves. Different methods of delivery and implantation are also known, and may vary according to the site of implantation and the type of prosthetic valve. One exemplary technique includes utilization of a delivery assembly for delivering a prosthetic valve in a crimped state, from an incision which can be located at the patient's femoral or iliac artery, toward the native malfunctioning valve. Once the prosthetic valve is properly positioned at the desired site of implantation, it can be expanded against the surrounding anatomy, such as an annulus of a native valve, and the delivery assembly can be retrieved thereafter.

One of the complications that may be associated with implanted prosthetic heart valves is thrombus formation on the prosthetic structures, which can result in reduced leaflet motility or impaired coaptation, reduced effective valve orifice area, increased transvalvular pressure gradient, or transvalvular regurgitation. Various short- or long-term anticoagulation regimes have been implied to prevent thrombosis. However, routine post-procedural anticoagulation can be hazardous because different patients may have multiple comorbidities that could increase risks of bleeding, which may lead to a disabling or fatal stroke. The therapeutic window of anticoagulation becomes narrower because of the high bleeding risk, for example over the first three months after valve implantation. However, the risk of heart valve thrombosis cannot be limited to within the first three months, and in fact may persist beyond one year after valve implantation.

Early identification of subclinical valve thrombosis may be important for patient management, since if left untreated, it may lead to reduced effective orifice area and valve dysfunction, potentially converting to critical valve thrombosis. This underscores the importance of ongoing valve monitoring, for careful evaluation of the risks and benefits of long-term antiplatelet or anticoagulation therapies. Conventional post procedural imaging techniques, such as ultrasound or CT, are inappropriate for ongoing valve monitoring, as the resolution provided by external ultrasound detectors cannot detect subclinical thrombus formation or flow-related disturbances associated therewith, and high-resolution CT imaging is a complex and expensive procedure, which may subject the patient to additional risks of radiation. Thus, a need exists for improvements in devices, systems and methods that may provide routine, ongoing, monitoring of the valve, for early detection of conditions that may be associated with valve functioning, thereby assisting in devising recommendations for optimal prevention and treatment protocols.

SUMMARY OF THE INVENTION

The present disclosure is directed toward devices and systems for ongoing monitoring of the functioning of a heart valve. A monitoring apparatus includes at least one sensor configured to measure a flow characteristic (e.g., blood flow or pressure) in the vicinity of a native or a prosthetic heart valve, and a communication component configured to wirelessly transmit data measured by the at least one sensor (i.e., raw data and/or processed data) to an external reader unit. By monitoring flow characteristics in the vicinity of a valve, such as a native valve and/or a prosthetic valve, functioning of the valve, as well as pathological conditions that may influence such functioning, can be inferred.

The current disclosure is further directed to methods for early detection of conditions that may be associated with abnormal functioning of the heart valve, based on the measurement data provided by the devices and the systems mentioned above, and providing recommendations for prevention and/or treatment protocols based on analyzed measurement data.

According to one aspect of the invention, there is provided a valve monitoring assembly, comprising a prosthetic valve and a monitoring apparatus. The prosthetic valve comprises a frame having an inflow end portion and an outflow end portion, and a plurality of leaflets positioned at least partially within the frame, and configured to regulate a flow of blood through the prosthetic valve. The monitoring apparatus comprises at least one sensor associated with the prosthetic valve, a local control circuitry comprising a processor, at least one communication component, and an energy harvesting power source.

The at least one sensor is selected from the group consisting of: flow sensor, pressure sensor, and temperature sensor. The local control circuitry is in communication with the at least one sensor. The at least one communication component is in communication with the local control circuitry, and configured to wirelessly transmit signals. The energy harvesting power source is configured to be secured to a patient and comprises a self-powered energy harvesting mechanism and an energy storage member, wherein the energy storage member is configured to store energy generated by the self-powered energy harvesting mechanism.

The energy harvesting power source is configured to supply power to the at least one sensor, the local control circuitry and/or the at least one communication component.

According to some embodiments, the energy harvesting power source is coupled to the local control circuitry.

According to some embodiments, the energy harvesting power source further comprises a first tissue engagement feature configured to facilitate attachment of the energy harvesting power source to a tissue of the patient.

According to some embodiments, the self-powered energy harvesting mechanism is a clockwork-type energy harvesting mechanism, comprising an oscillating weight, a mechanical rectifier, a spring and an electromagnetic micro generator. The oscillating weight is configured to translate externally applied accelerations into oscillating rotational motions thereof. The mechanical rectifier is coupled to the mechanical weight, and configured to translate the oscillating rotational motions into a unidirectional rotation. The spring is coupled to the mechanical rectifier. The electromagnetic micro generator coupled to the spring, and configured to convert motion of the spring into an electrical signal.

According to some embodiments, the self-powered energy harvesting mechanism is a solar energy harvesting mechanism, comprising a solar module having at least one solar cell.

According to some embodiments, the solar energy harvesting mechanism further comprises a power converter functionally coupled to the solar module.

According to some embodiments, the at least one communication component comprises a remote communication component and a local communication component, wherein the remote communication component is configured to wirelessly transmit energy generated by the solar energy harvesting mechanism to the local communication component.

According to some embodiments, the remote communication component comprises a coil antenna configured to electromagnetically transmit the energy stored in the energy storage member, to the local communication component.

According to some embodiments, the remote communication component comprises an ultrasound transducer configured to transmit the energy stored in the energy storage member, to the local communication component.

According to some embodiments, the monitoring apparatus further comprises at least one communication channel connected to the local control circuitry and to the at least one sensor, and configured to deliver signals there-between.

According to some embodiments, the prosthetic valve that is radially expandable and compressible between a radially compressed state and a radially expanded state, wherein the frame comprises a plurality of cells bound between strut portions, and wherein the at least one communication channel extends along at least some of the strut portions.

According to some embodiments, the prosthetic valve further comprises at least one actuator assembly, wherein each actuator assembly comprises an outer member attached to the outflow end portion, and an inner member attached to the inflow end portion, and partially disposed within a lumen of the outer member. The prosthetic valve is expandable from the radially compressed state to the radially expanded state upon actuating the at least one actuator assembly. The at least one sensor is attached to the outer member of the at least one actuator assembly.

According to some embodiments, the frame comprises a rigid ring at the inflow end portion, and a plurality of commissure posts extending proximally from the rigid ring, wherein the at least one sensor is attached to at least one of the plurality of commissure posts.

According to some embodiments, the at least one sensor is embedded within the control circuitry.

According to some embodiments, the prosthetic valve further comprises at least one monitoring engagement member, configured to engage with the at least one sensor.

According to some embodiments, the monitoring apparatus further comprises a memory member, in communication with the processor, and configured to store signals sensed by the sensor and/or data processed by the processor.

According to some embodiments, the at least one sensor is coupled to the prosthetic valve.

According to some embodiments, the at least one sensor comprises a first pressure sensor coupled to the inflow end portion, and a second pressure sensor coupled to the outflow end portion.

According to some embodiments, the at least one sensor comprises a second tissue engagement feature configured to facilitate attachment of the at least one sensor to a tissue of the patient.

According to some embodiments, the at least one sensor is operatively coupled to the local control circuitry.

According to some embodiments, there is provided a valve monitoring system, comprising the valve monitoring assembly and an external reader unit. The external reader unit comprises at least one reader communication component, a reader processor configured to control functionality of the external reader unit, and a reader storage member. The at least one reader communication component is configured to wirelessly communicate with the at least one communication component of the monitoring apparatus. The reader storage member is configured to store data transmitted from the monitoring apparatus and/or data processed by the reader processor.

According to some embodiments, the external reader unit further comprises an external remote display and an external remote input interface.

According to some embodiments, the valve monitoring system further comprises at least one external remote monitoring device, comprising an external remote communication component, an external remote processor, an external remote storage member, an external remote display, and an external remote input interface. The external remote communication component is configured to communicate with the external reader unit. The external remote processor is configured to control functionality of the external remote monitoring device. The external remote storage member is configured to store data transmitted from the external reader unit and/or data processed by the external remote processor.

According to another aspect of the invention, there is provided a method for heart valve monitoring, comprising the steps of: measuring, by at least one implanted sensor of a monitoring apparatus, a flow characteristic at the heart valve of a patient; wirelessly transmitting, via a communication component of the monitoring apparatus, measurement data to at least one reader communication component of an external reader unit; analyzing, by a processor, measurement data according to a first rules set; determining, by the processor, at least one recommended treatment protocol, resulting from the analysis; displaying, by the processor, the at least one recommended protocol on a display; and storing, by the processor, measurement data in a storage member. The flow characteristic is selected from the group consisting of: blood flow, blood pressure, and temperature. The step of storing measurement data can be executed after any other step of the method.

According to some embodiments, the method further comprises the steps of: securing a self-powered energy harvesting mechanism to the patient; harvesting energy by the self-powered energy harvesting mechanism; storing the harvested energy in an energy storage member; and responsive to the stored energy, supplying power to the at least one implanted sensor and/or the communication component.

According to some embodiments, the monitored heart valve is a native heart valve, wherein the step of determining includes determining whether a prosthetic valve should be implanted within the native valve.

According to some embodiments, the monitored heart valve is a prosthetic heart valve, wherein the step of determining includes determining whether a valve-in-valve procedure should be performed.

According to some embodiments, the monitored heart valve is a prosthetic heart valve, wherein the step of determining includes determining whether a drug therapy protocol should be recommended, and if so, determine the drug therapy recommended regimen.

According to some embodiments, the step of analyzing according to the first rules set comprises analyzing the measurement data in combination with supplementary patient data, selected from the group consisting of: patient age, accompanying diseases, drug sensitivities, currently administered drugs, and any combination thereof.

According to some embodiments, the step of analyzing according to the first rules set comprises analyzing the measurement data in combination with additional data obtained from a heart rate monitor, an accelerometer and/or a posture sensor.

According to some embodiments, the method further comprises a step of comparing measurement data with threshold values, followed by a step of determining whether an abnormal valve-related condition is detected as a result of the comparison, both of which are performed after the step of measuring the flow characteristic and before the step of analyzing measurement data.

According to some embodiments, the method further comprises a step of transmitting, via the at least one reader communication component, measurement data to an external remote communication component of an external remote monitoring device.

According to some embodiments, the method further comprises, after the step of transmitting measurement data, and responsive to the patient currently being under a previously recommended drug therapy, performing the following steps: retrieving, by the processor, stored measurement data from a storage member; analyzing, by the processor, current measurement data in combination with the retrieved measurement data, according to a second rules set; determining, by the processor, whether the current drug therapy regimen should be modified; and displaying, by the processor, the recommended course of action for the current drug therapy regimen on the display.

According to some embodiments, the step of analyzing according to the second rules set comprises analyzing the measurement data in combination with supplementary patient data, selected from the group consisting of: patient age, accompanying diseases, drug sensitivities, currently administered drugs, and any combination thereof.

According to some embodiments, the step of analyzing according to the second rules set comprises analyzing the measurement data in combination with additional data obtained from a heart rate monitor, an accelerometer and/or a posture sensor.

According to another aspect of the invention, there is provided a method for monitoring conditions that may be treated by drug therapy protocols, comprising the steps of: measuring, by at least one implanted sensor of a monitoring apparatus, a flow characteristic at the heart valve of a patient; wirelessly transmitting, via a communication component of the monitoring apparatus, measurement data to at least one reader communication component of an external reader unit; analyzing, by a processor, measurement data according to a first rules set; determining, by the processor, whether at least one drug therapy protocol should be recommended, and if so, determine the drug therapy recommended regimen, resulting from the analysis; displaying, by the processor the at least one recommended protocol on a display; and storing measurement data in a storage member. The flow characteristic is selected from the group consisting of: blood flow, blood pressure, and temperature. The step of storing measurement data can be executed after any other step of the method.

According to some embodiments, the method further comprises the steps of: securing a self-powered energy harvesting mechanism to the patient; harvesting energy by the self-powered energy harvesting mechanism; storing the harvested energy in an energy storage member; and responsive to the stored energy, supplying power to the at least one implanted sensor and/or the communication component.

According to some embodiments, the step of analyzing according to the first rules set comprises analyzing the measurement data in combination with supplementary patient data, selected from the group consisting of: patient age, accompanying diseases, drug sensitivities, currently administered drugs, and any combination thereof.

According to some embodiments, the step of analyzing according to the first rules set comprises analyzing the measurement data in combination with additional data obtained from a heart rate monitor, an accelerometer and/or a posture sensor.

According to some embodiments, the method further comprises a step of comparing measurement data with threshold values, followed by a step of determining whether an abnormal condition is detected as a result of the comparison, both of which are performed after the step of measuring the flow characteristic and before the step of analyzing measurement data.

According to some embodiments, the method further comprises a step of transmitting, via the at least one reader communication component, measurement data to an external remote communication component of an external remote monitoring device.

According to some embodiments, the method further comprises, after the step of transmitting measurement data, and responsive to the patient currently being under a previously recommended drug therapy, performing the following steps: retrieving, by the processor, stored measurement data from a storage member; analyzing, by the processor, current measurement data in combination with the retrieved measurement data, according to a second rules set; determining, by the processor, whether the current drug therapy regimen should be modified; and displaying, by the processor, the recommended course of action for the current drug therapy regimen on the display.

According to some embodiments, the step of analyzing according to the second rules set comprises analyzing the measurement data in combination with supplementary patient data, selected from the group consisting of: patient age, accompanying diseases, drug sensitivities, currently administered drugs, and any combination thereof.

According to some embodiments, the step of analyzing according to the second rules set comprises analyzing the measurement data in combination with additional data obtained from a heart rate monitor, an accelerometer and/or a posture sensor.

Certain embodiments of the present invention may include some, all, or none of the above advantages. Further advantages may be readily apparent to those skilled in the art from the figures, descriptions, and claims included herein. Aspects and embodiments of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following embodiments and aspects thereof are described and illustrated in conjunction with systems, tools and methods which are meant to be exemplary and illustrative, but not limiting in scope. In various embodiments, one or more of the above-described problems have been reduced or eliminated, while other embodiments are directed to other advantages or improvements.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures.

DETAILED DESCRIPTION OF SOME EMBODIMENTS

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. In order to avoid undue clutter from having too many reference numbers and lead lines on a particular drawing, some components will be introduced via one or more drawings and not explicitly identified in every subsequent drawing that contains that component.

Figure 1:
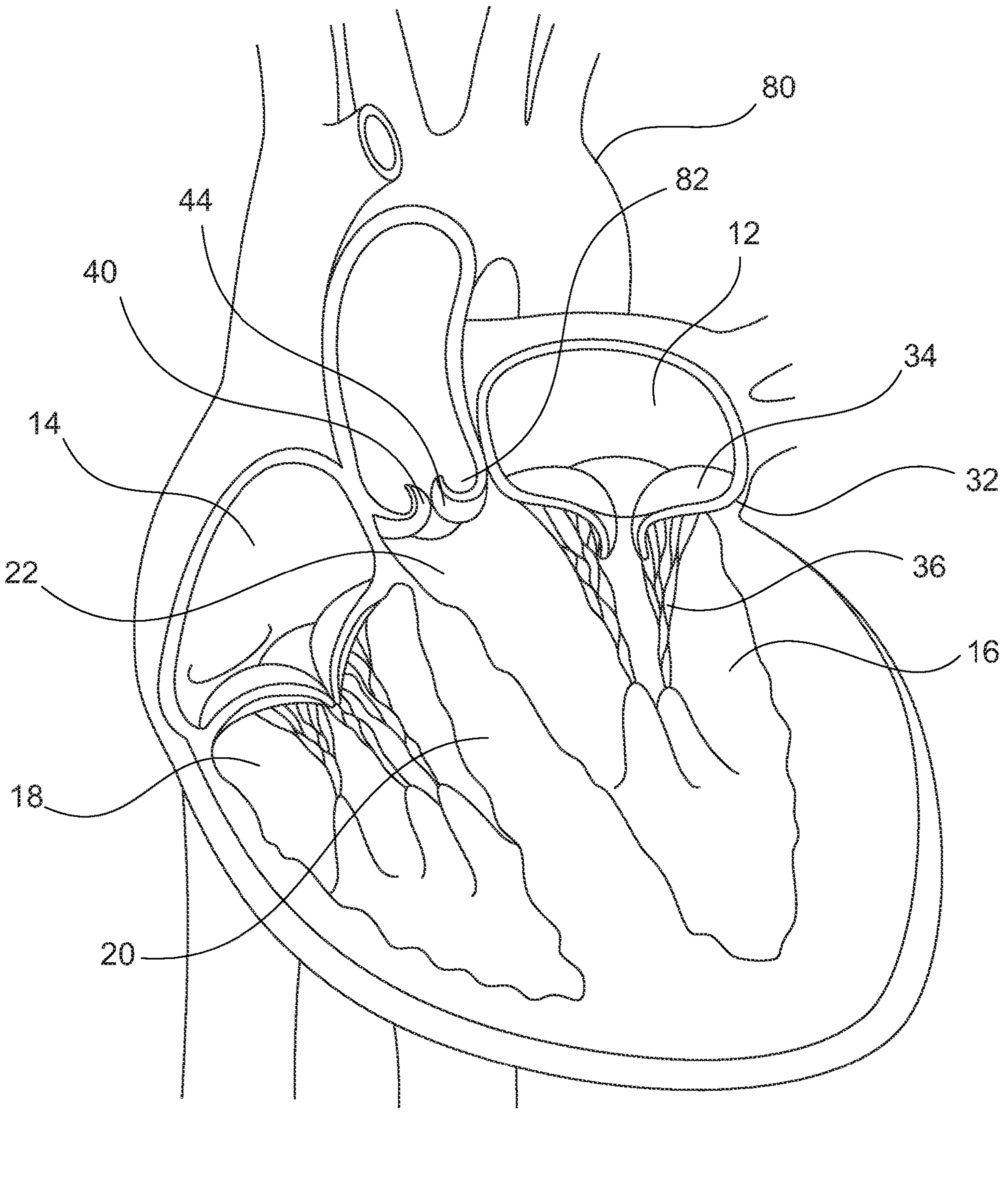
FIG. 1 shows a sectional view of the human heart.

FIG. 1 shows a sectional view of a healthy human heart. The heart has a four-chambered conical structure that includes the left atrium 12, the right atrium 14, the left ventricle 16 and the right ventricle 18. The wall separating between the left and right sides of the heart is referred to as the septum 20. The native mitral valve 30 is positioned between the left atrium 12 and the left ventricle 16. The native aortic valve 40 is positioned between the left ventricle 16 and the aorta 80. The initial portion of the aorta 80 extending from the native aortic valve 40 is the aortic root 82, and the adjoining part of the left ventricle 16 is the left ventricular outflow tract (LVOT) 22.

The native mitral valve 30 comprises a mitral annulus 32 and a pair of mitral leaflets 34 extending downward from the annulus 32. When operating properly, the leaflets 34 function together to allow blood flow only from the left atrium 12 to the left ventricle 14. Specifically, during diastole, when the muscles of the left atrium 12 and the left ventricle 16 dilate, oxygenated blood flows from the left atrium 12, through the mitral valve 30, into the left ventricle 16. During systole, when the muscles of the left atrium 12 relax and the left ventricle 16 contacts, the blood pressure within the left ventricle 16 increases so as to urge to two mitral leaflets 34 to coapt, thereby preventing blood flow from the left ventricle 16 back to the left atrium 12. A plurality of fiber cords, referred to as the chordae tendinae 36, tether the mitral leaflets 34 to papillary muscles of the left ventricle 16 to prevent them from prolapsing under pressure and folding back through the mitral annulus 32.

The term "plurality", as used herein, means more than one.

The native aortic valve 40 comprises an aortic annulus 42 and three aortic leaflets 44 extending upward (toward the aortic root 82) from the annulus 42. During systole, blood is expelled from the left ventricle 16, through the aortic valve 40, into the aorta 80. When either the native mitral valve 30 or native aortic valve 40 fails to function properly, a prosthetic replacement valve 120 can help restore functionality.

Figure 2:
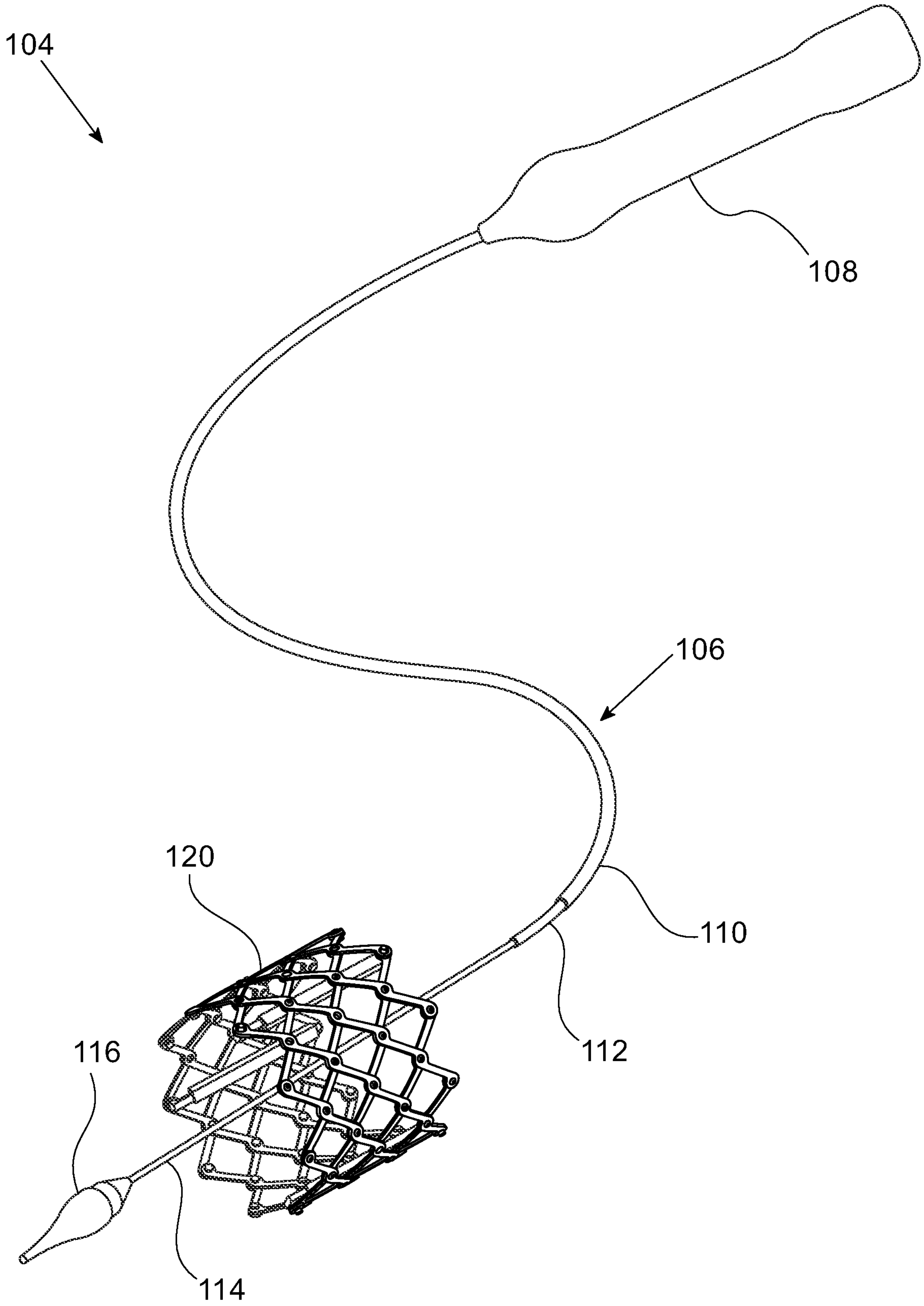
FIG. 2 shows a view in perspective of a delivery assembly comprising a delivery apparatus carrying a prosthetic valve, according to some embodiments.

FIG. 2 shows a view in perspective of a delivery assembly 104, according to some embodiments. The delivery assembly 104 can include a prosthetic valve 120 and a delivery apparatus 106. The prosthetic valve 120 can be on or releasably coupled to the delivery apparatus 106. The delivery apparatus can include a handle 108 at a proximal end thereof, a nosecone shaft 114 extending distally from the handle 108, a nosecone 116 attached to the distal portion of the nosecone shaft 114, a delivery shaft 112 extending over the nosecone shaft 114, and optionally an outer shaft 110 extending over the delivery shaft 112.

The term "proximal", as used herein, generally refers to the side or end of any device or a component of a device, which is closer to the handle 108 or an operator of the handle 108 when in use.

The term "distal", as used herein, generally refers to the side or end of any device or a component of a device, which is farther from the handle 108 or an operator of the handle 108 when in use.

The term "prosthetic valve", as used herein, refers to any type of a prosthetic valve which may be either surgically implantable, or deliverable to a patient's target site over a catheter. A catheter deliverable prosthetic valve 120 is radially expandable and compressible between a radially compressed, or crimped, state, and a radially expanded state. Thus, a prosthetic valve 120 can be crimped or retained by a delivery apparatus 106 in a compressed state during delivery, and then expanded to the expanded state once the prosthetic valve 120 reaches the implantation site. The expanded state may include a range of diameters to which the valve may expand, between the compressed state and a maximal diameter reached at a fully expanded state. Thus, a plurality of partially expanded states may relate to any expansion diameter between radially compressed or crimped state, and maximally expanded state.

A prosthetic valve of the current disclosure may include any prosthetic valve configured to be mounted within the native aortic valve, the native mitral valve, the native pulmonary valve, and the native tricuspid valve.

A catheter deliverable prosthetic valve 120 can be delivered to the site of implantation via a delivery assembly 104 carrying the valve 120 in a radially compressed or crimped state, toward the target site, to be mounted against the native anatomy, by expanding the valve 120 via various expansion mechanisms. Balloon expandable valves generally involve a procedure of inflating a balloon within a prosthetic valve, thereby expanding the prosthetic valve 120 within the desired implantation site. Once the valve is sufficiently expanded, the balloon is deflated and retrieved along with the delivery apparatus 106. Self-expandable valves include a frame that is shape-set to automatically expand as soon an outer retaining capsule, which may be also defined as the distal portion of an outer shaft 110 or the distal portion of a delivery shaft 112, is withdrawn proximally relative to the prosthetic valve. Mechanically expandable valves are a category of prosthetic valves that rely on a mechanical actuation mechanism for expansion. The mechanical actuation mechanism usually includes a plurality of actuator assemblies, releasably coupled to respective actuation arm assemblies of the delivery apparatus 106, controlled via the handle 108 for actuating the actuator assemblies to expand the prosthetic valve to a desired diameter. The actuator assemblies may optionally lock the valve's position to prevent undesired recompression thereof, and disconnection of the actuation arm assemblies from the actuator assemblies, to enable retrieval of the delivery apparatus 106 once the prosthetic valve is properly positioned at the desired site of implantation.

The delivery assembly 104 can be utilized, for example, to deliver a prosthetic aortic valve for mounting against the aortic annulus 42, to deliver a prosthetic mitral valve for mounting against the mitral annulus 32, or to deliver a prosthetic valve for mounting against any other native annulus.

The outer shaft 110 and the delivery shaft 112 can be configured to be axially movable relative to each other, such that a proximally oriented movement of the outer shaft 110 relative to the delivery shaft 112, or a distally oriented movement of the delivery shaft 112 relative to the outer shaft 110, can expose the prosthetic valve 120 from the outer shaft 110. In alternative embodiments, the prosthetic valve 120 is not housed within the outer shaft 110 during delivery. Thus, according to some embodiments, the delivery apparatus 106 does not include an outer shaft 110.

As mentioned above, the proximal ends of the nosecone shaft 114, the delivery shaft 112, components of the actuation arm assemblies (in case of mechanically expandable vales), and when present—the outer shaft 110, can be coupled to the handle 108. During delivery of the prosthetic valve 120, the handle 108 can be maneuvered by an operator (e.g., a clinician or a surgeon) to axially advance or retract components of the delivery apparatus 106, such as the nosecone shaft 114, the delivery shaft 112, and/or the outer shaft 110, through the patient's vasculature, as well as to expand or contract a mechanically expandable valve 120', for example by maneuvering the actuation arm assemblies, and to disconnect the prosthetic valve 120 from the delivery apparatus 106, for example—by decoupling the actuation arm assemblies from the actuator assemblies of mechanically expandable valve, in order to retract the delivery apparatus 106 once the prosthetic valve is mounted in the implantation site.

According to some embodiments, the handle 108 can include one or more operating interfaces, such as steerable or rotatable adjustment knobs, levers, sliders, buttons (not shown) and other actuating mechanisms, which are operatively connected to different components of the delivery apparatus 106 and configured to produce axial movement of the delivery apparatus 106 in the proximal and distal directions, as well as to expand or contract the prosthetic valve 120 via various adjustment and activation mechanisms.

Figure 3B:
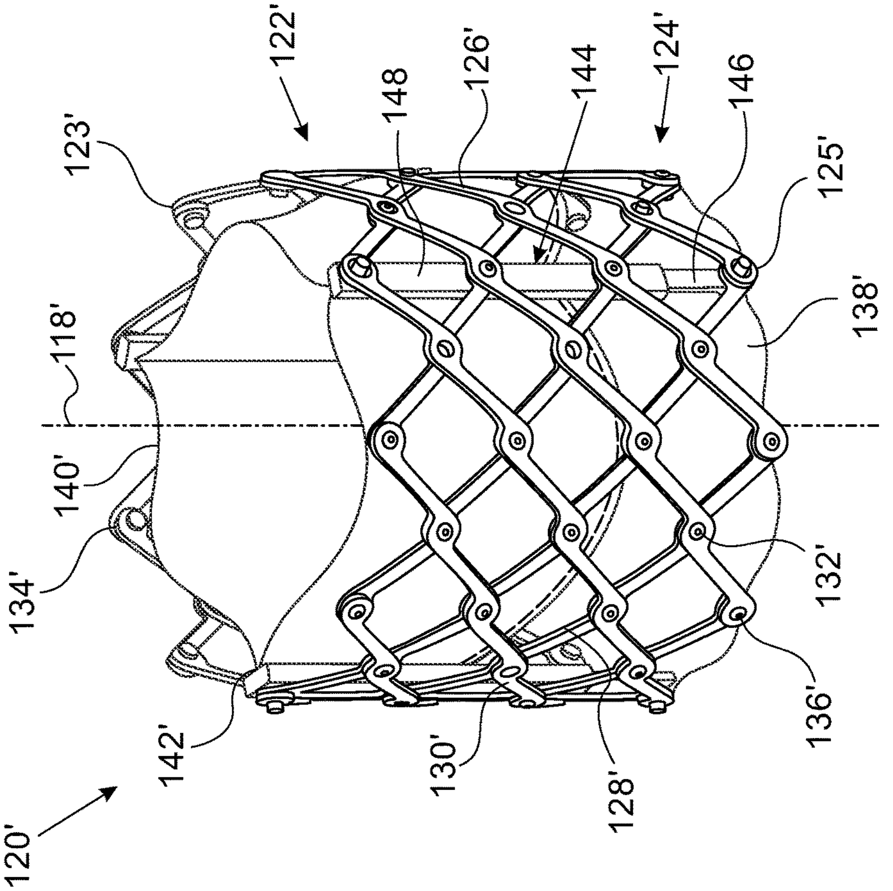
FIG. 3B shows a view in perspective of a prosthetic mechanical valve, according to some embodiments.
Figure 3A:
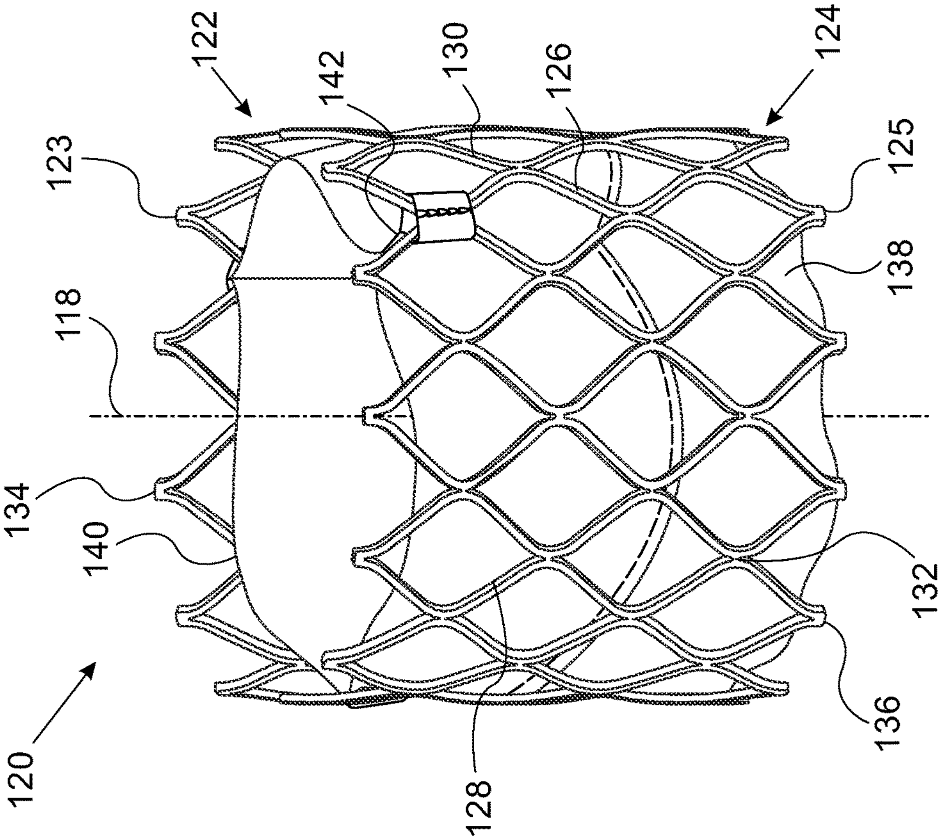
FIG. 3A shows a view in perspective of a prosthetic valve, according to some embodiments.

FIG. 3A shows an exemplary prosthetic valve 120 in an expanded state, according to some embodiments. The prosthetic valve 120 can comprise an inflow end portion 124 defining an inflow end 125, and an outflow end portion 122 defining an outflow end 123. The prosthetic valve 120 can define a valve longitudinal axis 118 extending through the inflow end portion 124 and the outflow end portion 122. In some instances, the outflow end 123 is the distal end of the prosthetic valve 120, and the inflow end 125 is the proximal end of the prosthetic valve 120. Alternatively, depending for example on the delivery approach of the valve, the outflow end can be the proximal end of the prosthetic valve, and the inflow end can be the distal end of the prosthetic valve.

The term "outflow", as used herein, refers to a region of the prosthetic valve through which the blood flows through and out of the valve 120, for example between the valve longitudinal axis 118 and the outflow end 123.

The term "inflow", as used herein, refers to a region of the prosthetic valve through which the blood flows into the valve 120, for example between inflow end 125 and the valve longitudinal axis 118.

The valve 120 comprises a frame 126 composed of interconnected struts 130. The frame can be made of various suitable materials, including plastically-expandable materials such as, but not limited to, stainless steel, a nickel based alloy (e.g., a cobalt-chromium or a nickel-cobalt-chromium alloy such as MP35N alloy), polymers, or combinations thereof. When constructed of a plastically-expandable materials, the frame 126 (and thus the prosthetic valve 120) can be crimped to a radially compressed state on a delivery shaft 112, and then expanded inside a patient by an inflatable balloon or equivalent expansion mechanism. Alternatively or additionally, the frame 126 can be made of self-expanding materials such as, but not limited to, nickel titanium alloy (e.g., Nitinol). When constructed of a self-expandable material, the frame 126 (and thus the prosthetic valve 120) can be crimped to a radially compressed state and restrained in the compressed state by insertion into a shaft or equivalent mechanism of a delivery apparatus 106.

In the exemplary embodiment shown in FIG. 3A, the end portions of the struts 130 are forming apices 134 at the outflow end 123 and apices 136 at the inflow end 125. The struts 130 can be interconnected with each other at additional junctions 132 formed between the outflow apices 134 and the inflow apices 136. The junctions 132 can be equally or unequally spaced apart from each other, and/or from the apices 134, 136, between the outflow end 123 and the inflow end 125. The struts 130 collectively define a plurality of open cells 128 of the frame 126. According to some embodiments, as shown in the exemplary embodiments of FIG. 3A, the struts 130 may be formed with alternating bends that may be welded or otherwise secured to each other at junctions 132.

A prosthetic valve 120 further comprises a plurality of leaflets 140 (e.g., three leaflets), positioned at least partially within the frame 126, and configured to regulate flow of blood through the prosthetic valve 120 from the inflow end 125 to the outflow end 123. While three leaflets 140 arranged to collapse in a tricuspid arrangement, are shown in the exemplary embodiment illustrated in FIG. 3A, it will be clear that a prosthetic valve 120 can include any other number of leaflets 140. The leaflets 140 are made of a flexible material, derived from biological materials (e.g., bovine pericardium or pericardium from other sources), bio-compatible synthetic materials, or other suitable materials. The leaflets may be coupled to the frame 126 via commissures 142, either directly or attached to other structural elements connected to the frame 126 or embedded therein, such as commissure posts. The leaflets 140 define a non-planar coaptation plane (not annotated) when they coapt with each other to seal blood flow through the prosthetic valve 120. Further details regarding prosthetic valves, including the manner in which leaflets may be mounted to their frames, are described in U.S. Pat. Nos. 6,730,118, 7,393,360, 7,510,575, 7,993,394 and 8,252,202, and U.S. Patent Application No. 62/614,299, all of which are incorporated herein by reference.

According to some embodiments, the prosthetic valve 120 may further comprise at least one skirt or sealing member, such as the inner skirt 138 shown in the exemplary embodiment illustrated in FIG. 3A. The inner skirt 138 can be mounted on the inner surface of the frame 126, configured to function, for example, as a sealing member to prevent or decrease perivalvular leakage. The inner skirt 138 can further function as an anchoring region for the leaflets 140 to the frame 126, and/or function to protect the leaflets 140 against damage which may be caused by contact with the frame 126, for example during valve crimping or during working cycles of the prosthetic valve 120. Additionally, or alternatively, the prosthetic valve 120 can comprise an outer skirt (not shown) mounted on the outer surface of the frame 126, configure to function, for example, as a sealing member retained between the frame 126 and the surrounding tissue of the native annulus against which the prosthetic valve 120 is mounted, thereby reducing risk of paravalvular leakage past the prosthetic valve 120. Any of the inner skirt 138 and/or outer skirt can be made of various suitable biocompatible materials, such as, but not limited to, various synthetic materials (e.g., PET) or natural tissue (e.g. pericardial tissue).

FIG. 3B illustrates a mechanically expandable valve 120', which is a specific type of the prosthetic valve 120 described herein above, with like parts having a prime designation. According to some embodiments, the struts 130' are arranged in a lattice-type pattern. In the embodiment illustrated in FIG. 3B, the struts 130' are positioned diagonally, or offset at an angle relative to, and radially offset from, the valve longitudinal axis 118' when the prosthetic valve 120' is in an expanded position. It will be clear that the struts 130' can be offset by other angles than those shown in FIG. 3B, such as being oriented substantially parallel to the valve longitudinal axis 118'.

According to some embodiments, as further shown in FIG. 3B, the frame 126' may comprise openings or apertures at the regions of apices 134', 136' and junctions 132' of the struts 130'. Respective hinges can be included at locations where the apertures of struts 130' overlap each other, via fasteners, such as rivets or pins, which extend through the apertures. The hinges can allow the struts 130' to pivot relative to one another as the frame 126' is radially expanded or compressed.

In alternative embodiments, the struts are not coupled to each other via respective hinges, but are otherwise pivotable or bendable relative to each other, so as to permit frame expansion or compression. For example, the frame can be formed from a single piece of material, such as a metal tube, via various processes such as, but not limited to, laser cutting, electroforming, and/or physical vapor deposition, while retaining the ability to collapse/expand radially in the absence of hinges and like.

According to some embodiments, a mechanically expandable valve 120' comprises a plurality of actuator assemblies 144, configured to facilitate expansion of the valve 120, and in some instances, to lock the valve 120' at an expanded state, preventing unintentional recompression thereof. Although FIG. 3B illustrates three actuator assemblies 144, mounted to, and equally spaced around, an inner surface of the frame 126, it should be clear that a different number of actuator assemblies 144 may be utilized, that the actuator assemblies 144 can be mounted to the frame 126 around its outer surface, and that the circumferential spacing between actuator assemblies 144 can be unequal.

While specific examples of prosthetic valves 120 and 120' are illustrated in FIGS. 3A and 3B, respectively, it will be understood that a prosthetic valve 120 can take many other forms known in the art. Any reference to a prosthetic valve 120 throughout the current disclosure, relates to any type of a prosthetic valve, including the embodiment of the prosthetic valve 120 illustrated in FIG. 3A and the embodiment of a mechanically expandable valve 120' illustrated in FIG. 3B, unless stated otherwise.

Figure 4A:
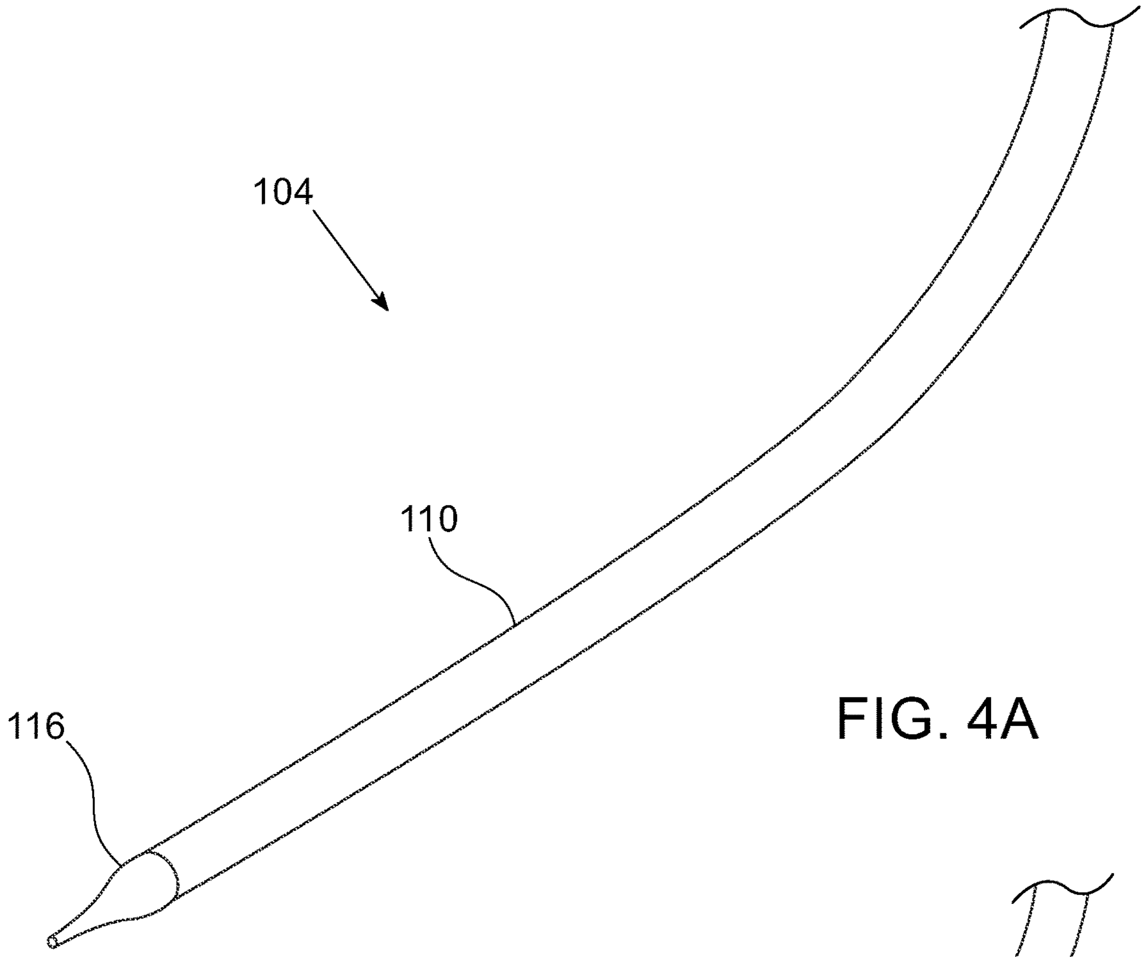
FIGS. 4A-4C show different stages of prosthetic valve deployment, according to some embodiments.
Figure 4B:
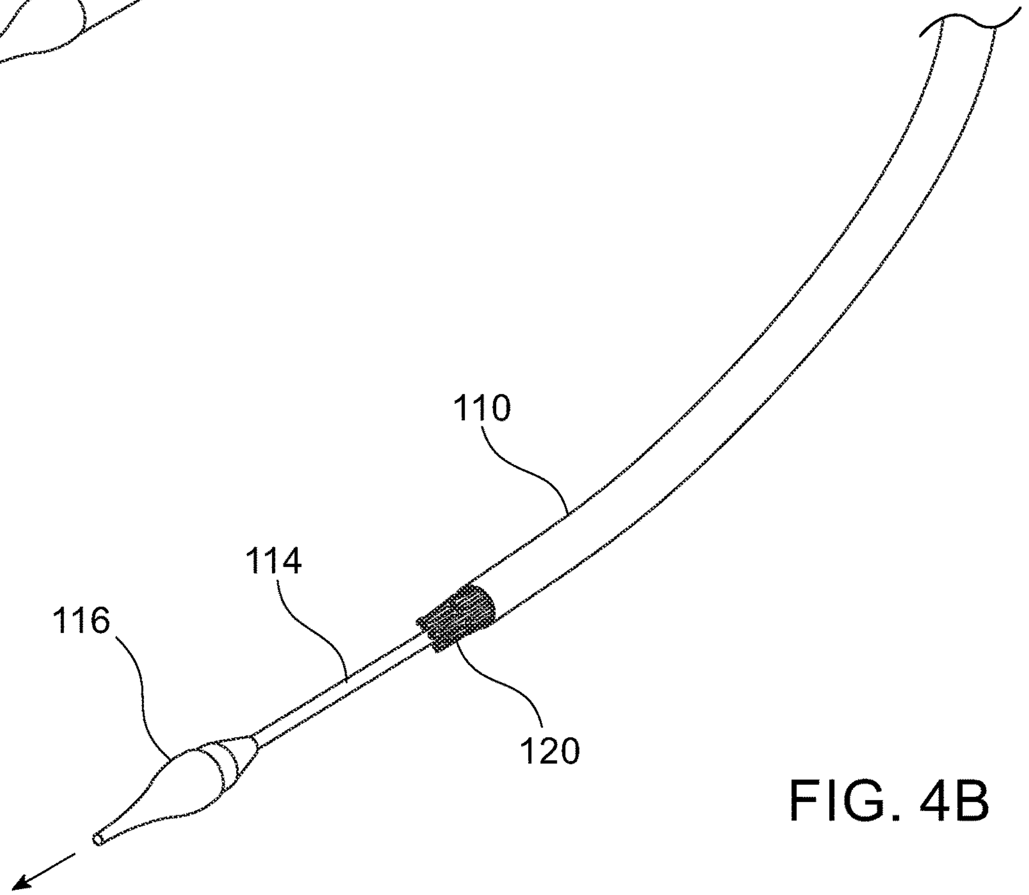
Figure 4C:
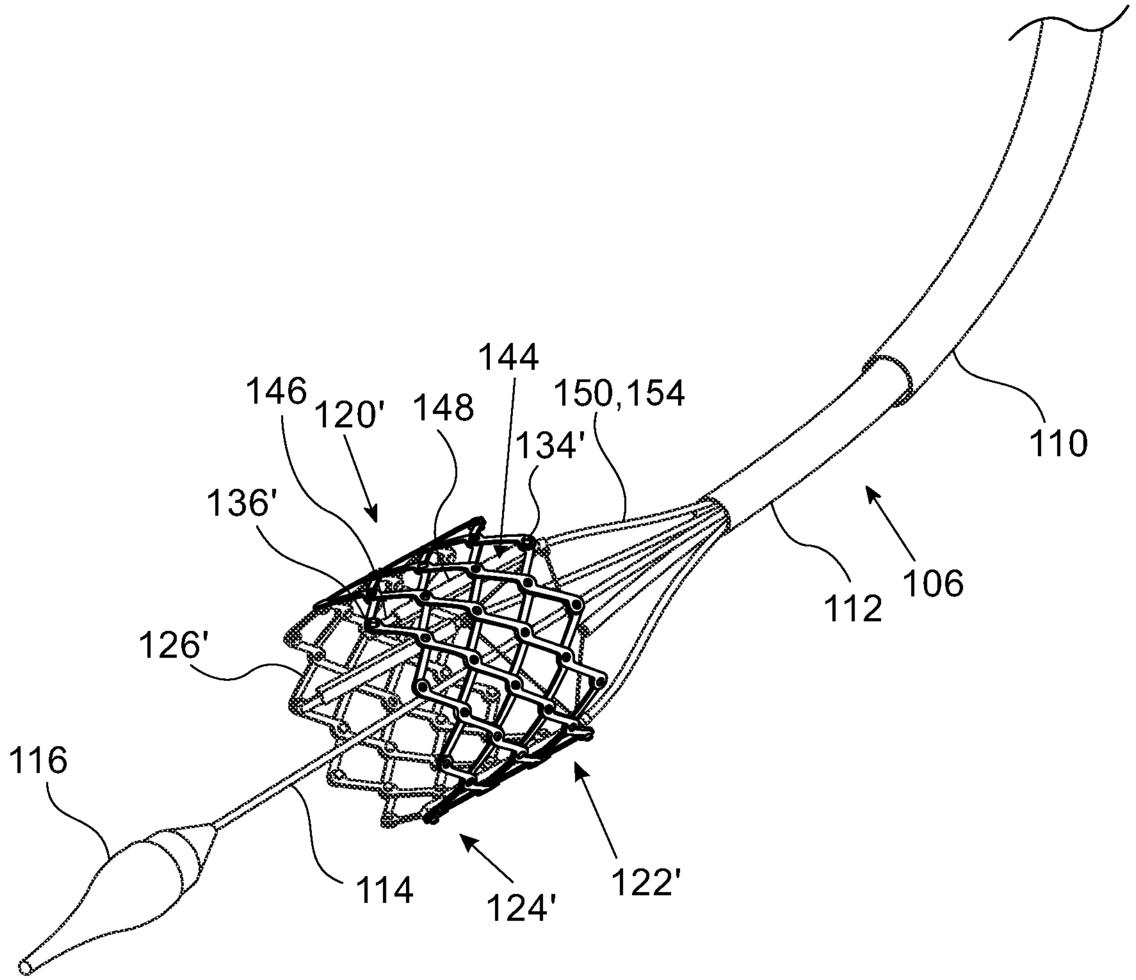

FIGS. 4A-4C show the distal portion of the delivery assembly 104 at different phases of a prosthetic valve 120 delivery and expansion procedure. Prior to implantation, the prosthetic valve 120 can be crimped onto the delivery apparatus 106. This step can include placement of the radially compressed valve 120' within the outer shaft 110. A distal end portion of the outer shaft 110 can extend over the prosthetic valve 120 and contact the nosecone 116 in a delivery configuration of the delivery apparatus 106. Thus, the distal end portion of the outer shaft 110 can serve as a delivery capsule that contains, or houses, the prosthetic valve 120 in a radially compressed or crimped configuration for delivery through the patient's vasculature. FIG. 4A shows an exemplary embodiment of a distal portion of the outer shaft 110 extending over a crimped prosthetic valve (hidden from view), having its distal lip pressed against the nosecone 116.

The outer shaft 110 and the delivery shaft 112 can be configured to be axially movable relative to each other, such that a proximally oriented movement of the outer shaft 110 relative to the delivery shaft 112, or a distally oriented movement of the delivery shaft 112 relative to the outer shaft 110, can expose the prosthetic valve 120 from the outer shaft 110 as shown in FIG. 4B. In alternative embodiments, the prosthetic valve 120 is not housed within the outer shaft 110 during delivery. Thus, according to some embodiments, the delivery apparatus 106 does not include an outer shaft 110.

According to some embodiments, the prosthetic valve 120 is a mechanically expandable valve 120', comprising a plurality of actuator assemblies 144 secured to a frame 126, and configured to radially expand and/or compress the frame 126 via appropriate actuation control mechanisms operable by the handle 108.

FIG. 4C shows an exemplary mechanically expandable valve 120' in an expanded state, wherein the delivery apparatus 106 further comprises a plurality of actuation arm assemblies 150 extending from the handle 108 through the delivery shaft 112. The actuation arm assemblies 150 can generally include actuation members (hidden from view) releasably coupled at their distal ends to respective actuator assemblies 144, and support sleeves disposed around the respective actuation members. Each actuation member may be axially movable relative to the support sleeve covering it. Unless stated otherwise, the leaflets 132, 132' and skirt 136, 136' are omitted from view throughout the figures, for purposes of clarity.

According to some embodiments, each actuator assembly 144 comprises an inner member 146 that may partially extend through a lumen of an outer member 148. The inner member can be attached to the frame 126' at one end thereof, such as an inflow apex 136' or another junction 132' along the inflow end portion 124'. The outer member can be attached to the frame 126' at an opposite end thereof, such as an outflow apex 134' or another junction 132' along the outflow end portion 122'.

According to some embodiments, the actuation arm assemblies 150 are configured to releasably couple to the prosthetic valve 120', and to move the prosthetic valve 120' between the radially compressed and the radially expanded states. For example, the actuation member of the actuation arm assemblies 150 can be threadedly attached at its distal end, to a receiving threaded bore at the proximal end of the inner member 146. The distal edge of the support sleeve, covering the actuation member, can abut or engage the proximal end of the outer member 148, so as to prevent the outer member 148 from moving proximally beyond the support sleeve.

In order to radially expand the frame 126', and therefore the prosthetic valve 120', the support sleeve can be held firmly against the outer member 148. The actuation member 154 can then be pulled in a proximally oriented direction. Because the support sleeve is being held against the outer member 148, which is connected to an outflow apex 134', the outflow end 123' of the frame 126' is prevented from moving relative to the support sleeve. As such, movement of the actuation member in a proximally oriented direction can cause movement of the inner member 146 in the same direction, thereby causing the frame 126' to foreshorten axially and expand radially. More specifically, when the inner member 146 is moved axially, for example in a proximally oriented direction, within the outer member 148, the junction 132' to which the inner member 146 is attached, moves there along in the same direction toward the opposite junction, to which the outer member 148 is attached. This, in turn, causes the frame 126' to foreshorten axially and expand radially.

Once the desired diameter of the prosthetic valve 120' is reached, the actuation member may be rotated so as to unscrew it from the inner member 146. This rotation serves to disengage between the distal threaded portion of the actuation member and the threaded bore of the inner member (not shown), enabling the actuation arm assemblies 150 to be pulled away, and retracted, together with the delivery apparatus 106, from the patient's body, leaving the prosthetic valve 120' implanted in the patient.

While radial expansion of the frame 126' is achievable by axially moving the inner member 146 in a proximally oriented direction, relative to the outer member 148, it will be understood that similar frame expansion may be achieved by axially pushing an outer member 148 in a distally oriented direction, relative to an inner member 146. Moreover, while the illustrated embodiment of FIG. 4C shows the outer member 148 affixed to an outflow end portion 122' of the frame 126', and an inner member 146 affixed to an inflow end portion 124' of the frame 126', in alternative embodiments, the outer member 148 may be affixed to the inflow end portion 124' of the frame 126', while the inner member 146 may be affixed to the outflow end portion 122' of the frame 126'.

According to some embodiments, the handle 108 can comprise control mechanisms which may include steerable or rotatable knobs, levers, buttons and such, which are manually controllable by an operator to produce axial and/or rotatable movement of different components of the delivery apparatus 106. For example, the handle 108 may comprise one or more manual control knobs, such as a manually rotatable control knob that is effective to pull the actuation members 154 of the actuation arm assemblies 150 when rotated by the operator.

According to other embodiments, control mechanisms in handle 108 and/or other components of the delivery apparatus 106 can be electrically, pneumatically and/or hydraulically controlled. According to some embodiments, the handle 108 can house one or more electric motors which can be actuated by an operator, such as by pressing a button or switch on the handle 108, to produce movement of components of the delivery apparatus 106. For example, the handle 108 may include one or more motors operable to produce linear movement of components of the actuation arm assemblies 150, and/or one or more motors operable to produce rotational movement of the actuation members to disconnect them from the inner members 146. According to some embodiments, one or more manual or electric control mechanism is configured to produce simultaneous linear and/or rotational movement of all of the actuation members.

While a specific actuation mechanism is described above, other mechanisms may be employed to promote relative movement between inner and outer members of actuation assemblies, for example via threaded or other engagement mechanisms. Further details regarding the structure and operation of mechanically expandable valves and delivery system thereof are described in U.S. Pat. No. 9,827,093, US Patent Application Publication Nos. 2019/0060057, 2018/0153689 and 2018/0344456, and U.S. Patent Application Nos. 62/870,372 and 62/776,348, all of which are incorporated herein by reference.

Prosthetic valve related hemodynamic disturbances may develop over time, post implantation, for example due to inflammatory and other biological processes that may result from valve-tissue or valve-blood-flow interactions. In some cases, thrombus may be formed in regions subjected to low flow or blood stasis, such as the regions bound between the leaflets 140 and the frame 126. Leaflet thrombosis usually occurs in the course of several days post-implantation. Leaflet stenosis is usually a result of an even longer process. Thus, leaflet thrombosis or leaflet calcification detection is a post-procedural process.

According to some embodiments of the invention, there is provided a monitoring apparatus 102 comprising at least one sensor 158 configured to measure a flow characteristic associated with the functioning of a heart valve, such as a prosthetic heart valve 120. According to some embodiments, the at least one sensor 158 is attached to the prosthetic valve 120. According to some embodiments, the at least one sensor 158 is positioned in the vicinity of a heart valve, such as proximal or distal to a native heart valve (e.g., the native aortic valve 40 or the native mitral valve 30), or to a prosthetic heart valve 120. The at least one sensor 158 is configured to generate a signal that is correlated to a physiological flow-related parameter such as blood pressure, blood flow velocity, and/or temperature. According to some embodiments, the at least one sensor 158 is configured to measure the flow characteristic at the heart valve of the patient. The term "at the heart valve", as used herein, means a flow characteristic measured in the vicinity of the heart valve, such as within 10 cm therefrom. As described above, the heart valve can be a native heart valve and/or a prosthetic heart valve 120.

According to some embodiments, there is provided a valve monitoring assembly 100, comprising a monitoring apparatus 102 having at least one component thereof coupled to a prosthetic valve 120, such that the at least one sensor 158 is configured to measure a flow characteristics associated with the functioning of the prosthetic valve 120. According to some embodiments, the at least one sensor 158 can be attached to the inflow end portion 124, to the outflow end portion 122, or to any other region in between. The at least one sensor 158 can be attached to the frame 126, to commissures 142, to actuator assemblies 144, or to any other structural component of the prosthetic valve 120. According to some embodiments, the at least one sensor 158 can be attached to the prosthetic valve 120 by suturing, screwing, clamping, gluing with bio-compatible adhesives, fastening, welding, or any other suitable technique.

According to some embodiments, the at least one sensor 158 can be positioned in the vicinity of the prosthetic valve 120, for example, attached to a tissue in the vicinity of the prosthetic valve 120. The vicinity of the prosthetic valve 120 can be defined, in some examples, as a region distanced no more than 10 cm from the prosthetic valve 120.

The at least one sensor 158 can be oriented radially inward (i.e., toward the valve longitudinal axis 118), to measure one or more types of physiological parameters within the prosthetic valve 120, or oriented radially outward, to measure one or more types of physiological data outside of, or in contact with, the outer surface of the prosthetic valve 120.

Figure 5A:
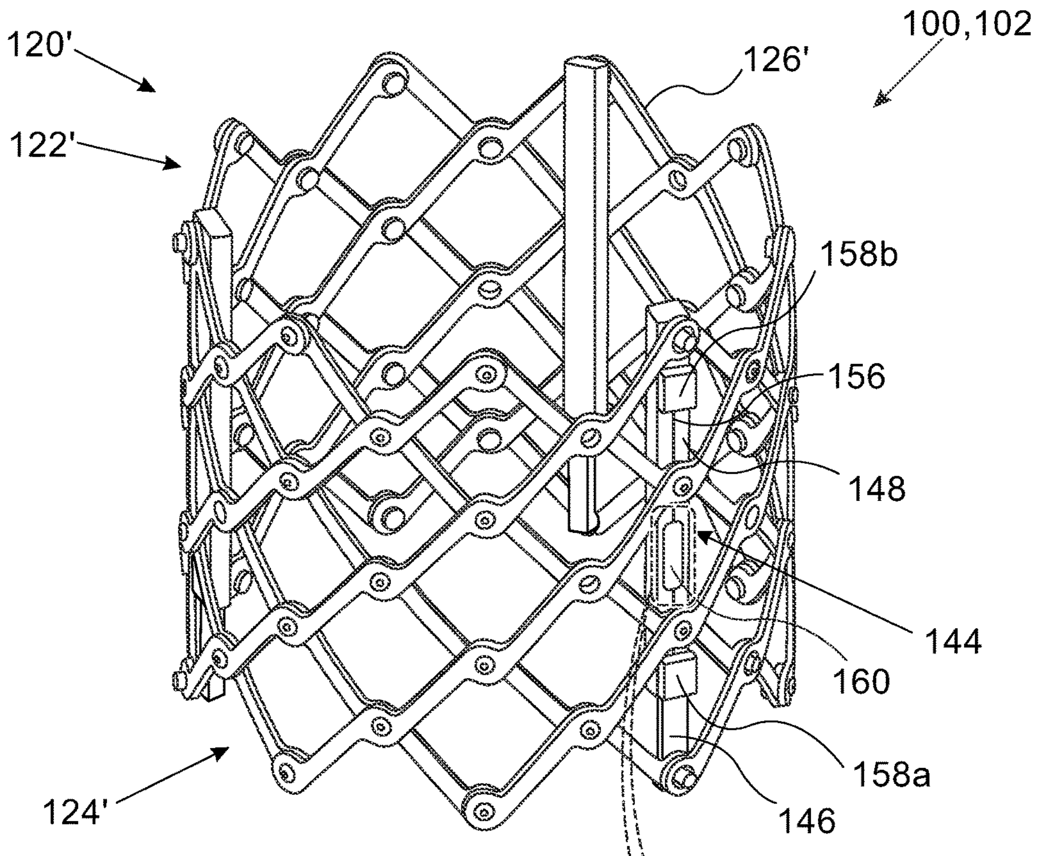
FIG. 5A shows an exemplary configuration of a valve monitoring assembly, according to some embodiments.
Figure 6:
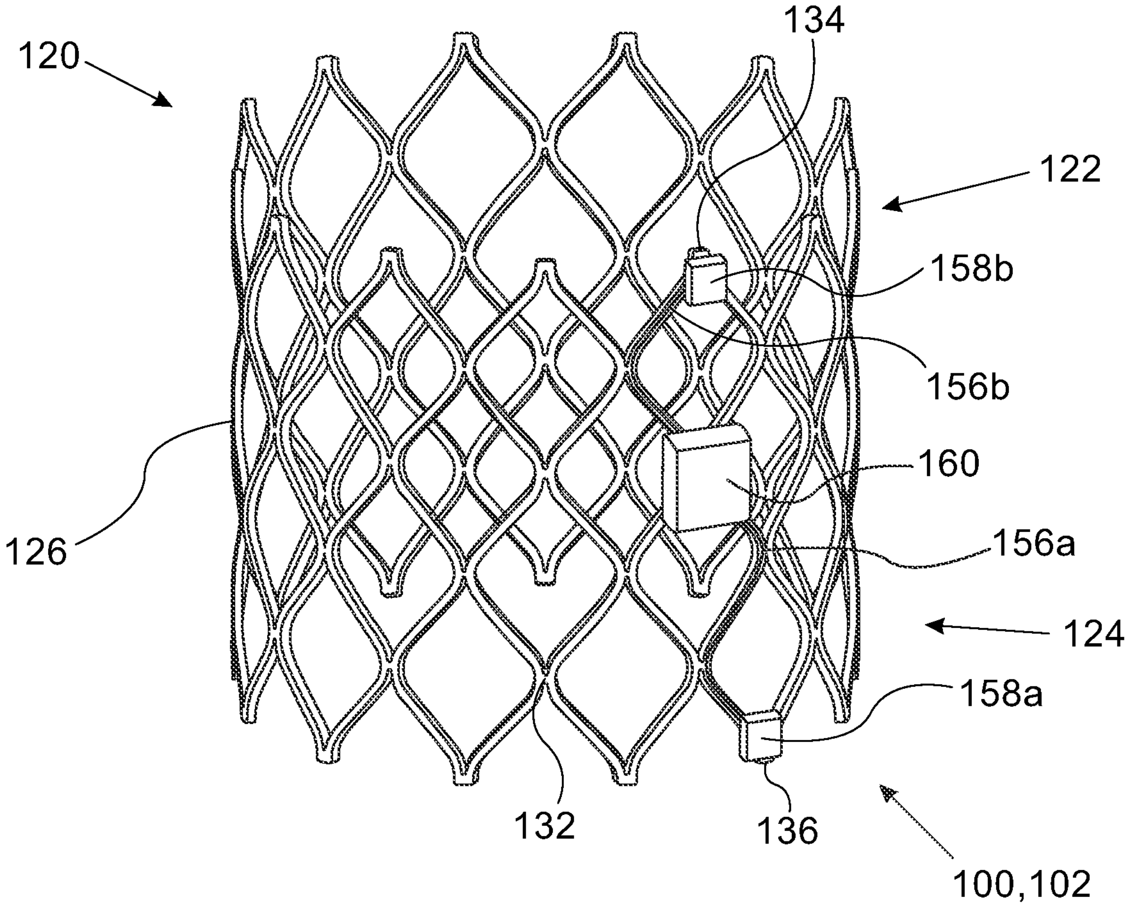
FIG. 6 shows another exemplary configuration of a valve monitoring assembly, according to some embodiments.

According to some embodiments, the prosthetic valve 120 comprises at least two sensors: a first sensor **158*a* and a second sensor 158*b*, attached thereto. FIGS. 5A and 6 show exemplary configurations of a valve monitoring assembly 100 comprising a monitoring apparatus 102 coupled to a prosthetic valve 120' and 120, respectively, with a first sensor 158*a* attached to the inflow end portion 124', 124, and a second sensor 158*b* attached to the outflow end portion 122', 122. Each of the first sensor 158*a* and the second sensor 158*b* may be configured to measure a physiological flow-related property, also termed a "flow characteristic". The flow characteristic may be blood flow, blood pressure, and/or temperature. According to some embodiments, the first sensor 158*a* and the second sensor 158*b* are pressure sensors. According to some embodiments, the first sensor 158*a* and the second sensor 158*b* are flow sensors, configured to measure the flow rate of blood. According to some embodiments, the first sensor 158*a* and the second sensor 158*b*** are temperature sensors.

FIG. 5A shows an exemplary embodiment of a first sensor **158*a* and a second sensor 158*b* attached to a mechanically-expandable valve 120', and more specifically, attached to at least one actuator assembly 144 of the prosthetic valve 120'. In the illustrated example, both the first sensor 158*a* and a second sensor 158*b* are axially spaced apart, attached to the same outer member 148. Alternatively, or additionally, each of the first 158*a* and/or the second 158*b* sensors can be attached to other components of the actuator assembly 144 (e.g., the inner member 146), attached to different actuator assemblies 144, or attached to any other component of the prosthetic valve 120'**.

According to some embodiments, any sensor 158, such as the first or second sensors **158*a* and 158*b***, respectively, includes radiopaque markings that may provide a visible indication of the location of the sensors when viewed under fluoroscopy.

FIG. 6 shows an exemplary embodiment of a first sensor **158*a* and a second sensor 158*b* attached to the frame 126 of a prosthetic valve 120, and more specifically, attached to junctions 132 of the prosthetic valve 120. In the illustrated example, the first sensor 158*a* and a second sensor 158*b* are axially spaced apart, attached to an inflow apex 136 and an outflow apex 134, respectively. Alternatively, or additionally, each of the first 158*a* and/or the second 158*b* sensors can be attached to other junctions 132 or to any other component of the prosthetic valve 120**.

According to some embodiments, the at least one sensor 158 is a flow sensor, configured to provide flow measurement signals that can be compared to absolute threshold values.

According to some embodiments, the at least one sensor 158 is a pressure sensor, configured to provide pressure measurement signals that can be associated with flow values, and can be compared to absolute threshold values. Pressure sensors 158 can sense pressure variations associated with the change in flow velocity. Without being bound by any theory or mechanism of action, such measurement may be based on Bernoulli's principle, namely, an increase in the speed of a fluid can occur simultaneously with a decrease in pressure.

According to some embodiments, any of the first and second sensors **158*a* and 158*b*, respectively, may be piezo-resistive pressure sensors, such as MEMS piezo-resistive pressure sensors. According to other embodiments, any of the first and second sensors 158***a* and 158*b*, respectively, may be capacitive pressure sensors, such as MEMS capacitive pressure sensors.

According to some embodiments, readings from different sensors 158 can be compared with each other to detect regions in which the flow or pressure is disturbed relative to other regions or to detect regions susceptible to such disturbances.

According to some embodiments, the at least one sensor 158, and preferably a plurality of sensors such as the sensors 158*a*, 158*b* shown in FIGS. 5A and 6, are fiber optic sensors, such as fiber optic pressure sensors.

According to some embodiments, at least one flow or pressure sensor 158, and preferably a plurality of flow or pressure sensors 158, are attached to the prosthetic valve 120 and configured to detect central leak, and/or paravalvular regurgitation, of the prosthetic valve 120.

According to some embodiments, temperature may be measured periodically or continuously by at least one temperature sensor 158 to detect potential rise in measured temperature values over time, in order to monitor inflammation development.

Advantageously, post-procedural readings from temperature sensors 158 (one or more) may assist in determining the type of recommended anti-inflammatory therapy. Moreover, it is possible to follow up and obtain temperature readings during the anti-inflammatory therapy, to observe treatment effectiveness and/or determine whether treatment modification is required.

Positioning and orientation of the at least one sensor 158 depends on the type of sensor and its application. For example, while both sensors 158*a* and 158*b* are shown to be attached to the outer surface of the prosthetic valve 120' and 120 in FIGS. 5A and 6, respectively, protruding radially outward, it may be desirable to position the sensors 158 oriented radially inward, if the sensors are flow or pressure sensors, so as to allow meaningful readings to be acquired thereby, without interferences from the surrounding native tissue.

If the sensors 158 are temperature sensors, it may be desirable to orient them radially outward, as shown in the exemplary embodiments illustrated in FIGS. 5A and 6, so as to contact and measure surrounding tissue temperature.

Alternatively or additionally, at least one temperature sensor 158 can be oriented radially inward, so as to measure blood temperature which may be elevated in close proximity to inflamed tissues. Similarly, at least one flow or pressure sensor may be oriented radially outward, at regions which are not necessarily contacted by the annulus or blood vessel wall, so as to measure hemodynamic parameters around the prosthetic valve 120, for example to detect paravalvular leakage.

Figure 5B:
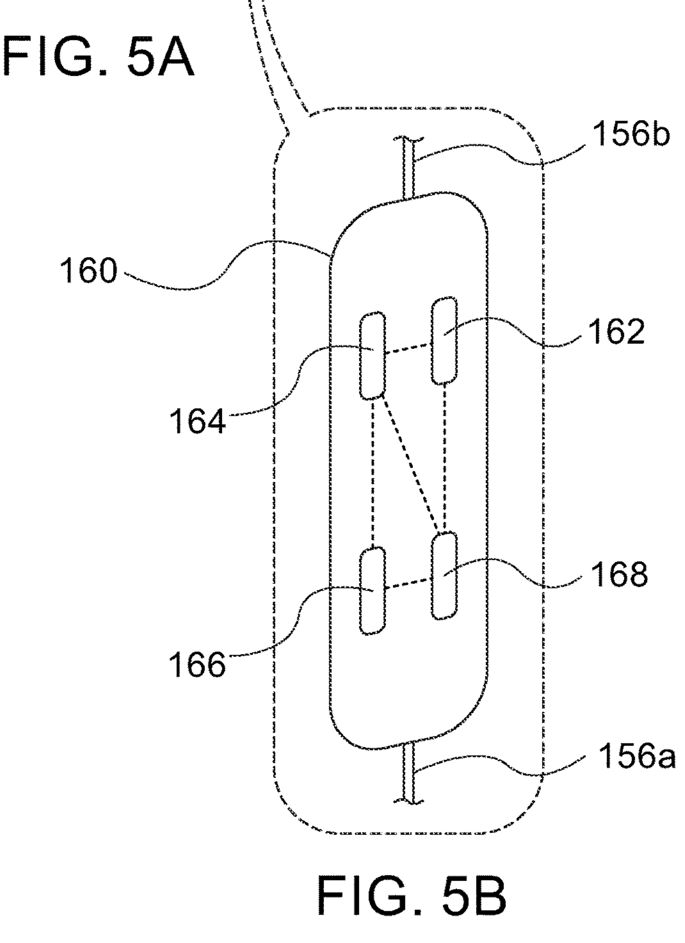
FIG. 5B schematically shows components of a control circuitry, according to some embodiments.

According to some embodiments, a monitoring apparatus 102 comprises at least one sensor 158, and a control circuitry 160 configured to control operation of the at least one sensor 158. FIGS. 5A and 6 show exemplary embodiments of a control circuitry 160 attached to the valve 120' and 120, respectively. FIG. 5A shows a potential configuration of the control circuitry 160 attached to the actuator assembly 144, for example between the sensors 158*a* and 158*b*. In alternative configurations, the control circuitry 160 may be attached to a different actuator assembly 144 than the one sensors 158*a* and 158*b* are attached to. FIG. 5B schematically shows components of the control circuitry 160 of FIG. 5A. Attachment of a control circuitry 160 to an actuator assembly may be advantageous in some embodiments, due to the relatively larger attachment surface area that may be offered by the actuator assembly 144.

FIG. 6 shows a different configuration, in which the control circuitry 160 may be attached to the frame 126, and more specifically, to strut sections and or junctions 132 thereof. The control circuitry 160 may be shaped to conform to the surface area of the valve component it may attach to. According to some embodiments, the control circuitry 160 may be embedded within a patch or a cuff, attached to or circumscribing at least a portion of the prosthetic valve 120 (embodiments not shown).

According to some embodiments, the control circuitry 160 is connected to the at least one sensor 158 via a corresponding communication channel 156, which may be configured to deliver signals between the control circuitry 160 and the sensor 158. The term "communication channel", as used herein, means a physical path allowing communication therethrough. According to some embodiments, the communication channel can be configured to allow: electrical communication via a conductive material, such as a wire; and/or optical communication, e.g. via an optical fiber. The communication channel 156 can deliver measurement signals from the sensor 158 to the control circuitry 160, and optionally to transmit control signals and/or power to the sensor 158. FIGS. 5A-5B shows one exemplary configuration, wherein the communication channels 156*a* and 156*b* extend between the control circuitry 160 and the sensors 158 along the actuator assembly 144. FIG. 6 shows another exemplary configuration, wherein the communication channels 156*a* and 156*b*, extending between the control circuitry 160 and the sensors 158*a* and 158*b*, respectively, follow the path of the strut portions along the boundaries of cells 128. Extending the communication channels 156 along at least some strut portions that define cell boundaries of cells 128 may be advantageous, since the length of the strut portions remains constant, irrespective of whether the prosthetic valve 120 is crimped or expanded, while the distance between opposing junctions may vary as a factor of the valve's expansion diameter, thereby preventing potential undesirable extension the communication channels 156 if their path would have crossed the open portions of the cells 128.

According to some embodiments, each communication channel 156 may include various electrically conductive materials, such as copper, aluminum, silver, gold, and various alloys such as tentalum/platinum, MP35N and the like. An insulator (not shown) can surround each communication channel 156. The insulator can include various electrically insulating materials, such as electrically insulating polymers.

According to some embodiments, each communication channel 156 may be provided in the form of an optic fiber. Such embodiments are mainly applicable for a monitoring apparatus 102 comprising optic fiber pressure sensor 158.

Although the above has been described in relation to some embodiments where the control circuitry 160 is physically connected to the sensors 158, either directly or indirectly, this is not meant to be limiting in any way. According to some embodiments, the control circuitry 160 can be in communication with the sensors 158 via wireless communication. Particularly, the term "in communication with", as used herein, can include any suitable communication method, including wired or wireless communication. As described above, the communication can be electrical, optical or any other suitable method.

Figure 7:
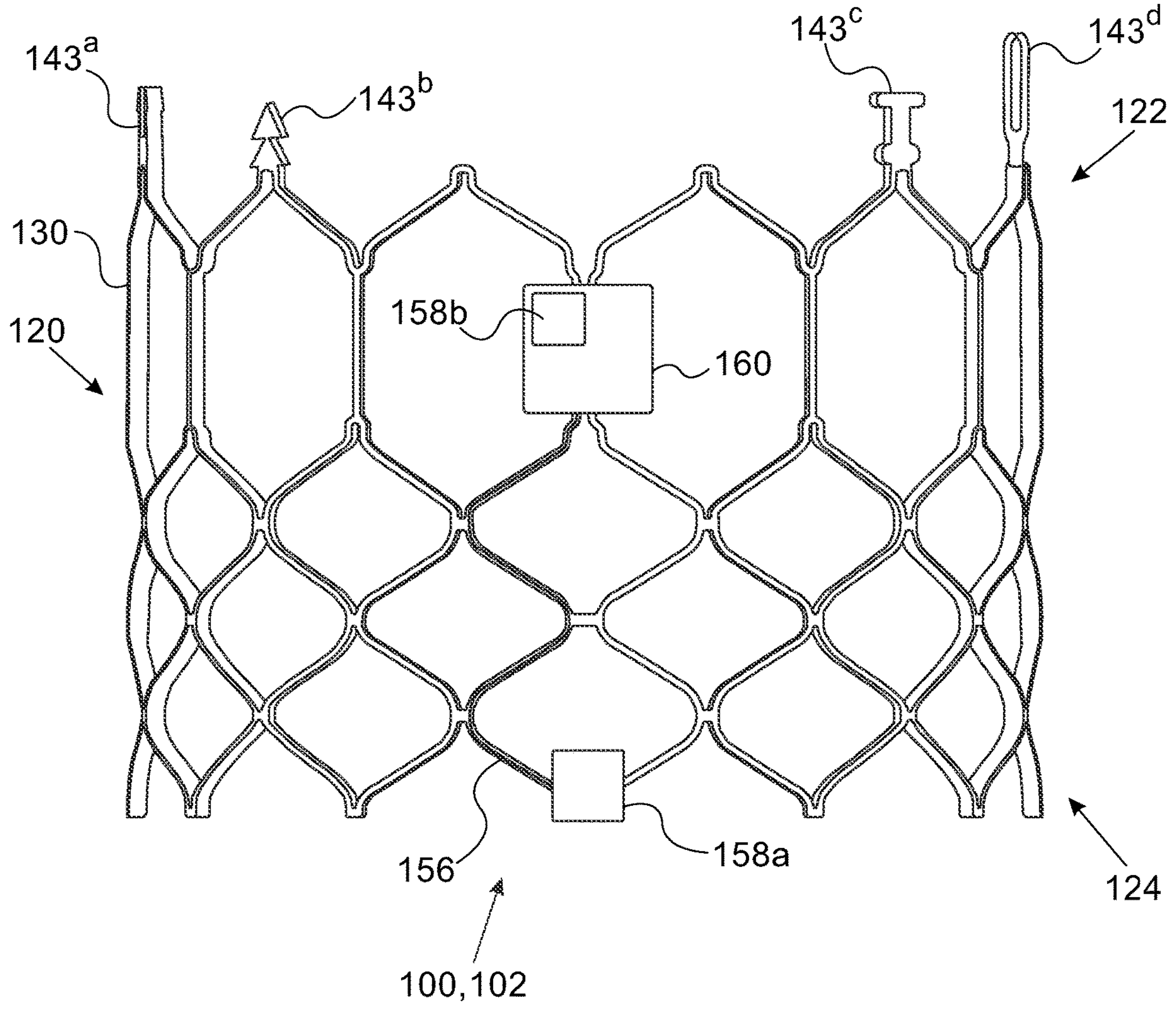
FIG. 7 shows another exemplary configuration of a valve monitoring assembly, according to some embodiments.

According to some embodiments, at least one sensor 158 may be embedded within, or otherwise directly attached to, a control circuitry 160. Alternatively, a control circuitry 160 may be embedded within at least one sensor 158. In one variant of such embodiments, at least one sensor 158 and a control circuitry 160 are directly attached to a common structural platform, such as a patch or a board. FIG. 7 shows an exemplary configuration of a monitoring assembly 100, wherein one sensor 158*a* is attached to one end portion of the frame 126 of a prosthetic valve 120, while another sensor 158*b* is embedded within a control circuitry 160, which is in turn attached to an opposite end portion of the frame 126. While the embodiment illustrated in FIG. 7 shows a sensor 158*b* embedded within the control circuitry 160, which is in turn attached to the outflow end portion, it will be clear that any other combination is contemplated, including the sensor 158*a* embedded within the control panel 160, which in turn may be attached to the inflow end portion 124. Moreover, while the embodiment illustrated in FIG. 7 shows a single sensor 158 embedded within the control circuitry 160, it will be clear that a plurality of sensors 158 may be embedded within, or otherwise directly attached to, the control circuitry 160.

The term "directly attached", as used herein, refers to any form of attachment between components, having the components in physical contact with each other.

The frame 126 of the exemplary prosthetic valve 120 illustrated in FIG. 7 includes a proximal row of cells 128 which are vertically higher than other cell rows. The vertical strut portions of such higher cells 128 may potentially provide larger contact area to support components of a monitoring apparatus 102 attached thereto, such as a control circuitry 160 and/or a sensor 158.

According to some embodiments, the prosthetic valve 120 includes at least one monitoring engagement member 143, configured to engage with at least one component of a monitoring apparatus 102, such as a control circuitry 160 and/or a sensor 158. The term "engage", as used herein, means a physical attachment. According to some embodiments, the at least one monitoring engagement member 143 is rigidly attached to, or integrally formed with, the frame 126 of the prosthetic valve 120.

FIG. 7 shows various available forms of a monitoring engagement member 143. According to some embodiments, a monitoring engagement member 143$^{a}$ may be provided in the form of a snap-fit engagement member, for example provided with resilient extensions configured to be received by and engaged with a component of the monitoring apparatus 102. According to some embodiments, a monitoring engagement member 143$^{b}$ may be provided in the form of a ratchet member, provided with ratcheting teeth configured to engage with complementary teeth of a component of the monitoring apparatus 102. According to some embodiments, a monitoring engagement member 143$^{c}$ may be provided in the form of a snap-fit engagement member, for example provided with a flanged end portion configured to snap into a corresponding recess or opening of a component of the monitoring apparatus 102. According to some embodiments, a monitoring engagement member 143$^{d}$ may be provided in the form of an eyelet configured to engage with a corresponding mating portion of a component of the monitoring apparatus 102.

While four exemplary forms of a monitoring engagement member 143 are shown in FIG. 7, it will be understood that the monitoring engagement member 143 may take any other form known in the art, configured to support engagement of a complementary component therewith. It will be further understood that four different exemplary types of monitoring engagement members 143 are shown in association with the prosthetic valve 120 in FIG. 7 for purposes of illustration only, and that generally a prosthetic valve 120 will include a single type of at least one monitoring engagement members 143. While the embodiment illustrated in FIG. 7 shows the monitoring engagement members 143 extending proximally from the outflow end 123 of the frame 126, it will be clear that other positions are contemplated, such as monitoring engagement members 143 that may extend distally from the inflow end 125 (embodiments not shown).

Advantageously, a prosthetic valve provided with at least one monitoring engagement member 143 may facilitate easier attachment of components of a monitoring apparatus 102, such as sensors 158 or a control circuitry 160, to a prosthetic valve 120 which is already implanted in an annulus. Monitoring engagement members 143 may be similarly employed for convenient assembly of components of a monitoring apparatus 102 with the prosthetic valve 120 prior to implantation.

According to some embodiments, the monitoring apparatus 102 may include local and remote components. A local component of the monitoring apparatus 102 is a component which is attached to the prosthetic valve 120, to a sensor 158, or to a tissue or an organ which is in close proximity (e.g., less than 10 cm.) to the prosthetic valve 120. A remote component of the monitoring apparatus 102 is a component which is implanted within the patient's body, at a remote site (e.g., at a distance of more than 10 cm.) from the prosthetic valve 120. Some components of the monitoring apparatus 102 may be implemented as local components, as remote components, or as a combination of both. Accordingly, the suffix letter "L" will be associated with numerals of local components, and the suffix letter "R" will be associated with numerals of remote components, to avoid confusion. A component appearing without the suffix "L" or "R" will refer to embodiments of the component that may be implemented either as a local component, as a remote component, or as a combination of both.

Figures 8A, 8B, 8C, 8D:
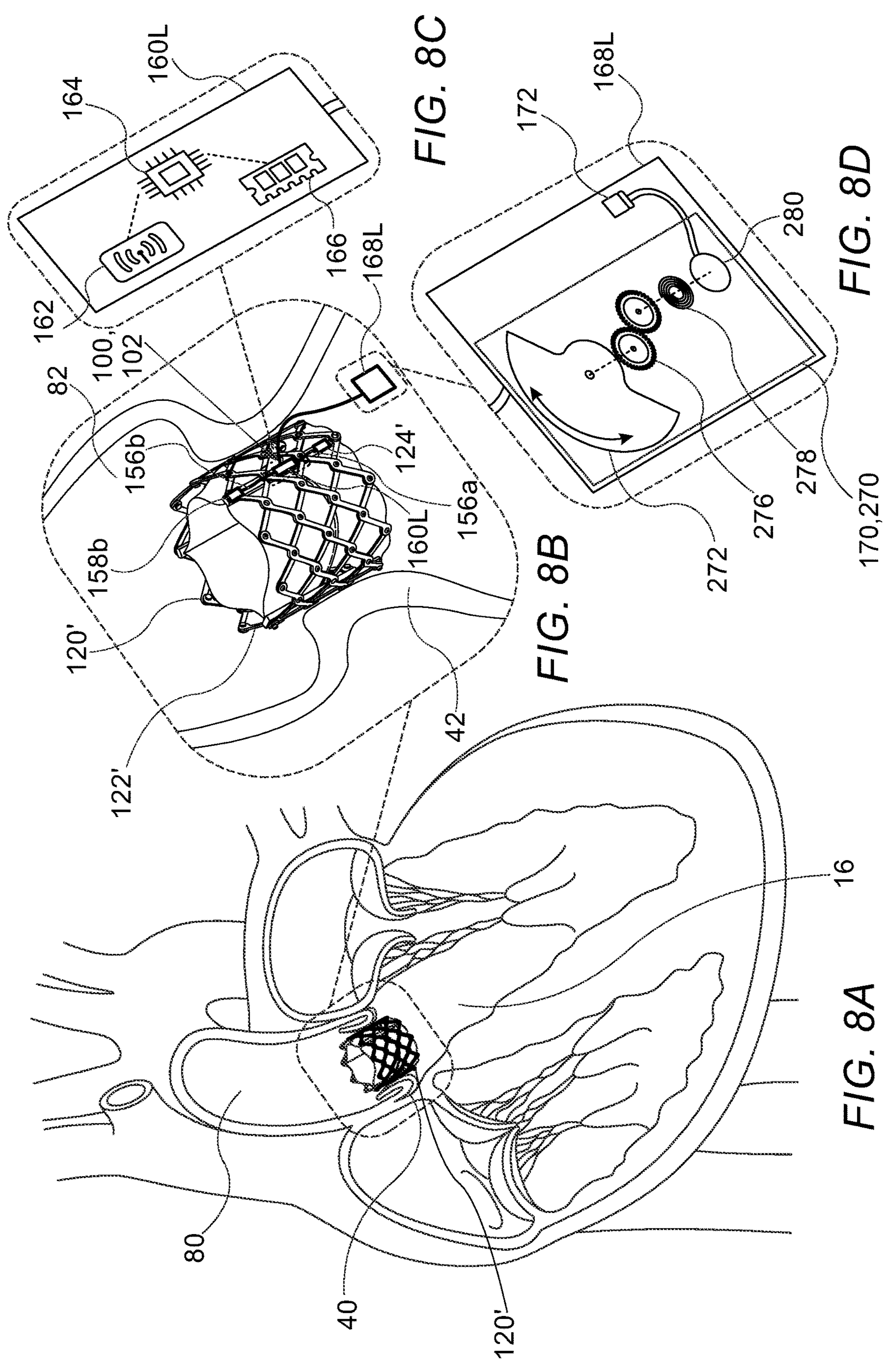
FIGS. 8A-8D show a valve monitoring assembly equipped with a clockwork-type energy harvesting mechanism, according to some embodiments.

According to some embodiments, the control circuitry 160 comprises at least one local control circuitry 160L, as illustrated for example in FIG. 8C. Alternatively or additionally, the monitoring apparatus 102 may comprise a remote control circuitry 160R, as illustrated for example in FIG. 9D. The remote control circuitry 160R may be in communication, either via wired or wireless communication links, with the at least one sensor 158 and/or to the at least one local control circuitry 160L.

According to some embodiments, at least one sensor 158 may be integrated with, or embedded within, the local control circuitry 160L.

According to some embodiments, the monitoring apparatus 102 comprises at least one communication component 162. According to some embodiments, the at least one communication component 162 is in communication with at least one sensor 158, irrespective of whether the monitoring apparatus 102 further comprises a control circuitry 160 or not.

According to some embodiments, the at least one communication component 162 is in communication with the control circuitry 160. According to some embodiments, the control circuitry 160 comprises at least one communication component 162. According to some embodiments, the communication component 162 comprises any one of a local communication component 162L, a remote communication component 162R, or both.

The communication component 162 can comprise a transmitter, a receiver, and/or a transceiver, configured to transmit signals to, and/or receive signals from, devices or components distanced therefrom, including extracorporeal devices. According to some embodiments, the communication component 162 comprises a radiofrequency (RF) transmitter. According to some embodiments, the communication component 162 comprises an antenna.

According to some embodiments, each sensor 158 is in communication with the communication component 162 (see FIG. 5B). In one variant of the embodiments, every sensor 158 comprises a communication component 162, for example in the form of a transmitter. In another variant of the embodiments, a plurality of sensors 158 are coupled to a single communication component 162, for example in the form of a transmitter.

According to some embodiments, a local communication component 162L is configured to wirelessly transmit signals to an extracorporeal device. According to some embodiments, a local communication component 162L is configured to transmit signals to the remote communication component 162R, and the remote communication component 162R is configured to transmit signals received from the local communication component 162L, or derived therefrom.

According to some embodiments, the control circuitry 160 comprises a processor 164 (see FIG. 5B), which may be configured for processing and interpreting sensed signals received from sensors 158, and/or configured to control various functionalities of components of the monitoring apparatus 102, via the control circuitry 160. According to some embodiments, the processor 164 may include software for interpreting sensed signals. The processor 164 can include a central processing unit (CPU), a microprocessor, a microcomputer, a programmable logic controller, an application-specific integrated circuit (ASIC) and/or a field-programmable gate array (FPGA), without limitation. The control circuitry 160 may be provided as an electrical or an electro-optical circuitry. Although the control circuitry 160 is illustrated as comprising a processor 164, this is not meant to be limiting in any way, and a control circuitry 160 with dedicated electronic components can be provided.

According to some embodiments, the processor 164 comprises a local processor 164L, comprised within the local control circuitry 160L. Additionally or alternatively, the processor 164 may comprise a remote processor 164R, comprised within a remote control circuitry 160R.

According to some embodiments, the monitoring apparatus 102 further comprises at least one memory member 166 (see FIG. 5B), configured to store signals sensed by the sensor 158, and/or store data processed by the processor 164. A memory member 166 may include a suitable memory chip or storage medium such as, for example, a flash memory, solid state memory, or the like. A memory member 166 can be integral with the control circuitry 160 or may be in communication with the control circuitry 160 (e.g., may be in communication with the processor 164). According to some embodiments, at least one sensor 158 is in communication with the memory member 166.

According to some embodiments, the memory member 166 comprises a local memory 166L, which may be electrically connected to, or embedded within, at least one sensor 158 or the local control circuitry 160L. Additionally or alternatively, the memory member 166 may comprise a remote memory member 166R. According to some embodiments, the remote control circuitry 160R comprises the remote memory member 166R.

According to some embodiments, sensed signals may be stored in the memory member 166 and compared by the processor 164 to historical values, in order to detect improvement or deterioration of the measured flow characteristics.

According to some embodiments, the sensed signals may be mathematically manipulated or processed by the processor 164, in order to derive known relationships and indices that may be of clinical relevance or may be indicative of relevant clinical outcomes.

According to some embodiments, the control unit 160 is configured to transmit, for example via the communication component 162, raw or interpreted data, including stored data, to an extracorporeal device (e.g., an external reader unit 188 shown in FIG. 10A), via wireless communication protocols.

FIG. 8A shows an exemplary embodiment of a valve monitoring assembly 100, and portions of the environment in which the valve monitoring assembly 100 may operate. FIG. 8B shows a zoomed in view of a region indicated by a dashed border in FIG. 8A. In the exemplary embodiment illustrated in FIGS. 8A-8B, the prosthetic aortic valve 120' is shown to be mounted within the native aortic valve 40, such that its inflow end portion 124' protrudes into the LVOT 22, and its outflow end portion 122' protrudes into the aortic root 82. In such instances, a first pressure sensor **158*a* can be coupled to the inflow end portion 124, configured to measure left ventricular pressure, while a second pressure sensor 158*b* can be coupled to the outflow end portion 122, configured to measure aortic pressure. It will be clear that the position of the prosthetic valve 120' implantation, as well as the components of the monitoring apparatus 102 coupled thereto, are shown in FIGS. 8A-8B for illustrative purpose only, and that other types of prosthetic valves can be mounted within the native aortic valve or other native heart valves, having components of a monitoring apparatus 102** coupled thereto in various different configurations.

Sensed signals from pressure sensors **158*a* and 158*b* can be delivered via the respective communication channels 156*a* and 156*b* to the control circuit 160, and subtracted from each other by the processor 164 to derive the transvalvular pressure gradient. The results, as well as raw data, can be stored in the memory member 166. Pressure values, or transvalvular pressure gradient, can be compared by the processor 164 to historical values, and/or to threshold values, which in turn can be retrieved from the memory member 166**.

According to some embodiments, the monitoring apparatus 102 further comprises a power source, configured to supply power in a wired or wireless manner to at least one component of the monitoring apparatus 102.

The term "component of the monitoring apparatus", as used herein, refers to sensor 158, control circuitry 160, communication components 162, processor 164 and/or memory member 166, or any combination thereof, implemented as either local and/or remote components.

The terms "power", "electric power", "energy" and "electric energy", as used herein, are interchangeable.

According to some embodiments, the power source is a battery. In such embodiments, the battery may provide sufficient electric power to enable operability of at least some electric components of the monitoring apparatus 102 during a limited time period. Since the energy stored in batteries (i.e., non-rechargeable batteries) is depleted after a limited time period, it is highly desirable to provide a power source that may provide inexhaustible power supply.

According to some embodiments, the power source is a radiofrequency (RF) power source, comprising an induction capacitor circuit or any other energy harvesting mechanism, which may be powered using RF by a transmitting/receiving antenna.

According to some embodiments, an external reader unit 188 may utilize RF induction to activate the monitoring apparatus 102 periodically, and acquire measured data. According to some embodiments, the external reader unit 188 comprises an RFID reader unit, configured to allow power to be provided and/or information to be read from, and/or transmitted to, the control circuitry 160 and/or other components of the monitoring apparatus 102. In one variant of the embodiments, the RF power source comprises an internal RFID reader unit, configured to communicate with the external reader unit 188.

The circuitry of the RF power source may be structured to receive RF energy from an external RFID unit, and harvest energy therefrom, by converting the RF energy into DC energy (e.g., a DC voltage). The DC energy may be used to power components of the monitoring apparatus 102.

According to some embodiments, the monitoring apparatus 102 comprises a power source, implemented as a self-powered energy harvesting power source 168 (indicated for example in FIG. 5B), which can include a local self-powered energy harvesting power source 168L, a remote self-powered energy harvesting power source 168R, or both. The self-powered energy harvesting power source 168 comprises an energy harvesting mechanism 170, and an energy storage member 172 coupled thereto. The term "self-powered", as used herein, means that power is supplied by one or more components of the self-powered energy harvesting power source 168. A self-powered energy harvesting power source 168 is advantageous over an RF power source, as it is configured to harvest energy without requiring use of an extracorporeal device, such as the external RFID unit. According to some embodiments, the self-powered energy harvesting power source 168, and/or any component thereof, is configured to be secured to the patient. The configuration to be secured to the patient can comprise: an attachment member (not shown) that can secure the self-powered energy harvesting power source 168 to the prosthetic valve 120; an attachment member (not shown) that can secure the self-powered energy harvesting power source 168 to the control circuitry 160, including the local control circuitry 160L and/or the remote control circuitry 160R; a tissue engagement feature, as described below; and/or an attachment member (not shown) that can secure at least a portion of the self-powered energy harvesting power source 168 to an outer surface of the patient's skin.

According to some embodiments, the energy harvesting mechanism 170 is implemented as a kinetic energy harvesting mechanism 170, configured to convert kinetic energy, such as pulsating mechanical energy of a native organ or a component of a prosthetic valve 120, into electric energy.

A first type of a kinetic energy harvesting mechanism 170 is a clockwork-type energy harvesting mechanism 270, which is similar to the mechanism implemented in an automatic clockwork of a wristwatch, based on an oscillating weight connected to a transmission gear, which is connected to a spring coupled to an electromagnetic generator. In conventional implementations, a clockwork mechanism may be utilized to convert motions of a person's wrist during daily activities into electrical energy that can power the wristwatch.

An exemplary configuration of a monitoring apparatus 102 is shown in FIG. 8B, with a local control circuit 160L attached to the prosthetic valve 120, and local energy harvesting power source 168L attached to an inner wall of the pulsating left ventricle 16, and wired to the local control circuit 160L. FIG. 8C schematically shows an exemplary configuration of the local control circuitry 160L of FIG. 8B. FIG. 8D schematically shows an exemplary configuration of the local energy harvesting power source 168L of FIG. 8B, equipped with a clockwork-type energy harvesting mechanism 270.

According to some embodiments, as illustrated in FIG. 8D, a clockwork-type energy harvesting mechanism 270 comprises an oscillating weight 272, a mechanical rectifier 276 coupled to and configured to be driven by the mechanical weight 272, a spring such as a spiral spring 278 coupled to the mechanical rectifier 276, and an electromagnetic generator 280 attached to the spiral spring 278. According to some embodiments, the electromagnetic generator 280 is an electromagnetic micro generator, i.e. an electromagnetic generator sized such that it can be implanted within the human body.

The oscillating weight 272 is configured to translate externally applied accelerations into oscillating rotational motions. The mechanical rectifier 276 is configured to translate these oscillations into a unidirectional rotation, thereby allowing harvesting energy from rotations in both directions. The unidirectional rotation is configured to wind the spiral spring 278, which temporarily stores the energy in mechanical form. According to some embodiments, the mechanical rectifier 276 can comprise a pair of ratchet wheels, such that the mechanical power supplied by the oscillating weight is distributed to the two ratchet wheels. One of the ratchet wheels is fastened to a first end of the spiral spring 278. Therefore, the oscillating action of the oscillating weight 272 is able to wind the spring 278 regardless of movement direction. Finally, the electromagnetic micro generator 280 is configured to convert the rotational motion into an electrical signal. Specifically, the second end of the spiral spring 278 is fastened to the generator 280. When the torque of the spiral spring 278 equals the holding torque of the generator 280, the spring 278 unwinds and drives the electromagnetic micro generator 280.

The design parameters of components of the clockwork-type energy harvesting mechanism 270, including, for example, the shape and weight of the oscillating weight 272, may be adapted to provide appropriate sensitivity to motions of the native organ or prosthetic component to which the mechanism 270 is attached.

According to some exemplary embodiments, the kinetic energy harvesting circuitry is attached to the patient's heart, to convert heart motions into electrical impulses. Particularly, the oscillating weight 272 is positioned such that the motions of the heart generate oscillations of the oscillating weight 272. According to other exemplary embodiments, the clockwork-type energy harvesting circuitry 270 may be attached to the patient's blood vessel wall (e.g., aortic wall), to convert pulsating blood vessel motions (e.g., during transitions between systolic and diastolic phases) into electrical impulses. According to yet other exemplary embodiments, the clockwork-type energy harvesting circuitry may be attached to movable components of the prosthetic valve 120, such as the frame 126 or at least one of the leaflets 140, to convert frame or leaflet motions into electrical impulses.

According to some embodiments, the kinetic energy harvesting circuitry may be implemented in a patch, attachable to the mechanically movable target organ or prosthetic component. Alternatively, the kinetic energy harvesting circuitry may be implemented in a disc-shaped, rod-shaped, or any otherwise shaped structure, configured to conform to and/or be situated against a target organ or prosthetic component to which it is designed to attach.

According to some embodiments, the power source further comprises an energy storage member 172, such as a capacitor, inductor or electrochemical accumulator, functionally coupled to the kinetic energy harvesting mechanism 170, and configured to temporarily store and/or buffer the generated energy.

It is preferable for the energy storage member to be provided as a relatively small component, which can be according to some embodiments, a bypass capacitor, a small super capacitor, or a thin film rechargeable battery.

In the exemplary configuration shown in FIGS. 8A-8D, the clockwork-type energy harvesting mechanism 270 is attached to the inner wall of the left ventricle 16, for example at the LVOT 22 in close vicinity to the prosthetic valve 120, allowing it to convert pulsations of the left ventricle 16 into electrical impulses that can be stored in the energy storage member 172.

According to some embodiments, the monitoring apparatus 102 may include a local energy harvesting power source 168L which is completely attached, directly or indirectly, to the prosthetic valve 120. According to some embodiments, the monitoring apparatus 102 may include a local control circuitry 160L which is completely attached, directly or indirectly, to the prosthetic valve 120. An exemplary embodiment may include a local control circuitry 160L disposed around, or otherwise coupled to, the prosthetic valve 120; an energy harvesting power source 168 that includes a kinetic energy harvesting mechanism 270, attached to at least one leaflet 140; and an energy storage member 172 comprised within the local control circuitry 160L, and connected to the kinetic energy harvesting mechanism 270 (embodiment not shown).

According to some embodiments, the monitoring apparatus 102 may include a local energy harvesting power source 168L which is completely attached to a native organ contacted by, or in close proximity to, the prosthetic valve 120. According to some embodiments, the monitoring apparatus 102 may include a local control circuitry 160L which is completely attached to a native organ contacted by, or in close proximity to, the prosthetic valve 120. An exemplary embodiment may include an energy harvesting power source 168 with a kinetic energy harvesting mechanism 270, attached to an organ such as a vessel wall against which the prosthetic valve 120 is mounted, or a heart wall (e.g., an outer or an inner wall of an atrium or a ventricle) in the vicinity of the prosthetic valve 120. In one variation of the embodiments, the local control circuitry 160L comprises the local energy harvesting power source 168L, and is attached to said organ or native tissue, while being in communication with the at least one sensor 158 attached to the valve 120, for example—configured to control operation of, provide power to, and/or receive signals from the at least one sensor 158. In another variation of the embodiments, the local control circuitry 160L is separately attached to the same or to a different organ, in close proximity to the kinetic energy harvesting circuitry, while being functionally connected to both the kinetic energy harvesting mechanism 270 (e.g., to receive power therefrom) and to the at least one sensor 158.

According to some embodiments, the local and/or remote energy harvesting power source 168 comprises an energy harvesting mechanism 170 implemented as a piezoelectric energy harvesting mechanism, configured to convert kinetic energy, such as pulsating mechanical energy of a native organ or a component of a prosthetic valve 120, into electrical energy (embodiments not shown). While relying on a similar source of mechanical energy, the piezoelectric energy harvesting mechanism differs from the aforementioned kinetic energy harvesting mechanism 270 in that instead of having an oscillating weight and a transmission gear, the piezoelectric energy harvesting mechanism comprises a piezoelectric element, such as polyvinylidene fluoride (PVDF), which is configured to generate an electric charge upon being bent, flexed or vibrated. For example, the piezoelectric element can be in a fixed position, such that the beating of the heart periodically applies force thereto, thereby generating an electric charge. According to some embodiments, the piezoelectric element can be stretched along the surface of the heart, such that the beating of the heart periodically bends the piezoelectric element, thereby generating an electric charge.

The piezoelectric energy harvesting mechanism may further include a voltage converting circuitry, connected to the piezoelectric element and to an energy storage member 172, and configured to convert the output voltage of the piezoelectric element into a DC signal, which is then stored in the energy storage member 172.

Positioning and arrangement of the piezoelectric energy harvesting mechanism, including potential sites of attachment and potential configurations with respect to other components of the monitoring apparatus 102, may be implemented according to any of the embodiments described above for the kinetic energy harvesting mechanism 270.

According to some embodiments, the local and/or remote power source 168 comprises an energy harvesting mechanism implemented as a solar energy harvesting mechanism 370, configured to convert light into electrical energy. Since near-infrared light may penetrate the human skin, such a conversion is possible in solar cells which are implanted subcutaneously. Although harvesting mechanism 370 is described in relation to solar energy, this is not meant to be limited to sunlight. Particularly, solar energy harvesting mechanism 370 can be configured to convert into electrical energy any type of light, including indoor light, such as light from fluorescent light sources, light emitting diode (LED) sources and incandescent light sources.

Figures 9A, 9B, 9C, 9D:
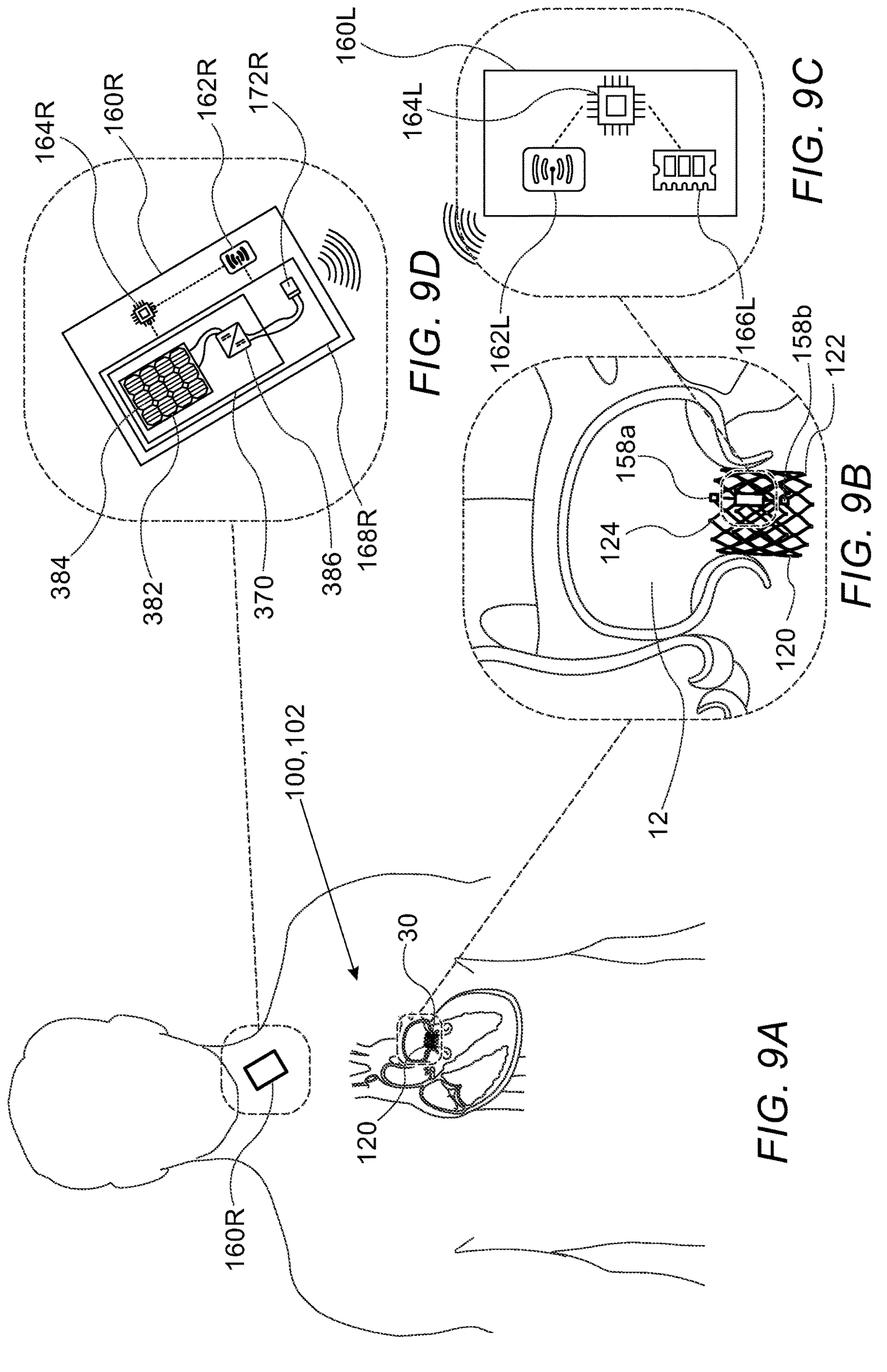
FIGS. 9A-9D show a valve monitoring assembly equipped with a solar energy harvesting mechanism, according to some embodiments.

FIG. 9A shows a valve monitoring assembly 100 comprising a prosthetic valve 120 implanted in the native mitral valve 30. FIG. 9B shows a zoomed in view of the region indicated by a dashed border in FIG. 9A. In some instances, a prosthetic mitral valve 120 can be mounted such that its inflow end portion 124 protrudes into the left atrium 12, and the outflow end portion 122 protrudes into the left ventricle 16. In such instances, a first pressure sensor **158*a* can be coupled to the inflow end portion 124, configured to measure left atrial pressure, while a second pressure sensor 158*b* can be coupled to the outflow end portion 122, configured to measure left ventricular pressure. The sensed signals can be delivered via the communication channels 156*a* and 156*b* to the control circuit 160, and subtracted from each other by the processor 164 to derive the pressure gradient across the mitral valve. The results, as well as raw data, can be stored in the memory member 166. Pressure values or pressure gradients can be compared by the processor 164 to historical values, and/or to threshold values, retrieved from the memory member 166**.

An exemplary configuration of a monitoring apparatus 102 is shown in FIGS. 9A-9B, with a local control circuit 160L attached to the prosthetic valve 120, and a remote energy harvesting power source 168R positioned at a remote location of the patient's body (relative to the valve's site of implantation), wirelessly coupled the local control circuit 160L. The remote energy harvesting power source 168R can be implanted into the patient, e.g. subcutaneously. Alternatively, or additionally, at least a portion of the remote energy harvesting power source 168R can be fixed to an outer portion of the patient's skin. FIG. 9A shows a prosthetic valve 120 implanted within the native mitral valve 30, and at least one component of a monitoring apparatus 102 implanted at a location remote to the prosthetic valve 120, such as the neck region. The implantation sites for either the prosthetic valve 120 or components of the monitoring apparatus 102 are shown for illustrative purpose only, and may vary as necessary. FIG. 9B shows a zoomed in view of prosthetic valve 120 implanted within the native mitral valve 30. FIG. 9C schematically shows an exemplary configuration of the local control circuitry 160L of FIG. 9B. FIG. 9D shows an exemplary configuration of the remote control circuitry 168R, comprising a remote energy harvesting power source 168R equipped with a solar energy harvesting mechanism 370. It will be clear that the position of the prosthetic valve 120 implantation, as well as the components of the monitoring apparatus 102 associated therewith, are shown in FIGS. 9A-9B for illustrative purpose only, and that other types of prosthetic valves can be mounted within the native mitral valve or other native heart valves, having components of a monitoring apparatus 102 associated therewith in various different configurations.

According to some embodiments, a solar energy harvesting mechanism 370 comprises a solar module 382 which includes at least one solar cell, and preferably a plurality of solar cells 384. In some applications, the solar cells 384 can be connected to each other in series along the solar module. The solar module 382 is preferably made of a material having a light absorption rate which is negligible in the relevant spectral band, for example in a range between 350 and 1100 nm.

According to some embodiments, the solar energy harvesting mechanism 370 further comprises a power converter 386, functionally coupled to the solar module 382. According to some embodiments, the energy harvesting power source 168 further comprises an energy storage member 172, such as a capacitor or an electrochemical accumulator, functionally coupled to the solar energy harvesting mechanism 370, and configured to temporarily store and/or buffer the generated energy. According to some embodiments, the power converter 386 comprises the energy storage member 172.

Advantageously, a solar energy harvesting mechanism 370 does not necessarily include mechanically movable components, which may potentially improve long term durability thereof.

According to some embodiments, a solar energy harvesting mechanism 370 is comprised within a remote energy harvesting power source 168R, implanted subcutaneously in a region which may be exposed to ambient light, such as a patient's neck (as shown in FIG. 8A), hands or legs, and is functionally coupled to at least one local component of the monitoring apparatus 102, for example to provide power thereto via wired or wireless communication links.

Advantageously, solar or kinetic mechanisms for harvesting ambient or in situ energy, respectively, may provide continuous long-term autonomous operation of the monitoring apparatus after being implanted within the patient, without requiring external interfaces for its operation, as opposed to inductive powering techniques, for example.

According to some embodiments, the monitoring apparatus 102 includes a remote energy harvesting power source 168R, which may be connected by a flexible wire or cable, to local components such as a local control circuitry 160L and/or at least one sensor 158 (embodiments not shown). The cable can be configured to transmit collected energy from the remote power source to at least one local component of the monitoring apparatus 102 connected thereto.

According to some embodiments, the monitoring apparatus 102 includes a remote control circuitry 160R, which may be connected by a flexible wire or cable, to local components such as a local control circuitry 160L and/or at least one sensor 158 (embodiments not shown). The cable can be configured to transmit collected energy from the remote power source to at least one local component of the apparatus 102 connected thereto. Alternatively or additionally, the cable can be configured to carry signals from at least one local component, such as the local control circuitry 160L or at least one sensor 158, to the remote control circuitry 160R, and/or carry signals from the remote control circuitry 160R to at least one local component of the monitoring apparatus 102.

According to some embodiments, as shown in FIGS. 9A-9D, energy stored in the remote energy harvesting power source 168R is transformed into a suitable form for wireless transmission from a remote communication component 162R, such as a transmitter or a transceiver comprised within or functionally coupled to the remote control circuitry 160R, to a local communication component 162L, such as a receiver or a transceiver comprised within or functionally coupled to the local control circuitry 160L.

According to some embodiments, the remote communication component 162R comprises a coil antenna (not shown), configured to electromagnetically transmit energy stored in the remote power source 168R (e.g., in the remote energy storage member 172R), to the local communication component, which may also include a respective coil antenna. For example, the remote communication component 162R can convert the energy stored in the remote energy storage member 172R into an oscillating electromagnetic field. The electromagnetic field can then be received by the local control circuitry 162L to power the control circuitry 160 and/or the sensors 158.

According to some embodiments, the remote communication component 162R comprises an ultrasound transducer (not shown), configured to transmit energy stored in the remote energy harvesting power source 168R as ultrasound energy (e.g., in the remote energy storage member 172R), to the local communication component 162L, which may include a respective ultrasound receiver.

According to some embodiments, power is supplied to the at least one sensor 158, and potentially to other local or remote components, continuously. Alternatively, power may be supplied as needed, such as upon request from the control circuitry 160, or upon request from an extracorporeal device communicating with the control circuitry 160. Alternatively, or additionally, power may be supplied periodically, at predetermined time intervals.

According to some embodiments, the amount of energy flowing from the energy harvesting power source 168 to any local or remote component, may be controlled by the control circuitry 160.

Figures 10A, 10B, 10C:
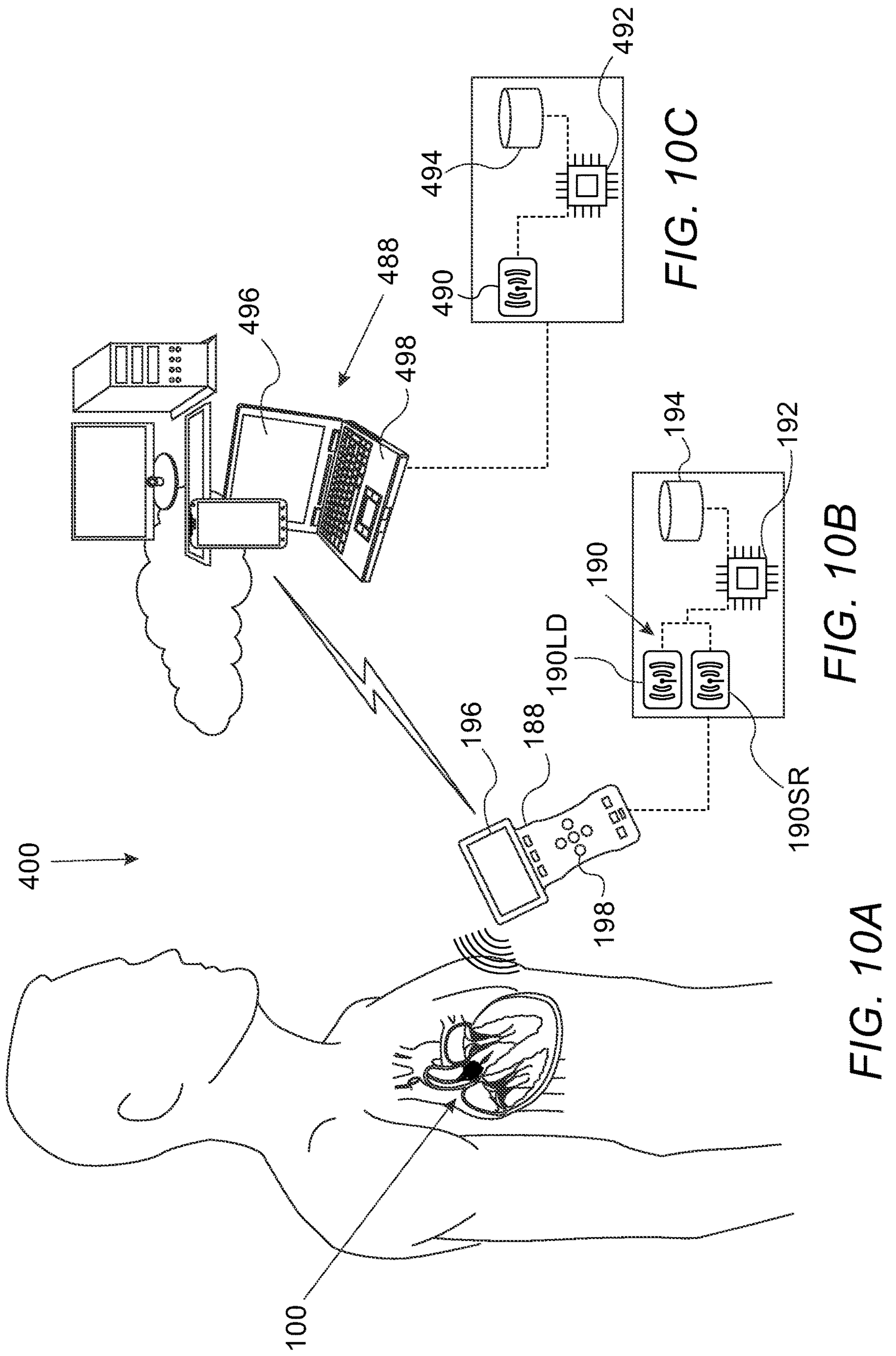
FIGS. 10A-10C show a valve monitoring system, according to some embodiments.

According to some embodiments, an extracorporeal device such as an external reader unit 188 may be utilized to wirelessly communicate with the monitoring apparatus 102. A valve monitoring system 400 may include a monitoring assembly 100 and an external reader unit 188 configured to wirelessly receive signals therefrom. An exemplary external reader unit 188 may be provided as a dedicated device for communicating with the monitoring apparatus 102, or as a commercially available mobile device such as a smartphone, a tablet, a smart watch and the like, which may include software commands for communicating with the monitoring apparatus 102. FIG. 10A shows a simplified view of an external reader unit 188 illustrated next to a patient, for communication with an implanted monitoring apparatus 102, according to some embodiments. FIG. 10B schematically shows components of the external reader unit 188 shown in FIG. 10A.

The external reader unit 188 includes at least one reader communication component 190, which can comprise a wireless communication component such as a transmitter, a receiver, and/or a transceiver, configured to wirelessly transmit signals to, and/or receive signals from, a communication component 162 of the monitoring apparatus 102.

According to some embodiments, at least one communication component 162 of the monitoring apparatus 102, such as a local communication component 162L and/or a remote communication components 162R, is configured to transmit and/or receive signals to and/or from at least one reader communication component 190 using one or more communication protocols such as Bluetooth, RF, LORA, Zigbee, Z-Wave, Near Field Communication (NFC), or the like.

According to some embodiments, the valve monitoring system 400 further comprises at least one external remote monitoring device 488, configured to communicate, either via wired or wireless communication link, with the external reader unit 188. The at least one external remote monitoring device 488, together with the external reader unit 188, may be utilized to communicate with the monitoring apparatus 102 and manage data related to measurement signals (i.e., raw data and/or processed data) transmitted by the monitoring apparatus 102.

FIG. 10A schematically shows an exemplary valve monitoring system 400, comprising the external reader unit 188 and at least one external remote monitoring device 488 configured to communicate with the external reader unit 188. FIG. 10C schematically shows components of an external remote monitoring device 488 shown in FIG. 10A. The at least one external remote monitoring device 488 may include an extracorporeal device configured to receive signals from, and/or transmit signals to, the external reader unit 188 via a wired or a wireless communication link. In some applications, the external remote monitoring device 488 includes, but is not limited to, a remote laptop or desktop computer, a remote smartphone, a remote smart watch, a remote tablet, a remote server, a remote cloud service infrastructure, and/or combinations thereof. In some applications, the at least one external remote monitoring device 488 includes a plurality similar or different types of external remote monitoring devices 488, and may include a network of external remote monitoring devices 488.

According to some embodiments, the reader communication component 190 comprises a short-range communication component 190SR, configured to communicate with a local communication component 162 via short range wireless communication protocols, such as Bluetooth, RF, LORA, Zigbee, Z-Wave, Near Field Communication (NFC), or the like.

According to some embodiments, the external reader unit 188 further comprises a reader processor 192, configured to control different functionalities of at least some components of the reader unit 188. In some applications, the reader processor 192 is further configured to process and interpret data transmitted from the monitoring apparatus 102. According to some embodiments, the reader processor 192 may include software for interpreting data transmitted from the monitoring apparatus 102. The reader processor 192 can include a central processing unit (CPU), a microprocessor, a microcomputer, a programmable logic controller, an application-specific integrated circuit (ASIC) and/or a field-programmable gate array (FPGA), without limitation. According to some embodiment, the reader processor 192 can be implemented as software run on a processor of a computer and/or smartphone.

According to some embodiments, the external reader unit 188 further comprises a reader storage member 194, configured to store data transmitted from the monitoring apparatus 102, and/or store data processed by the reader processor 192. A reader storage member 194 may include a persistent storage (e.g., a hard drive, a flash memory set, a CD/DVD ROM drive, and the like), a memory chip (e.g., a PROM, EPROM, EEPROM, ROM, solid state memory, or the like), and/or combinations thereof.

According to some embodiments, measurement data transmitted from the monitoring apparatus 102 to the reader unit 188 may be stored in the reader storage member 194 and compared by the reader processor 192 to historical (i.e., previously stored) values, in order to detect improvement or deterioration of the measured characteristics.

According to some embodiments, measurement data transmitted from the monitoring apparatus 102 to the reader unit 188 may be mathematically manipulated or processed by the reader processor 192, in order to derive known relationships and indices that may be of clinical relevance or may be indicative of relevant clinical outcomes.

According to some embodiments, the external reader unit 188 further comprises a reader display 196, serving as a visual interface configured to display information which may include, for example, raw measurement data or interpreted data, stored patient-specific data (e.g., physiological and medical profile), alerts, recommendations, and the like. Information may be displayed in the form of tables, charts, diagrams, as well as any kind of textual, tabular and/or graphical representation formats.

According to some embodiments, the external reader unit 188 further comprises reader input interface 198, such as buttons, sliders, a keyboard, an on-screen keyboard, a keypad, a mouse, a trackball, a touchpad, a touch-screen and the like. The reader input interface 198 enables a user of the external reader unit 188 to choose an option displayed on the reader display 196, input and/or modify data related to the patient or the monitoring apparatus 102, provide commands for execution, and the like. The reader input interface 198 and the reader display 196, together define an interactive interface of the external reader unit 188. The interactive interface may further include means for providing audible (e.g., sound) and/or tactile (e.g., vibration) signals.

The interactive interface may include a plurality of textual and/or graphical control elements shown in the reader display 196. The control elements can be shown as graphical icons, optionally associated with text labels or markers indicating the function or manner of operation of the corresponding control element. The control elements can include checkboxes, radio buttons, push buttons, drop-down lists, and the like. The control elements may also include input fields for textual input via the reader input interface 198.

According to some embodiments, the at least one external remote monitoring device 488 comprises an external remote communication component 490, which can comprise a wired communication component, a transmitter, a receiver, and/or a transceiver, configured to transmit signals to, and/or receive signals from, a reader communication component 190 of the reader unit 188.

According to some embodiments, the reader communication component 190 comprises a long-distance communication component 190LD, configured to communicate with the an external remote communication component 490 of the at least one external remote monitoring device 488, via long-distance wired or wireless communication protocols, such as LAN, cable communication, WiFi, GSM, GPRS, LTE, or the like. In some applications, the external reader unit 190 comprises at least one short-range communication component 190SR and at least one long-distance communication component 190LD, which are provided as distinct components, each functionally coupled to the reader processor 192 and controllable thereby. In some applications, a single reader communication component 190 serves both as a short-range communication component 190SR and as a long-distance communication component 190LD.

In some applications, the reader unit 188 may transmit, for example via the long-distance communication component 190LD, the measurement data received from the monitoring apparatus 102, and/or data processed by the reader processor 192, to at least one external remote monitoring device 488.

The at least one external remote monitoring device 488 may include an external remote processor 492, configured to control different functionalities of at least some components of the external remote monitoring device 488. In some applications, the external remote processor 492 is further configured to process and interpret data transmitted from the reader unit 188. According to some embodiments, the external remote processor 492 may include software for interpreting data transmitted from the reader unit 188.

The at least one external remote monitoring device 488 may further include an external remote storage member 494, configured to store data transmitted from the reader unit 188, and/or store data processed by the external remote processor 492. An external remote storage member 494 may include a persistent storage (e.g., a hard drive, a flash memory set, a CD/DVD ROM drive, and the like), a memory chip (e.g., a PROM, EPROM, EEPROM, ROM, solid state memory, or the like), and/or combinations thereof.

According to some embodiments, measurement data and/or processed data transmitted from the external reader unit 188 to the external remote monitoring device 488 may be stored in the external remote storage member 494 and compared by the external remote processor 492 to historical (i.e., previously stored) values, in order to detect improvement or deterioration of the measured parameters.

According to some embodiments, measurement-related data transmitted from the reader unit 188 to the external remote monitoring device 488 may be mathematically manipulated or processed by the external remote processor 492, in order to derive known relationships and indices that may be of clinical relevance or may be indicative of relevant clinical outcomes.

According to some embodiments, the external remote monitoring device 488 further comprises an external remote display 496, serving as a visual interface configured to display information which may include, for example, raw measurement data or interpreted data, stored patient-specific data (e.g., physiological and medical profile), alerts, recommendations, and the like. Information may be displayed in the form of tables, charts, diagrams, as well as any kind of textual, tabular and/or graphical representation formats.

According to some embodiments, any one of the memory member 166 of the control circuitry 160, the reader storage member 194, and/or the external remote storage member 494, may include software for interpreting and/or processing raw data (e.g., signals sensed by the at least one sensor 158). According to some embodiments, any one of the memory member 166 of the control circuitry 160, the reader storage member 194, and/or the external remote storage member 494, may include software for interpreting and/or further processing previously processed data, such as data previously processed by either one of the processor 164 of the control circuitry 160, the reader processor 192, and/or the external remote processor 492.

The software commands comprised in the memory member 166 of the control circuitry 160, the reader storage member 194, and/or the external remote storage member 494, may be executed by the processor 164 of the control circuitry 160, the reader processor 192, and/or the external remote processor 492, respectively. In some applications, software may include commands and/or instructions for averaging multiple measurements over several cardiac cycles, or for identifying cycle-to-cycle variations.

According to some embodiments, any one of the reader storage member 194 and/or the external remote storage member 494, may include software for displaying data on the reader display 196 and/or external remote display 496, respectively.

According to some embodiments, the remote monitoring device 488 further comprises external remote input interface 498, such as buttons, sliders, a keyboard, an on-screen keyboard, a keypad, a mouse, a joystick, a trackball, a touchpad, a touch-screen and the like. The external remote input interface 498 enables a user of the remote monitoring device 488 to choose an option displayed on the external remote display 496, input and/or modify data related to the patient, various components of the valve monitoring system 400 (such as the monitoring apparatus 102, the external reader unit 188, and/or the external remote monitoring device 488), provide commands for execution, and the like. The external remote input interface 498 and the external remote display 496, together define an interactive interface of the remote monitoring device 488. The interactive interface may further include means for providing audible (e.g., sound) and/or tactile (e.g., vibration) signals.

The interactive interface may include a plurality of textual and/or graphical control elements shown in the reader display 496. The control elements can be shown as graphical icons, optionally associated with text labels or markers indicating the function or manner of operation of the corresponding control element. The control elements can include checkboxes, radio buttons, push buttons, drop-down lists, and the like. The control elements may also include input fields for textual input via the reader input interface 498.

According to some embodiments, a single external reader unit 188 may be used with several different monitoring apparatuses 102 to monitor heart valve functioning of more than one patient. This may advantageously provide several benefits, such as reduced storage space requirements, enhanced portability, and costs reduction.

Figures 11A, 11B:
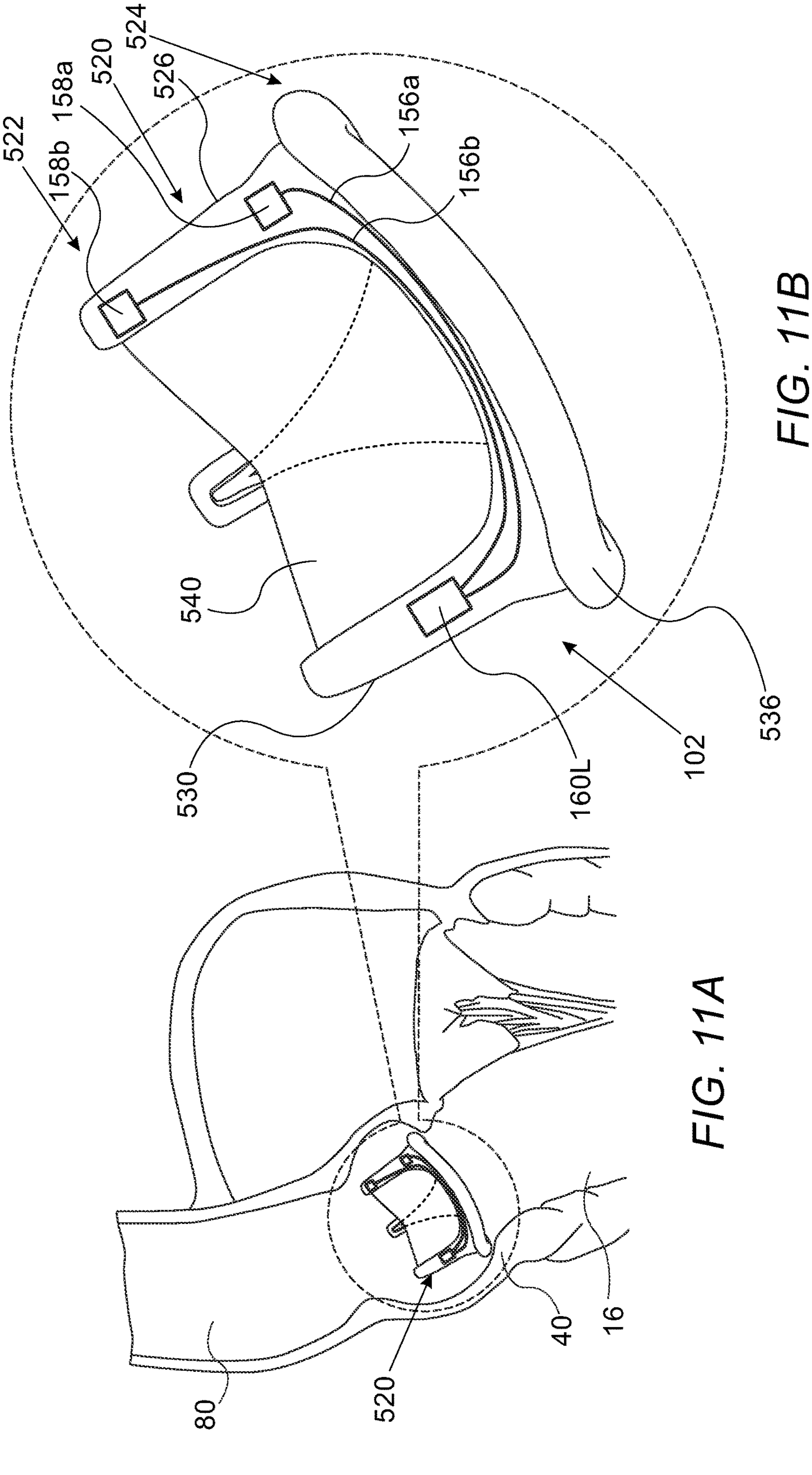
FIGS. 11A-11B show a valve monitoring assembly comprising a surgically implantable prosthetic valve, according to some embodiments.

According to some embodiments, a monitoring apparatus 102 may be utilized in combination with a surgically implantable prosthetic valve. FIG. 11A shows an exemplary surgically implantable prosthetic valve 520 with a monitoring apparatus 102 coupled thereto, and portions of the environment in which the monitoring assembly 100 that includes the surgically implantable prosthetic valve 520 and the monitoring apparatus 102, may operate. FIG. 11B shows a zoomed in view of a region indicated by a dashed border in FIG. 11B. It will be clear that the position of the surgical valve 520 implanted within the native aortic annulus 40, as well as the components of the monitoring apparatus 102 coupled thereto, are shown in FIGS. 11A-11B for illustrative purpose only, and that other types of surgically implantable valves can be mounted within the native aortic valve or other native heart valves, having components of a monitoring apparatus 102 coupled thereto in various different configurations.

The exemplary valve 520 shown in FIGS. 11A-11B comprises a support frame 526 and leaflets 540 attached thereto. The frame 526 may define a generally rigid ring 536 which encircles the valve 520 at the inflow end portion 524, and a plurality of commissure posts 530 extending proximally therefrom toward the outflow end portion 522.

Once exemplary configuration of a monitoring apparatus 102 coupled to the surgically implantable prosthetic valve 520 is shown in FIG. 11B, having a local control circuitry 160L attached to one commissure post 530, wired via communication channels 156*a* and 156*b* to a first sensor 158*a* and a second sensor 158*b*, which may be attached to another commissure post 530 at positions corresponding to the inflow end portion 524 and the outflow end portion 522, respectively. The communication channels 156 may follow a path along the ring 536 and the respective commissure posts 530. While a specific configuration of the monitoring apparatus 102 coupled to the surgically implantable prosthetic valve 520 is illustrated in FIGS. 11A-11B, it will be understood that other configurations, including attachment positions of components of the monitoring apparatus 102 to the surgically implantable valve 520, are within the scope of the current disclosure, and that a monitoring apparatus 102 may be similarly utilized with other types of surgically implantable valves.

In some cases, it may be desirable to utilize a monitoring apparatus 102 in combination with existing valves that have been previously implanted, to enable monitoring of flow characteristics associated with functioning of such valves. According to some embodiments, a method may be provided for implantation of a monitoring apparatus 102 in patients with an existing valve, which can be either a previously implanted transcatheter valve 120 or a surgically implanted valve 520.

Reference is now made to FIGS. 12A-12D. By way of example only, implantation steps of a monitoring apparatus 102 will be described with reference to a prosthetic valve 120 implanted within the native aortic valve 40. A monitoring apparatus delivery system 606, including a delivery catheter 612, may be utilized to deliver a monitoring apparatus 102 to the implantation site.

Figure 12A:
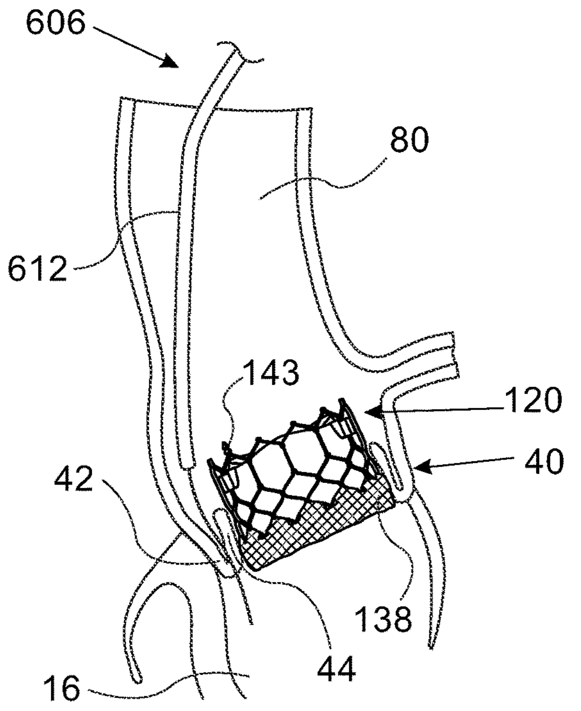
FIGS. 12A-12D show different stages of a monitoring apparatus implantation in the vicinity of a previously implanted prosthetic valve, according to some embodiments.
Figure 12B:
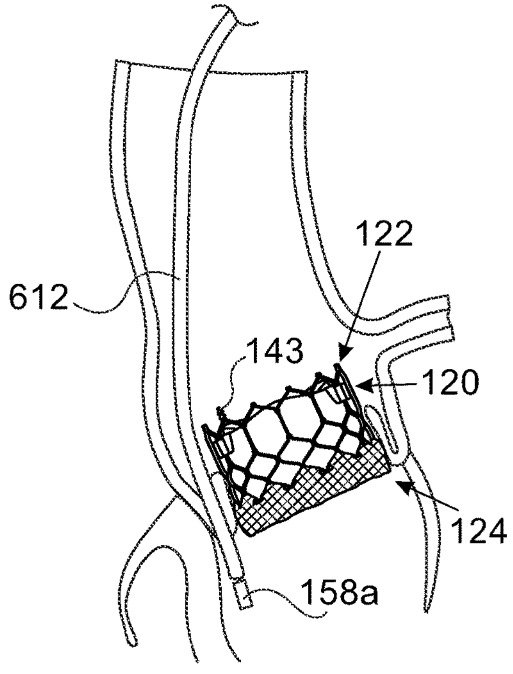

As shown in FIG. 12A, a delivery catheter 612 may be advanced over a guidewire, through the aorta 80, toward a first implantation site which may be distal to the aortic annulus 40, for example at or distal to the inflow end portion 124 of the prosthetic valve 120. The delivery catheter 612 may penetrate into the left ventricle 16, for example, through the soft tissue at the base of the native aortic leaflets 44, between the aortic annulus 42 and the inflow end portion 124 of the prosthetic valve 120.

Once the distal end of the delivery catheter 612 is in position, the delivery system 606 may be maneuvered so as to extend a first sensor 158*a* out of the delivery catheter 612, and attach it to a first desired implantation site, such as an inner wall of the left ventricle 16. Alternatively or additionally, a sensor 158, such as the first sensor 158*a*, may be attached to the inflow end portion 124 of the prosthetic valve 120.

Figure 12C:
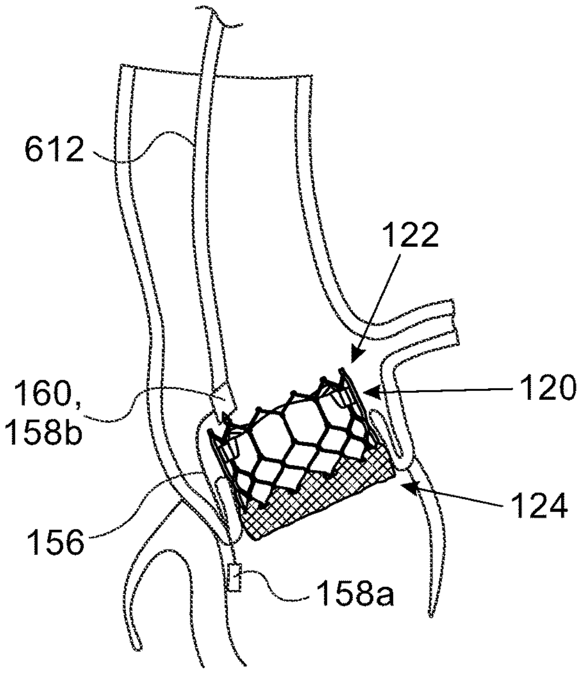

As shown in FIG. 12C, a following step may include retraction of the delivery catheter 612 to a second implantation site which may be proximal to the aortic annulus 40, for example at or distal to the outflow end portion 122 of the prosthetic valve 120. In the exemplary illustrations, the prosthetic valve 120 comprises a monitoring engagement member 143 extending from the outflow end portion 122, such that a second sensor 158*b* and/or other electric components of the monitoring apparatus 102, may be coupled thereto. In the exemplary embodiment shown in FIG. 12C, a control circuitry 160 with a second sensor 158*b* embedded therein, extends from the delivery catheter 612 to engage with the monitoring engagement member 143. The delivery catheter 612 can then be retracted from the patient's body, as shown in FIG. 12D, leaving the monitoring apparatus 102 implanted within the patient's body, including two sensors 158 position distal to and proximal to the coaptation zone of the leaflets 140 of prosthetic valve 120.

Figure 12D:
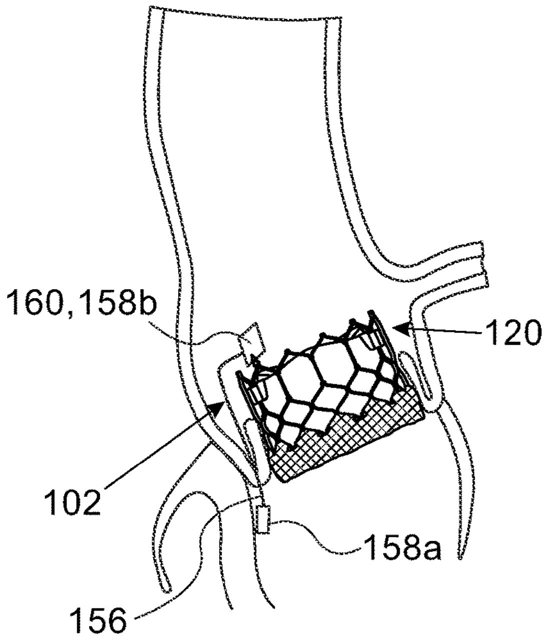

While the second sensor 158*b* is illustrated as a component embedded within the control circuitry 160 in FIGS. 12C-D, it will be clear that alternative configurations may include a control circuitry 160 and a second sensor 158*b* provided as separate components, operably coupled to each other via wired or wireless communication links, wherein each of the control circuitry 160 and the second sensor 158*b* can be attached to the prosthetic valve 120 (e.g., the outflow end portion 122 or a monitoring engagement member 143 extending therefrom), or to a native organ or tissue, such as the arterial wall. Moreover, alternative configurations may include the first sensor 158*a* embedded within the control circuitry 160, which can be attached to the prosthetic valve 120 (e.g., to the inflow end portion 124 or to a monitoring engagement member 143 extending therefrom), or to a native organ or tissue, such as the inner wall of the left ventricle 16.

In some instances, a monitoring apparatus 102 may be implanted over or in the vicinity of a prosthetic valve 120, 520, which has been previously implanted without any sensors 158 attached thereto or associated therewith. The previously implanted prosthetic valve 120, 520 may include at least one monitoring engagement member 143, enabling easier attachment of at least one component of the monitoring apparatus 102 thereto.

A monitoring apparatus 102, or a component thereof, is defined as "associated with" a valve if its implantation region allows it to measure a flow characteristic that may correlate with functioning of the valve. For example, a monitoring apparatus 102 may be associated with a prosthetic valve 120 by including two pressure sensors 158, each positioned at an opposite side of the coaptation zone of the leaflets 140, thereby enabling measurement of pressure signals on both sides thereof, from which a pressure gradient across the prosthetic valve 120 may be derived. This configuration can include attachment of both sensors 158 to the valve 120. For example, a first sensor 158*a* may be attached to the inflow end portion 124, and a second sensor 158*b* may be attached to an outflow end portion 122. Alternative configurations may include the first sensor 158*a* attached to a tissue distal to the prosthetic valve 120, such as an inner wall of the left ventricle 16, and/or the second sensor 158*b* attached to a tissue proximal to the prosthetic valve 120, such as an aortic wall. In another example, the monitoring apparatus 102 may be associated with a native valve (e.g., the aortic valve 40) by including two pressure sensors 158, each positioned at an opposite side of the annulus (e.g., the aortic annulus 42), thereby enabling measurement of pressure signals on both sides thereof, from which a pressure gradient across the native valve may be derived.

In some instances, an additional monitoring apparatus 102 or a sensor 158 may be implanted over or in the vicinity of a prosthetic valve 120, 520, which has been previously implanted with at least one sensor 158 attached thereto or associated therewith. For example, an additional sensor, such as a temperature sensor, may be implanted (for example, engaged with a monitoring engagement member 143) over or in the vicinity of a prosthetic valve 120, which has been previously implanted with a monitoring apparatus 102 that includes two pressure sensors. Such a scenario may advantageously enable addition of monitoring apparatuses 102 or sensors 158 that measure different properties, or similar properties at different regions, than those provided by the monitoring apparatus 102 or sensors 158 pre-implanted with the valve 120, so as to provide additional data when required.

While a monitoring apparatus 102 described in the current disclosure, includes sensors 158 that may be couple to a prosthetic valve 120, 520, or in the vicinity thereof, it should be understood that the monitoring apparatus 102 according to any embodiment of the current disclosure can be used in combination with other prosthetic devices aside from prosthetic valves, such as stents, docketing frames or grafts.

In some cases, it may be desirable to utilize a monitoring apparatus 102 to monitor the functioning of a native valve, for example to detect deterioration of the native valve's functioning that may require prosthetic valve implantation.

Figure 13A:
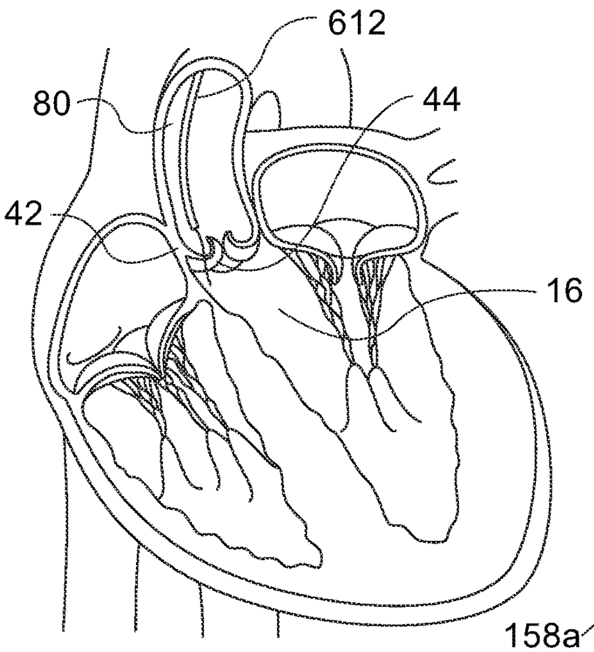
FIGS. 13A-13D show a monitoring apparatus implantation in the vicinity of a native valve, according to some embodiments.
Figure 13B:
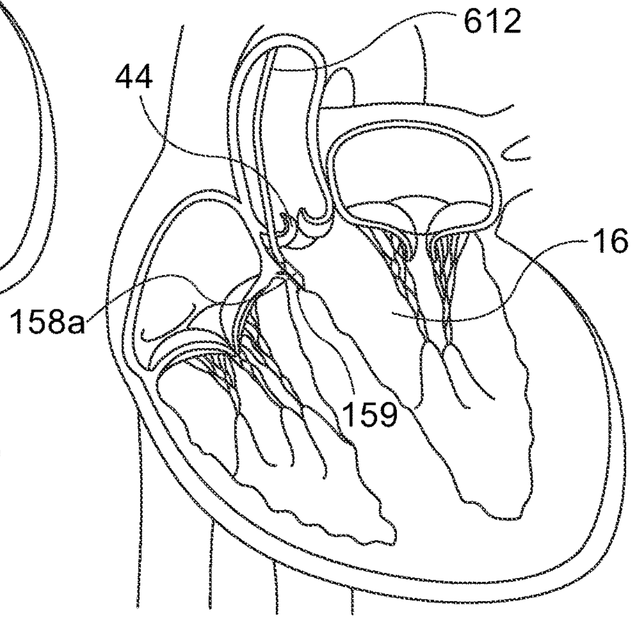

Reference is now made to FIGS. 13A-13D. By way of example only, implantation steps of a monitoring apparatus 102 will be described within the native aortic valve 40. A monitoring apparatus delivery system 606, including a delivery catheter 612, may be utilized to deliver a monitoring apparatus 102 to the implantation site. As shown in FIG. 13A, a delivery catheter 612 may be advanced over a guidewire, through the aorta, toward a first implantation site which may be distal to the aortic annulus 40. The delivery catheter 612 may penetrate into the left ventricle 16, for example, through the soft tissue of the native aortic leaflets 44. Once the distal end of the delivery catheter 612 is in position, the delivery system 606 may be maneuvered so as to extend a first sensor 158*a* out of the delivery catheter 612, and attach it to a first desired implantation site, such as an inner wall of the left ventricle 16.

According to some embodiments, any component of the monitoring apparatus 102, such as a sensor 158, a control circuitry 160 and/or an energy harvesting power source 168 may include sharp-ended tissue engagement features 159, for example in the form of spikes, barbs, hooks, claws and the like, configured to facilitate attachment of the sensor 158 to a soft tissue. By way of example, the first sensor 158*a* is illustrated in FIGS. 13 with tissue engagement features 159 in the form of sharp spikes that may penetrate into the inner wall of the left ventricle 16.

Figure 13C:
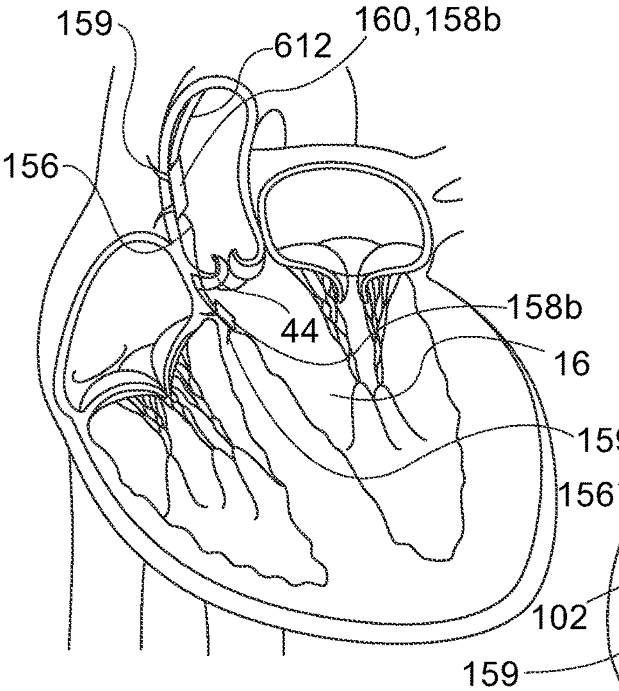

As shown in FIG. 13C, a following step may include retraction of the delivery catheter 612 to a second implantation site which may be proximal to the aortic annulus 40. In the exemplary embodiment shown in FIG. 13C, a control circuitry 160 with a second sensor 158*b* embedded therein, extends from the delivery catheter 612 and is attached to the aortic wall via tissue engagement features 159 in the form of sharp spikes. The delivery catheter 612 can then be retracted from the patient's body, as shown in FIG. 13D, leaving the monitoring apparatus 102 implanted within the patient's body, including two sensors 158 positioned distal to and proximal to the aortic annulus 40.

Figure 13D:
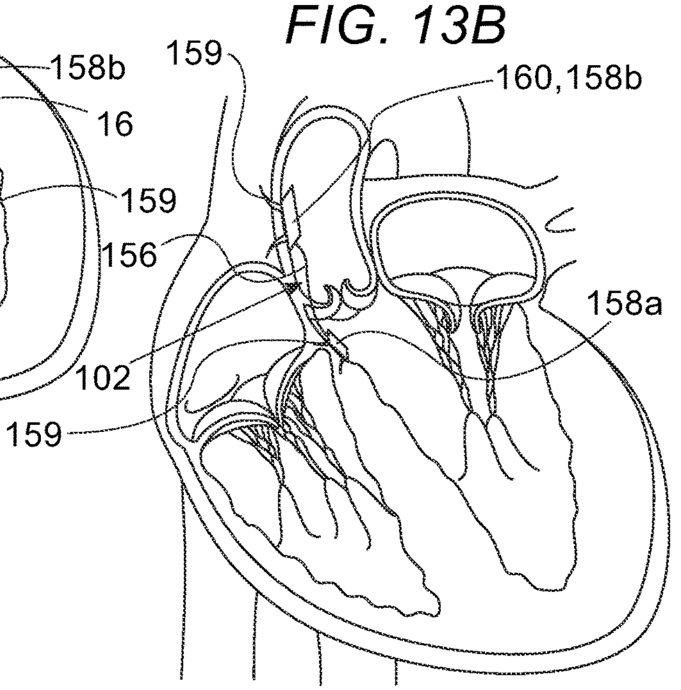

While the second sensor 158*b* is illustrated as a component embedded within the control circuitry 160 in FIGS. 13C-D, it will be clear that alternative configurations may include a control circuitry 160 and a second sensor 158*b* provided as separate components, operably coupled to each other via wired or wireless communication links, wherein each of the control circuitry 160 and the second sensor 158*b* can be separately attached to a native organ or tissue, such as the arterial wall. Moreover, alternative configurations may include the first sensor 158*a* embedded within the control circuitry 160, which can be attached to a native organ or tissue, such as the inner wall of the left ventricle 16.

Reference is now made to FIGS. 14A-14D, showing flowcharts of methods for monitoring flow characteristics via an implanted monitoring apparatus 102 that wirelessly communicates with an external reader device 188. According to some embodiments, the measured flow characteristics are associated with the functioning of a heart valve, and may be monitored to decide whether a treatment protocol should be recommended, and if so, to provide treatment protocol recommendations. In such embodiments, the methods 700 are for monitoring the functioning of a heart valve via flow characteristics measured by the implanted monitoring apparatus. According to some embodiments, the flow characteristics are associated with conditions that can be treated with medications, and are monitored to check whether a drug therapy should be recommended, and/or whether an existing drug therapy protocol should be modified. In such embodiments, the methods 700 are for monitoring conditions that may be treated by drug therapy protocols, via flow characteristics measured by the implanted monitoring apparatus.

Figure 14A:
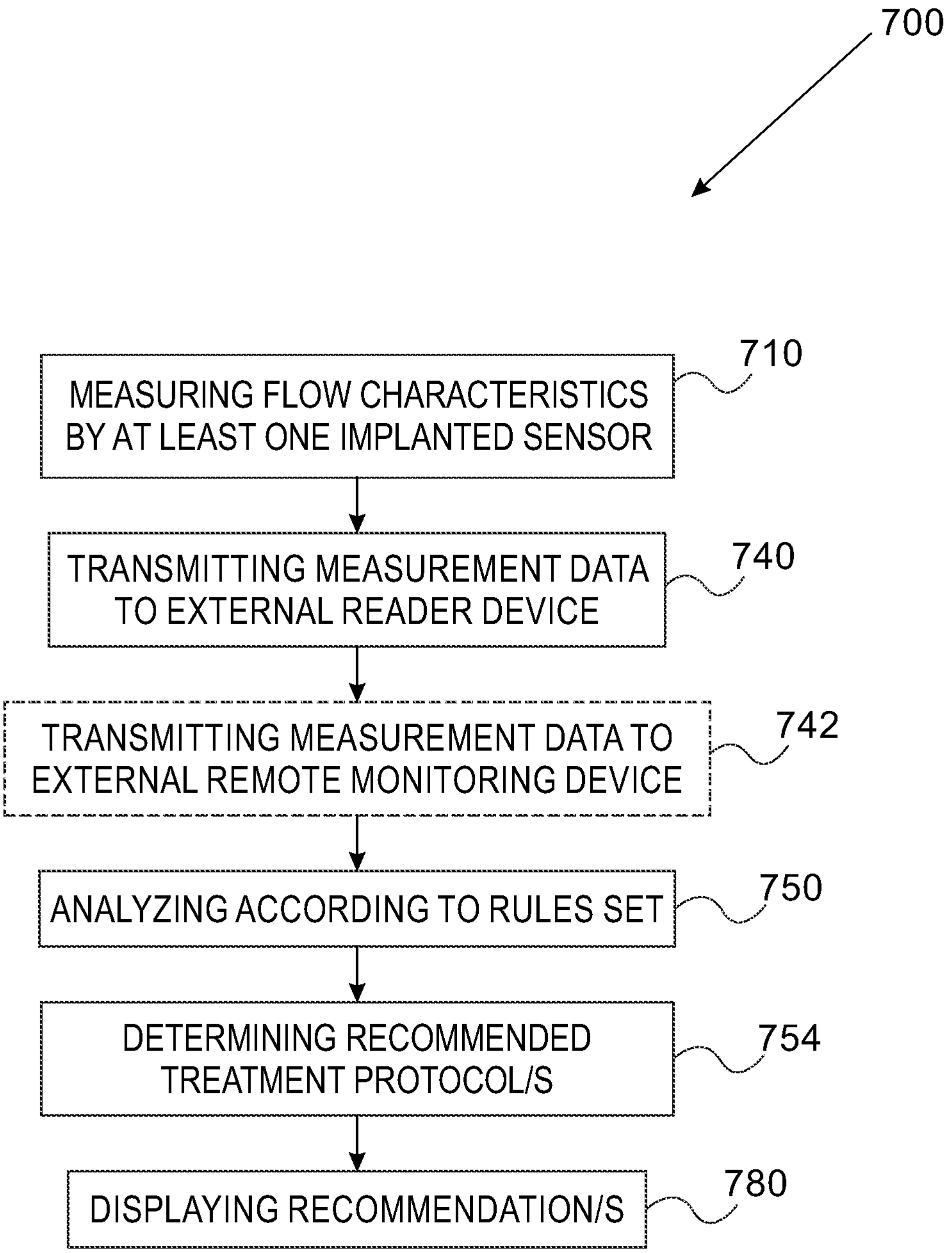
FIGS. 14A-14D show flowcharts of methods for heart valve monitoring, according to some embodiments.

FIG. 14A shows a flow chart of one embodiment of a method for providing recommendation for treatment protocols, according to monitored flow characteristics 700. While not explicitly shown in the flowchart, the method 700 may include an initial step of implanting a monitoring apparatus 102 according to any of the embodiments described herein above, including a monitoring apparatus 102 associated with any of: an expandable transcatheter prosthetic valve 120, a surgically implanted prosthetic valve 520, stents, docketing frames, shunts, and/or a native valve (e.g., native mitral valve 30 or native aortic valve 40). The implanted monitoring apparatus 102 comprises at least one implanted sensor 158, and at least one communication component 162 configured to wirelessly transmit signals (e.g., real-time measurement signals from the at least one sensor 158, or any signals derived therefrom) to the external reader device 188. Additional components, such as processor 164, control circuitry 160, memory member 166 etc., may be comprised in the monitoring apparatus 102 according to any of the embodiments described hereinabove.

The method 700 includes at step 710 of measuring, by the at least one implanted sensor 158 of the monitoring apparatus 102, a flow characteristic which may be optionally correlated with heart valve functioning, or may be correlated with any other condition that can be treated with drug therapy. A flow characteristic can be selected from: blood flow, blood pressure, and/or temperature. For example, a flow characteristic associated with heart valve functioning may include pressure signals measured on both sides of the valve, from which transvalvular pressure gradients may be derived. Blood flow velocity is another example of a flow characteristic that may be associated with heart valve functioning, from which the cardiac output may be derived if the flow cross-sectional area is known. The measured signals may be associated with the functioning of an implanted prosthetic valve 120, 520, and/or the functioning of a native heart valve. Depending on the mode of utilization, heart valve functioning may refer either to the functioning of a prosthetic heart valve 120, 520, or the functioning of a native heart valve (e.g., native mitral valve 30 or native aortic valve 40). In some cases, thrombus may be formed in regions subjected to low flow or blood stasis, such as the regions bound between leaflets and the frame of an implanted prosthetic valve. The measured flow characteristics may include pressure measurements from pressure sensors positioned on both sides of the monitored heart valve, from which transvalvular pressure gradients may be derived. Advantageously, transvalvular pressure can be of particular diagnostic value because of its potential correlation with valve thrombosis or other abnormalities of the heart valve functioning. For example, a transvalvular pressure gradient increased by 10 mmHg from baseline, may be correlated with leaflet thrombosis, pannus formation, and/or leaflet dysfunction.

The monitoring apparatus 102 may be conveniently utilized to provide more frequent readings related to heart valve functioning, relative to conventional monitoring methods such as CT imaging, which is more expensive, complex and inconvenient. The possibility of acquiring readings at higher frequency, and on ongoing basis, may assist in detection of subclinical leaflet thrombosis, advantageously enabling treatment thereof, reducing the risk posed by such a condition. If left untreated, subclinical thrombosis may lead to reduced effective orifice area and valve dysfunction, potentially converting to critical leaflet thrombosis.

The flow characteristics may be acquired by at least one flow sensor 158, configured to detect flow disturbances in the vicinity of the heart valve. Local flow disturbances and turbulence at the level of the leaflet surface might promote platelet adhesion and activation.

Alternatively, or additionally, the flow characteristics may include blood pressure or flow rate that can be measured by sensors 158 attached to a docketing frame (not shown) implanted in a vascular region other than a valve, such as the vena cava. Such flow characteristics may be useful for monitoring conditions that may be treated with drug therapy protocols, which may include, but are not limited to, heart valves. For example, the flow characteristics can be utilized to monitor the condition of CHF patients, in order to decide whether drug therapy protocols that include diuretics, should be recommended, or whether current drug therapy protocols should be modified.

At step 740, measurement data is wirelessly transmitted from the communication component 162 of the monitoring apparatus 102 to the reader communication component 190. The term "measurement data", as used herein, refers to raw data of the signals sensed by the at least one sensor 158, and/or processed data which includes values derived from the raw data. In some applications, any one of the processor 164 of the control circuitry 160, the reader processor 192, and/or the external remote processor 492, may be utilized to derive processed data by processing either raw data, and/or further processing previously processed data. In some applications, measurement data can be stored in any one of the memory member 166 of the control circuitry 160, the reader storage member 194, and/or the external remote storage member 494. Thus, measurement data may include real-time raw data, real-time processed data, and/or stored data.

In some applications, sensed signals may be delivered from the at least one sensor 158 to the communication component 162, and transmitted thereby to the reader communication component 190. In some applications, measurement data can be stored data retrieved by the communication component 162 from the memory member 166, and transmitted to the reader communication component 190 (e.g., to the short-range reader communication component 190SR). In some applications, measurement data received at the reader communication component 190 can be directly stored in the reader storage member 194, and/or can be communicated to the reader processor 192. The reader processor 192 may process measurement data communicated directly from the reader communication component 190 (e.g., from the short-range reader communication component 190SR) and/or stored data retrieved from the reader storage member 194. The resulting processed data can be stored in the reader storage member 194, and/or communicated to the reader communication component 190 (e.g., to the long-distance reader communication component 190LD) for transmission to the at least one external remote monitoring device 488 at optional step 742.

Measurement data, which can include stored data retrieved from the reader storage member 194, may be transmitted from the reader communication component 190 (e.g., via the long-distance reader communication component 190LD) to the external remote communication component 490. In some applications, measurement data received at the external remote communication component 490 can be directly stored in the external remote storage member 494, and/or can be communicated to the external remote processor 492. The external remote processor 492 may process measurement data communicated directly from the external remote communication component 490 and/or retrieved from the external remote storage member 494, and the resulting processed data can be stored in the external remote storage member 494, and/or transmitted to another external remote monitoring device 488.

In general, measurement data, which may include raw data as well as processed data, may be stored in a storage member at different stages of execution of the method 700, wherein the term "storage member" refers to any of a reader storage member 194 and/or an external remote storage member 494.

At step 750, measurement data can be analyzed by itself, or in combination with supplementary patient data, such as, but not limited to: historical measurement data of the patient (e.g., stored measurement data), physiological characteristics of the patient, allergies and sensitivities of the patient (e.g., drug sensitivities), additional clinical conditions the patient may suffer from (e.g., accompanying diseases), currently administered drugs, and the like. At step 754, a determination is made for at least one recommended treatment protocol, based on the analysis performed at step 750. The recommended treatment protocol may include more than one recommendation.

According to some embodiments, the recommended treatment protocol determined at step 754 may include an interventional recommended treatment protocol, such as prosthetic valve implantation. Such a recommendation may be applicable when a native heart valve is monitored by the monitoring apparatus 102, and deterioration of the native valve functioning is detected. The analysis may result in a recommendation to implant a prosthetic heart valve, either via a minimally invasive procedure (e.g., transcatheter heart valve implantation, for implanting an expendable heart valve 120) or via a surgical procedure (e.g., surgically implanting a heart valve 520). Moreover, if a monitoring apparatus 102 is associated with a currently implanted heart valve 120, 520, the analysis may result in a recommendation for performing a Valve-in-Valve (ViV) procedure, for example implantation of a new prosthetic heart valve 120 within a previously implanted prosthetic heart valve.

The analysis performed at step 750 may advantageously examine current measured data in combination with supplementary data to detect patient comorbidities. Certain patient comorbidities may be associated with development of thromboembolism. For example, advanced age, accompanying diseases (e.g., diabetes, cancer, chronic kidney disease) and inflammatory conditions, may be associated with hypercoagulability, which may be caused by an increase in circulating thrombogenic factors either due to increased production or reduced clearance thereof.

According to some embodiments, a recommended treatment protocol determined at step 754 is a recommended drug therapy protocol. A recommended drug therapy protocol may include instructions for medication regimens to treat or reduce symptoms associated with a condition correlated with valve functioning, such as inflammation, embolization, thrombus formation and the like. For example, a drug therapy protocol may include anticoagulation agents, such as vitamin K antagonist (VKA), apixaban, rivaroxaban, edoxaban and the like, to name a few. A drug therapy protocol may also include antiplatelet regimens, such as dual antiplatelet therapy with clopidogrel and aspirin. A drug therapy protocol may similarly combine anticoagulation and antiplatelet agents, such as a triple antithrombotic therapy including VKA, apixaban and aspirin. Other drug protocols may be applicable for other conditions monitored by the monitoring apparatus 102. For example, angiotensin-converting enzyme inhibitors, diuretics and/or digoxin, may be included in drug therapy protocols for CHF patients.

In some applications, the analysis at stage 750 utilizes a rules set and/or a scoring system to rank the suitability of various treatment protocols, including various drug therapies, for the patient, according to at least some of: current measurement data, historical measurement data (i.e., stored data) which can be retrieved from the reader storage member 194 and/or the external remote storage member 494, patient comorbidities (including patient physiological profile and patient current medical profile), patient allergies and sensitivities, patient medical history, additional drugs administered to the patient, as well as any other type of parameters which can influence the suitability of specific treatment protocols, such as drug therapies, to a patient. The rules set of step 750, throughout embodiments of the methods described in conjunction with FIGS. 14A-14D, may be also referred to as the "first rules set".

In some applications, the rules set can include instructions for evaluating statistical likelihood or probability for the presence of a specific valve-related condition, such as leaflet thrombosis, based on measurement data (such as transvalvular pressure gradients), potentially along with supplementary patient data (e.g., patient age). Statistical probabilities may be based on case studies and scientific literature, as well as on ongoing analysis of data collected from patients with implanted monitoring apparatuses 102, utilized according to the methods described herein.

The at least one recommended treatment protocol is displayed on a display, such as the reader display 196 or the external remote display 496, at step 780. In some applications, the displayed recommendations may include a scored list of optimal drugs which may be most suited for administration. If more than one recommendation is displayed, one of the optional recommended treatment protocols (e.g., various optional drug therapies) can be manually selected by the clinician or caretaker according to additional criteria.

The analysis and determination at steps 750 and 754, respectively, may be performed, in some applications, by the reader processor 192 and/or by the external remote processor 492. In some applications, the analysis and determination at steps 750 and 754 are performed by the reader processor 192, and the resulting recommendations may be delivered by the reader communication component 190 (e.g., to the long-distance reader communication component 190LD) for transmission to the at least one external remote monitoring device 488. The recommendations received by the external remote communication component 490 may be stored in the external remote storage member 494, and may be displayed in the external remote display 496.

Advantageously, the analysis performed at stage 750 can prevent harmful drug interactions in complex patients having other prescriptions, and prevent administration of drugs which are contradicted due to specific patient medical profile.

In some embodiments, a database of available drugs may be stored in the reader storage member 194 and/or external remote storage member 494. The database of available drugs may be periodically modified, for example according to drugs approved by the HMO or availability in stock.

In some embodiments, patient-specific data may be obtained from an existing patient's electronic medical record (EMR), without the need for a caretaker to manually input such data via the reader input interface 198 and/or the external remote input interface 498.

In some applications, the reader input interface 198 and/or the external remote input interface 498 may be utilized to edit the rules set and/or scoring system, for example according to updated clinical studies, according to updated HMO policies, and so on.

In some cases, a constriction developing in the valve may result in higher velocity detected by a flow sensor 158, or a higher transvalvular pressure drop detected by at least two pressure sensors 158 on both sides of the leaflets' coaptation zone. However, increased cardiac activity resulting from a patient exercising, may also cause similar increase in velocity, which is not the result of cross-sectional narrowing of the heart valve. Similarly, patient inactivity can produce reduce flow velocities or transvalvular pressure gradients. Thus, the analysis performed at step 750 may include supplementary data concerning the physical activity of the patient at the time of obtaining measurement data by the sensor 158. The physiological state data may be manually logged data (e.g., by manually providing type of activities performed at specific times, by the patient or other user of the external reader unit 188 or an external remote monitoring device 488), or it may be obtained from additional sensors, which may be additionally comprised in the monitoring apparatus 102, or provided separately and in communication with the external reader unit 188, such as a heart rate monitor, an accelerometer indicating exercise activity the patient undergoes in real-time, a posture sensor and the like.

Figure 14B:
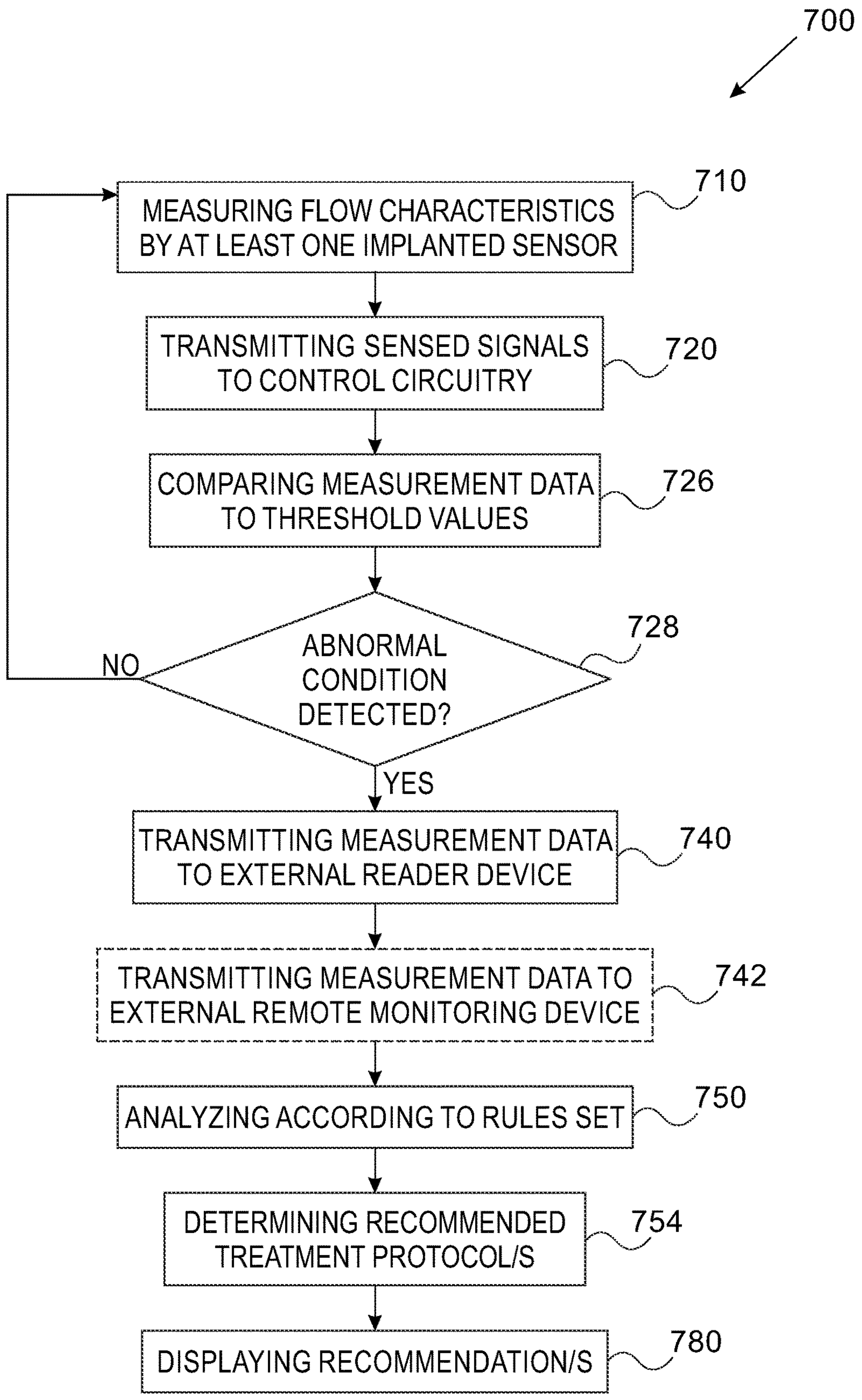

FIG. 14B shows another embodiment of the heart valve monitoring method 700, which further includes delivering the sensed signals of step 710, via wired and/or wireless communication links, to the control circuitry 160, at step 720. The sensed signals can be delivered to the control circuitry 160, in some applications, via at least one communication channel 156.

Measurement data may be compared, at step 726, with threshold values, which may be stored in tables or graphs of known relationships between the measured flow characteristic and other characteristics of interest. In some applications, threshold values are stored in the memory member 166 of the control circuitry 160.

The comparison at step 726 may be performed, according to some embodiments, by the processor 164 of the control circuitry 160. In some applications, the processor 164 receives sensed signals directly from the at least one sensor 158, for example, via at least one communication channel 156, and compares them in real-time to threshold values retrieved from the memory member 166. In some applications, the processor 164 receives sensed signals directly from the at least one sensor 158, processes such signals to derive processed values, and compares the processed values to threshold values retrieved from the memory member 166. In some applications, the processor 164 retrieves both measurement data and threshold values from the memory member 166, and performs the comparison at stage 726.

In some cases, threshold values may be specific to attributes of a monitoring apparatus 102, for example, as a function of the type and/or dimensions of the prosthetic valve 120, 520, the type and model of the at least one sensor 158, and so on. Threshold values may further depend on the site of implantation, anatomical and physiological attributes of the patient, and so on. Threshold values can be pre-programmed or pre-stored into a memory member 166, and may vary between various monitoring apparatuses 102.

At step 728, a determination is made as to whether the result of the comparison performed at step 726 is indicative of an abnormal condition, which may be of clinical significance. If so, the measurement data can be further analyzed at step 750. The determination at step 728 may be performed by the processor 164. In some applications, the determination performed at step 728 is not limited only to a binary determination regarding the likelihood for existence of an abnormal condition, but may further extend to classification of the type and degree of the abnormal condition. This classification may be added as a portion of the measurement data, which can be stored in a memory member 166, and/or transmitted via the communication component 162.

Figure 14C:
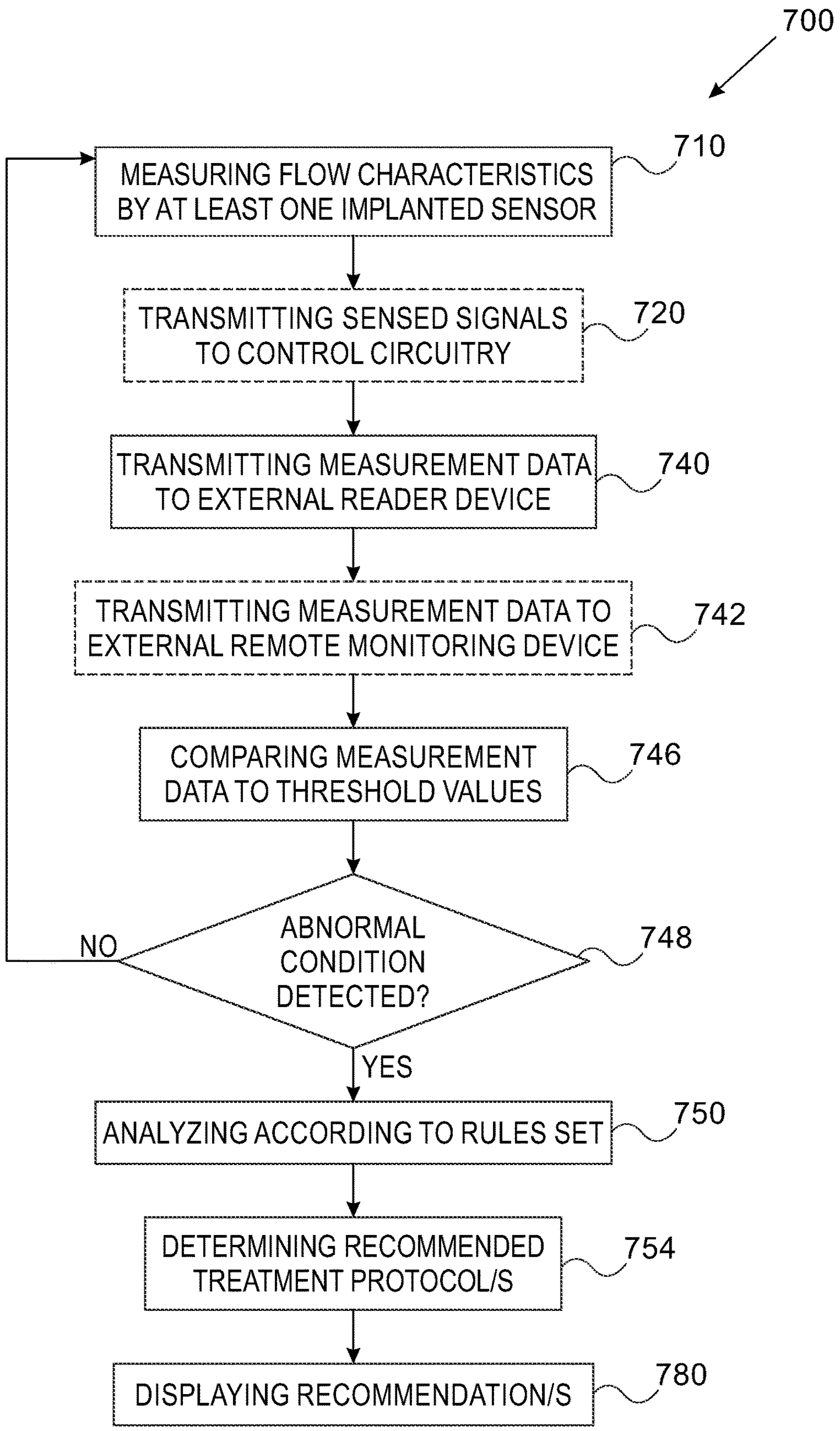

FIG. 14C shows another embodiment of the heart valve monitoring method 700, wherein transmitting sensed signals to the control circuitry 160 at step 720 is optional, and wherein measurement data comparison at step 746 and abnormal condition detection at step 748 are performed by the external remote monitoring device 188 and/or by the at least one remote monitoring device 488.

The comparison at step 746 may be performed, according to some embodiments, by the reader processor 192. In some applications, threshold values are stored in the reader storage member 194. The reader processor 192 receives measurement data communicated from the reader communication component 190, and compares it to threshold values retrieved from the reader storage member 194. The reader processor 192 may further process the measurement data communicated from the reader communication component 190 prior to performing the comparison, for example, if such measurement data comprises raw data. In some applications, the reader processor 192 retrieves both measurement data and threshold values from the reader storage member 194, and performs the comparison at step 746.

In some applications, threshold values may be retrieved from the memory member 166, and transmitted via the communication component 162, potentially along with measurement data, to the reader unit 188. In such applications, the comparison at step 746 may be performed by a reader processor 192, between measurement data (e.g., communicated from the reader communication component 190 and/or retrieved from the reader storage member 194) and threshold values received by and communicated from the reader communication component 190. This mode of operation may be advantageous for a single reader unit 188 utilized in combination with various monitoring apparatuses 102 of numerous patients.

Threshold values transmitted from a monitoring apparatus 102 to a reader communication component 190 may be stored in the reader storage member 194, and may be retrieved by the reader processor 192 for subsequent comparisons, for example in cases wherein the identity of the patient associated with these threshold values is known or recognizable. In some applications, patient identity may be selected or provided by an operator of the reader unit 188 via the reader input interface 198. Alternatively or additionally, a patient identity parameter may be stored in the memory member 166, and transmitted by the communication component 162 to the reader unit 188.

The comparison at step 746 may be performed, according to some embodiments, by the external remote processor 492. In some applications, threshold values are stored in external remote storage member 494. The external remote processor 492 receives measurement data communicated from the external remote communication component 490, and compares it to threshold values retrieved from the external remote storage member 494. The external remote processor 492 may further process the measurement data communicated from the external remote communication component 490 prior to performing the comparison, for example, if such measurement data comprises raw data. In some applications, the external remote processor 492 retrieves both measurement data and threshold values from the external remote storage member 494, and performs the comparison at step 746.

In some applications, threshold values may be retrieved from the reader storage member 194, and transmitted via the reader communication component 190 (e.g., via the long-distance reader communication component 190LD), potentially along with measurement data, to the external remote monitoring device 488. In such applications, the comparison at step 746 may be performed by the external remote processor 492, between measurement data (e.g., communicated from the external remote communication component 490 and/or retrieved from the external remote storage member 494) and threshold values received by and communicated from the external remote communication component 490. This may be advantageous if an external remote monitoring device 488 is utilized in combination with various monitoring apparatuses 102 of numerous patients.

Threshold values transmitted from a reader unit 188 to an external remote communication component 490 may be stored in the external remote storage member 494, and may be retrieved by the external remote processor 492 for subsequent comparisons, for example in cases wherein the identity of the patient associated with these threshold values is known or recognizable. In some applications, patient identity may be selected or provided by an operator of the external remote monitoring device 488 via the external remote input interface 498. Alternatively or additionally, a patient identified parameter may be transmitted by the reader communication component 190 (e.g., via the long-distance reader communication component 190LD) to the external remote monitoring device 488.

The determination at step 748 may be performed by the same processors executing the comparison at step 746, such as the reader processor 192, and/or the external remote processor 492. In some applications, the determination performed at step 748 is not limited only to a binary determination regarding the likelihood for existence of an abnormal condition, but may further extend to classification of the type and degree of the abnormal condition. This classification may be added as a portion of the measurement data, which can be stored in a reader storage member 194 and/or external remote storage member 494, and/or transmitted via the reader communication component 190.

According to some embodiments, the comparison and determination steps 746 and 748, respectively, may be implemented as subroutines of the analysis performed at step 750.

In some cases, it may be desirable to monitor effectiveness of a selected treatment protocol. For example, a clinician may prescribe a drug therapy protocol based on a recommendation determined and displayed in steps 754 and 780, respectively. The clinician may log the decision to accept a chosen treatment protocol in the external reader unit 188 and/or the external remote monitoring device 488. The method 700 may be expanded to apply different rule sets for each scenario. For example, a first rule set may be implemented for a scenario of an abnormal condition detected in steps 728 and/or 748, while a second rule set may be implemented for a scenario of a patient currently treated according to treatment guidelines recommended at a previous execution of step 754, so as to monitor effectiveness of the treatment protocol.

Figure 14D:
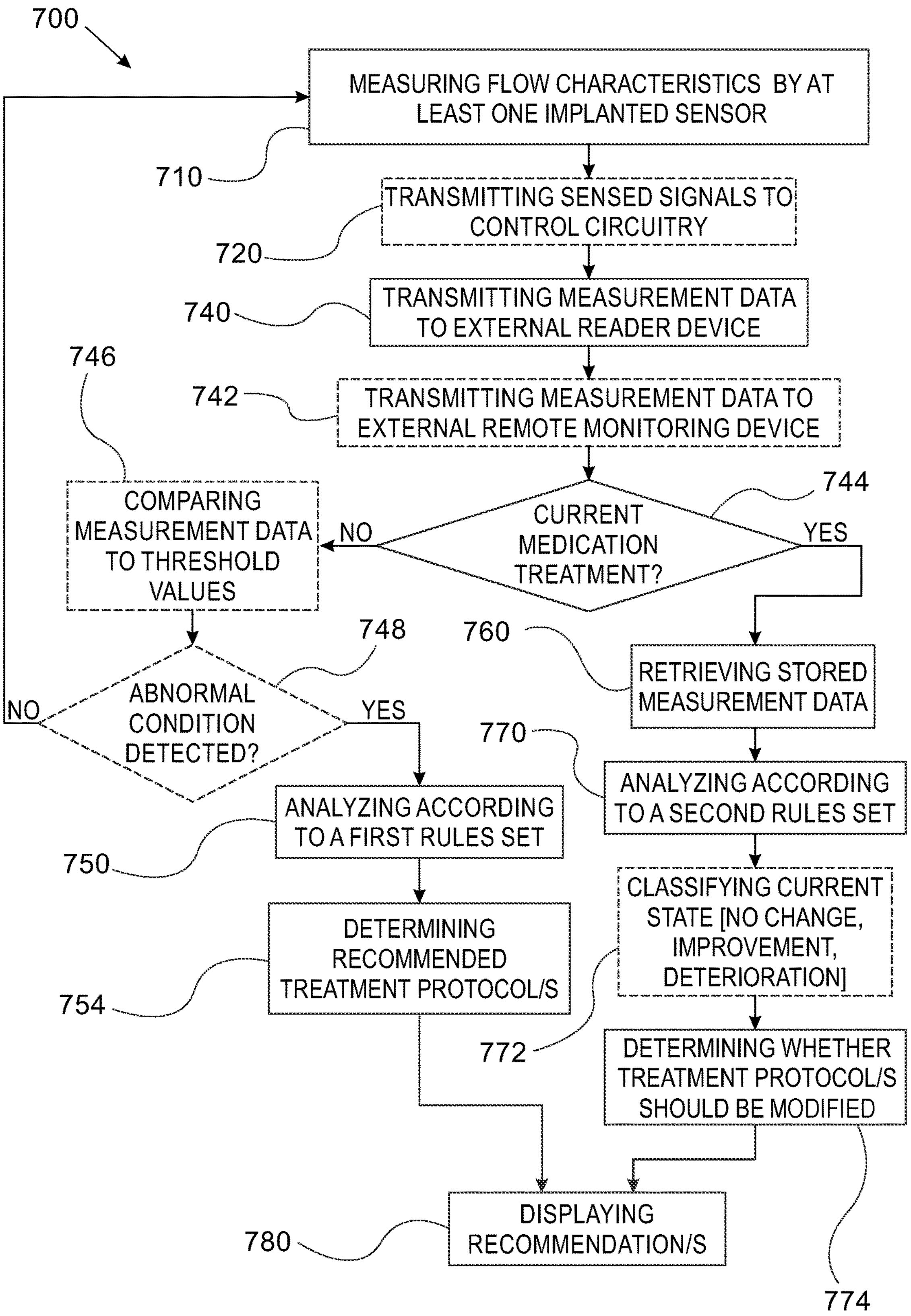

FIG. 14D shows an embodiment of the heart valve monitoring method 700, which includes a step 744 of checking whether the patient is currently under a drug therapy regime for preventing, treating and/or reducing symptoms of a condition correlated with functioning of the heart valve (e.g., heart valve thrombosis influencing hemodynamic performance of the valve). The drug therapy can be adopted from a previous recommendation at step 754 of the method 700 described in relation to any of the FIGS. 14A-14C, or any modification thereof. If the patient is not under current drug therapy regime, steps 750 to 780, and optionally steps 746 and 748, may be executed as described above in relation to FIG. 14C, wherein the rule set at step 750 is a first rule set, relevant for a scenario in which the patient is not undergoing current specific drug therapy to treat a condition correlated with heart valve functioning.

If the patient is undergoing specific treatment protocols to treat a condition associated with heart valve functioning, stored measurement data may be retrieved at step 760, so as to enable comparison of current measurement data with stored measurement data to identify improvement or deterioration in the patient's condition.

The current measurement data and the retrieved (i.e., previously stored) measurement data may be analyzed in step 770, together with any additional supplementary data described for the analysis of step 750, according to a second rules set. In some applications, the second rules set may be different from the first rules set. Alternatively, a unified rules set may be utilized for both step 750 and step 770. Thus, in some applications, the first rules set and the second rules set are identical.

According to some embodiments, the analysis performed according to the second rules set in step 770, may further include an optional step 772 of classifying the progression (or current state) of the condition for which the current treatment protocol has been previously advised, wherein such state classification may include no-change, improvement, or deterioration. For example, a preventive drug therapy protocol could have been previously prescribed to prevent an onset or formation of valve thrombosis, and the classification step 772 may tag the current state as "no change", which may be interpreted as a favorable outcome, indicating that no thrombus has been formed within the valve. In another example, a drug therapy protocol could have included recommendations for anithrombotic drug therapy to treat subclinical leaflet thrombosis (for example, assumed to be present due to a rise in transvalvular pressure gradient). Worsening of the condition (e.g., indicated by a higher pressure gradient) may result in recommendations to modify the current drug therapy regime—such as by termination thereof, replacement with different drugs, or adjusting drug dosage. On the other hand, improvement of the condition may result in recommendations to proceed with the current protocol, or to modify it (e.g., to terminate current treatment, or reduce dosage).

At step 774, a determination is made for a recommended course of action, based on the analysis performed at step 770 and the optional classification at step 772. The determination may include instructions to proceed with the current drug therapy without modification, or to modify it. Treatment protocol modification may include instructions for termination of the current drug therapy, replacement with an alternative drug therapy, or adjustment of the current therapy—for example by instructing to change the treatment period, drug dosage, and the like. The recommended course of action for the current drug therapy regimen is displayed at step 780.

Advantageously, a method 700 including a step of inquiring whether the patient is currently under a previously recommended drug therapy 744, followed by an analysis 770 of the current measurement data along with retrieved (i.e., previously stored) measurement data, may enable to perform ongoing evaluation of the effectiveness and adequacy of previously recommended drug therapy regimens. This data may be stored, for example in at least one external remote storage member 494, for subsequent evaluation of the adequacy and outcome of various treatment protocols for patients having different profiles and comorbidities.

In some applications, at least one external remote monitoring device 488 can utilize big data analysis of all (or some) of the available patients having an implanted monitoring apparatus 102, in order to detect treatment success rates of specific drug therapy regimens, classifying highly successful drug therapy protocols and updating the rules sets, so as to optimize future recommendations that may be provided, for example, by monitoring systems 400. Machine learning may be utilized to produce constant improvement of the parameters and types of rules included in the rules sets (e.g., the first rules set and/or the second rules set), as new data that may include treatment success rates associated with patient-specific profiles and comorbidities, is collected constantly from the analysis performed at step 770.

Advantageously, measurement of flow characteristics associated with heart valve functioning, by at least one sensor 158 of an implanted monitoring apparatus 102, which may be communicated to an external reader device 188, according to any of the embodiments of the current disclosure, can be beneficial in tracking the progression of a previously detected condition for which a treatment protocol has been advised, such as improvement or worsening thereof. Compared with alternative conventional imaging techniques, such as external ultrasound readers or CT, the proposed devices (e.g., monitoring apparatus 102), systems (e.g., monitoring system 400) and methods (e.g., method 700) for monitoring functioning of a heart valve, are significantly simpler, safer, more accurate and relatively inexpensive. Moreover, since heart valve functioning can be conveniently and frequently monitored after adoption of a recommendation for a specific treatment protocol is adopted, adequacy and efficiency of such protocols can be evaluated, to provide instructions for modifying current treatment protocols when required, as well as for analyzing success rates of various protocols adopted by various patients, thereby enabling optimization of the rules set used to analyze measurement data and determine future recommended treatment protocols.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although the invention is described in conjunction with specific embodiments thereof, it is evident that numerous alternatives, modifications and variations that are apparent to those skilled in the art may exist. It is to be understood that the invention is not necessarily limited in its application to the details of construction and the arrangement of the components and/or methods set forth herein. Other embodiments may be practiced, and an embodiment may be carried out in various ways. Accordingly, the invention embraces all such alternatives, modifications and variations that fall within the scope of the appended claims.

The invention claimed is:

1. A valve monitoring assembly, comprising:

a prosthetic valve that is radially expandable and compressible between a radially compressed state and a radially expanded state, the prosthetic valve comprising:

a frame having an inflow end portion and an outflow end portion; and a plurality of leaflets positioned at least partially within the frame and configured to regulate a flow of blood through the prosthetic valve; and a monitoring apparatus comprising:

at least one sensor associated with the prosthetic valve, wherein the at least one sensor is selected from the group consisting of: flow sensor, pressure sensor, and temperature sensor;

a local control circuitry in communication with the at least one sensor via at least one communication channel extending therebetween, wherein the at least one communication channel is routed along one or more structural portions of the frame such that a length of the communication channel remains substantially constant during radial expansion and compression of the prosthetic valve;

at least one communication component, in communication with the local control circuitry, and configured to wirelessly transmit signals; and an energy harvesting power source, configured to be secured to a patient and comprising a self-powered energy harvesting mechanism and an energy storage member, wherein the energy storage member is configured to store energy generated by the self-powered energy harvesting mechanism, and wherein the energy harvesting power source is configured to supply power to the at least one sensor, the local control circuitry and/or the at least one communication component.

2. The valve monitoring assembly according to claim 1, wherein the energy harvesting power source is coupled to the local control circuitry.

3. The valve monitoring assembly according to claim 1, wherein the energy harvesting power source further comprises a first tissue engagement feature configured to facilitate attachment of the energy harvesting power source to a tissue of the patient.

4. The valve monitoring assembly according to claim 1, wherein the self-powered energy harvesting mechanism is a clockwork-type energy harvesting mechanism, comprising:

an oscillating weight configured to translate externally applied accelerations into oscillating rotational motions thereof;

a mechanical rectifier coupled to the oscillating weight, and configured to translate the oscillating rotational motions into a unidirectional rotation;

a spring coupled to the mechanical rectifier; and an electromagnetic micro generator coupled to the spring, and configured to convert motion of the spring into an electrical signal.

5. The valve monitoring assembly according to claim 1, wherein the self-powered energy harvesting mechanism is a solar energy harvesting mechanism, comprising a solar module comprising at least one solar cell.

6. The valve monitoring assembly according to claim 5, wherein the solar energy harvesting mechanism further comprises a power converter functionally coupled to the solar module.

7. The valve monitoring assembly according to claim 5, wherein the at least one communication component comprises a remote communication component and a local communication component, wherein the remote communication component is configured to wirelessly transmit energy generated by the solar energy harvesting mechanism to the local communication component.

8. The valve monitoring assembly according to claim 7, wherein the remote communication component comprises a coil antenna configured to electromagnetically transmit the energy stored in the energy storage member to the local communication component.

9. The valve monitoring assembly according to claim 1, wherein the frame comprises a plurality of cells bound between strut portions.

10. The valve monitoring assembly according to claim 9, wherein the at least one communication channel comprises a conductive wire or an optical fiber that extends from the at least one sensor to the local control circuitry along one or more of the strut portions defining boundaries of the plurality of cells.

11. The valve monitoring assembly according to claim 1, wherein the prosthetic valve comprises one or more actuator assemblies configured to facilitate radial expansion of the prosthetic valve, and wherein the at least one communication channel extends between the at least one sensor and the local control circuitry along at least a portion of one of the actuator assemblies.

12. The valve monitoring assembly according to claim 11, wherein the at least one sensor comprises a first sensor and a second sensor axially spaced apart and attached to the same actuator assembly selected from the one or more actuator assemblies.

13. The valve monitoring assembly according to claim 11, wherein each of the one or more actuator assemblies comprises an inner member and an outer member, the inner member being at least partially disposed within a lumen of the outer member and axially movable relative thereto to facilitate radial expansion of the prosthetic valve, wherein the at least one sensor is attached to the outer member of one of the actuator assemblies.

14. A valve monitoring assembly, comprising:

a prosthetic valve comprising a frame and a plurality of leaflets configured to regulate a flow of blood through the prosthetic valve; and a monitoring apparatus comprising:

at least one sensor associated with the prosthetic valve;

a control circuitry in communication with the at least one sensor;

at least one communication channel extending between the at least one sensor and the control circuitry; and an energy harvesting power source configured to supply power to the at least one sensor or the control circuitry, wherein the at least one communication channel is routed along one or more structural portions of the prosthetic valve such that a length of the communication channel remains substantially invariant during deformation of the prosthetic valve.

15. The valve monitoring assembly according to claim 14, wherein the at least one sensor comprises a radiopaque marker configured to provide a visible indication of a location of the at least one sensor under fluoroscopy.

16. The valve monitoring assembly according to claim 14, wherein the at least one sensor comprises a first sensor and a second sensor axially spaced apart and attached to an inflow apex and an outflow apex of the frame of the prosthetic valve, respectively.

17. The valve monitoring assembly according to claim 14, wherein the monitoring apparatus further comprises at least one communication component in communication with the control circuitry and configured to wirelessly transmit signals generated by the at least one sensor.

18. A valve monitoring system, comprising:

an implantable device that is radially expandable and compressible;

a monitoring apparatus associated with the implantable device, the monitoring apparatus comprising:

at least one sensor associated with the implantable device;

a control circuitry in communication with the at least one sensor;

at least one communication channel extending between the at least one sensor and the control circuitry, the communication channel being arranged along portions of the implantable device that maintain a substantially constant length during expansion and compression of the implantable device;

an energy harvesting power source configured to supply power to the at least one sensor or the control circuitry; and an external device configured to communicate with the monitoring apparatus to receive signals generated by the at least one sensor.

19. The valve monitoring system according to claim 18, wherein the implantable device comprises a prosthetic valve including a frame and one or more leaflets positioned at least partially within the frame and configured to regulate a flow of blood through the prosthetic valve.

20. The valve monitoring system according to claim 19, wherein the frame comprises a plurality of interconnected struts defining a plurality of cells, and wherein the at least one communication channel comprises a conductive wire or an optical fiber that extends from the at least one sensor to the control circuitry along a length of one or more of the struts without crossing one of the cells.

* * * * *